(12) United States Patent
Yang et al.

(10) Patent No.: US 8,507,481 B2
(45) Date of Patent: Aug. 13, 2013

(54) BENZOXAZINE OXAZOLIDINONE COMPOUNDS, PREPARATION METHODS AND USES THEREOF

(75) Inventors: Yushe Yang, Shanghai (CN); Qisheng Xin, Shanghai (CN); Houxing Fan, Shanghai (CN); Bin Guo, Shanghai (CN); Xin Liu, Shanghai (CN); Huili He, Shanghai (CN); Wei Li, Jiangsu (CN); Zhan Li, Jiangsu (CN)

(73) Assignees: Shanghai Institute of Materia Medica, Chinese Academy of Sciences (CN); Nanjing Changao Pharmaceutical Science & Technology Co., Limited (CN)

( * ) Notice: Subject to any disclaimer, the term of this patent is extended or adjusted under 35 U.S.C. 154(b) by 0 days.

(21) Appl. No.: 13/700,017

(22) PCT Filed: May 12, 2011

(86) PCT No.: PCT/CN2011/073961
§ 371 (c)(1),
(2), (4) Date: Jan. 30, 2013

(87) PCT Pub. No.: WO2011/147259
PCT Pub. Date: Dec. 1, 2011

(65) Prior Publication Data
US 2013/0123249 A1    May 16, 2013

(30) Foreign Application Priority Data

May 24, 2010  (CN) .......................... 2010 1 0183793
Dec. 31, 2010  (CN) .......................... 2010 1 0624875

(51) Int. Cl.
C07D 498/04       (2006.01)
A61K 31/424       (2006.01)
A61P 31/04        (2006.01)

(52) U.S. Cl.
USPC ....................................... 514/230.2; 544/101

(58) Field of Classification Search
USPC ....................................... 544/101; 514/230.2
See application file for complete search history.

(56) References Cited

FOREIGN PATENT DOCUMENTS

| CN | 1433413 | 7/2003 |
|---|---|---|
| CN | 1989134 | 6/2007 |
| WO | WO0194342 | 12/2001 |
| WO | WO2004020737 | 3/2004 |
| WO | WO2005014571 | 2/2005 |
| WO | WO2005116023 | 12/2005 |

OTHER PUBLICATIONS

Cecil Textbook of Medicine (20th Edition, vol. 2, 1996, pp. 1739-1747).*

International Search Report issued in corresponding application No. PCT/CN2011/073961, dated Aug. 18, 2011 (6 pgs).
Cui, et al., "Stereocontrolled Synthesis of Tricyclic Fused Oxazolidinone as Antibacterial Agent," J. Heterocyclic Chem., 2006, vol. 43, pp. 1071-1075 (5 pgs).
Genin, M., "Recent progress with oxazolidinone antibacterial agents," Exp. Opin. Ther. Patents, 2000, vol. 10, No. 9, pp. 1405-1414 (10 pgs).
Hutchinson, D., "Recent advances in oxazolidinone antibacterial agent research," Exp. Opin. Ther. Patents, 2004, vol. 14, No. 9, pp. 1309-1328 (20 pgs).
Barbachyn et al., "Oxazolidinone Structure—Activity Relationships Leading to Linezolid," Angew. Chem. Int. Ed., 2003, vol. 42, pp. 2010-2023 (14 pgs).
Hutchinson, D., "Oxazolidinone Antibacterial Agents: A Critical Review," Current Topics in Medicinal Chemistry, 2003, vol. 3, pp. 1021-1042 (22 pgs).
Poce et al., "New oxazolidinone derivatives as antibacterial agents with improved activity," Exp. Opin. Ther. Patents, 2008, vol. 18, No. 2, pp. 97-121 (25 pgs).
Wang, G., "Synthesis and Antibacterial Properties of Oxazolidinones and Oxazinanones," Anti-Infective Agents in Medicinal Chemistry, 2008, vol. 7, pp. 32-49 (18 pgs).
Srivastava et al., "Oxazolidinone Antibacterials and Our Experience," Anti-Infective Agents in Medicinal Chemistry, 2008, vol. 7, pp. 258-280 (23 pgs).
Kher et al., "Regiospecific Oxidative Nitration of 3,4-Dihydro-6,7-disubstituted Quinoxalin-2(1H)-ones Gives 1,4-Dihydro-5-nitro-6,7-disubstituted Quinoxaline-2,3-diones, Potent Antagonists at the NMDA/Glycine Site," J. Org. Chem., 1995, vol. 60, pp. 5838-5842 (5 pgs).
Li et al., "An Improved Protocol for the Preparation of 3-Pyridyl- and Some Arylboronic Acids," J. Org. Chem., 2002, vol. 67, pp. 5394-5397 (4 pgs).
Jo et al., "Synthesis and antibacterial activity of oxazolidinones containing pyridine substituted with heteroaromatic ring," Bioorganic & Medicinal Chemistry, 2004, vol. 12, pp. 5909-5915 (7 pgs).
Klapars et al., "Mild and Practical Method for the α-Arylation of Nitriles with Heteroaryl Halides," J. Org. Chem., 2005, vol. 70, pp. 10186-10189, (4 pgs).

(Continued)

*Primary Examiner* — Kahsay Habte
(74) *Attorney, Agent, or Firm* — Hayes Soloway P.C.

(57) ABSTRACT

Novel benzoxazine oxazolidinone compounds, preparation methods and uses thereof are disclosed, which belong to the field of pharmacy. More specifically, novel benzoxazine oxazolidinone compounds represented by the following general formula (I), preparation methods and uses thereof in preparing medicament for treating infectious diseases, especially infectious diseases caused by multi-drug resistant bacteria, are disclosed.

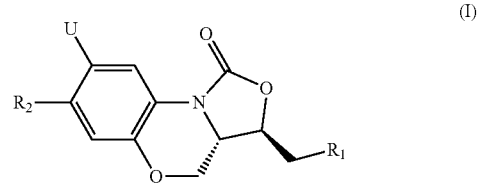

(I)

16 Claims, No Drawings

(56) References Cited

OTHER PUBLICATIONS

Wang et al., "Selective monolithiation of 2,5-dibromopyridine with butyllithium," Tetrahedron Letters, 2000, vol. 41, pp. 4335-4338, (4 pgs).

Hatanaka et al., "Preparation and antioxidant activity of α-pyridoin and its derivatives," Bioorganic & Medicinal Chemistry, 2005, vol. 13, pp. 6763-6770 (8 pgs).

Komine et al., "Synthesis and Structure—Activity Relationship Studies of Highly Potent Novel Oxazolidinone Antibacterials," J. Med. Chem, 2008, vol. 51, pp. 6558-6562 (5 pgs).

Tilley et al., "A Convenient Palladium-Catalyzed Coupling Approach to 2,5-Disubstituted Pyridines," J. Org. Chem., 1988, vol. 53, pp. 386-390 (5 pgs).

Hartner et al., "Methods for the Synthesis of 5,6,7,8-Tetrahydro-1,8-naphthyridine Fragments for $\alpha v \beta_3$ Integrin Antagonists," J. Org. Chem., 2004, vol. 69, pp. 8723-8730 (8 pgs).

Jones et al., "In Vitro Antimicrobial Activities and Spectra of U-100592 and U-100766, Two Novel Fluorinated Oxazolidinones," Antimicrobial Agents and Chemotherapy, 1996, vol. 40, No. 3, pp. 720-726 (7 pgs).

* cited by examiner

BENZOXAZINE OXAZOLIDINONE COMPOUNDS, PREPARATION METHODS AND USES THEREOF

TECHNICAL FIELD

The present invention belongs to the field of pharmacology and also relates to pharmacochemical and pharmacological field, more specifically, novel benzoxazine oxazolidinone compounds, preparation methods and uses thereof in preparing medicament for treating infectious diseases, especially infectious diseases caused by multi-drug resistant bacteria.

BACKGROUND ART

Methicillin-resistant *Staphylococcus aureus* (MRSA) and Methicillin-resistant *Staphylococcus epidermidis* (MRSE), drug-resistant *Streptococcus pneumoniae*, multi-drug resistant *Mycobacterium tuberculosis* and vancomycin-resistant *enterococcus* (VRE) present worldwide are the most difficult issues in current clinical anti-infection treatment [Exp. Opin. Ther. Patents, 2000, 10 (9): 1405; Exp. Opin. Ther. Patents, 2004, 14 (9): 1309]. Facing the challenges by multi-drug resistant bacteria, antimicrobial agents with completely new action mechanisms must be developed. Oxazolidinones are a new class of antimicrobial agents, and they have potent antibacterial activity against multi-drug resistant Gram-positive bacteria, such as methicillin-resistant *Staphylococcus aureus*, vancomycin-resistant *enterococcus*, and penicillin-resistant *Streptococcus pneumoniae* etc., as well as sensitive Gram-positive bacteria (Angew Chem. Int. Ed., 2003, 42: 2010; Current Topics in Medicinal Chemistry, 2003, 3: 1021). Oxazolidinones inhibit bacterial protein synthesis in its early stage, and their new structure and unique antibacterial mechanism different from currently available antibiotics has drawn the attention of many pharmaceutical companies and research institutions. Additionally, literatures have already reported many oxazolidinone compounds of different structure types (Expert Opin. Ther. Patents, 2008, 18, 97-121; Anti-Infective in Medicinal Chemistry, 2008, 7, 32-49; Anti-Infective in Medicinal Chemistry, 2008, 7, 258-280). Developed by the Upjohn Company (USA), linezolid was approved by the FDA in 2000 and firstly launched in the United States under the trade name Zyvox, and thus became the first approved oxazolidinone drug to be used clinically. However, existing drugs have weak antibacterial activity and side effects such as bone marrow suppression, therefore a need to research and develop new drugs with stronger antibacterial activity is warranted.

Contents Of The Invention

One of the objects of the present invention is to provide novel benzoxazine oxazolidinone compounds represented by the general formula (I) below, various optical isomers or pharmaceutically acceptable salts thereof, with more potent antibacterial activity, especially anti-multidrug resistant bacteria activity.

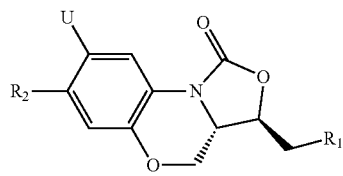

(I)

In formula (I):
U represents H or F;
$R_1$ is

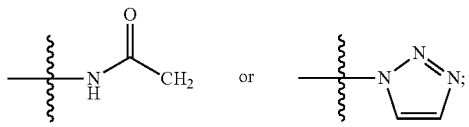

$R_2$ is a phenyl group, or a five membered or six membered aromatic or non-aromatic heterocyclic group;
Said phenyl group is optionally substituted by F, —CN, —NH$_2$, or $C_1$-$C_3$ alkylcarbonyl group;
Said five membered or six membered aromatic or non-aromatic heterocyclic group comprises at least one heteroatom selected from N, O or S, and preferably, said five membered or six membered aromatic or non-aromatic heterocyclic group comprises 1~2 N atoms. Said five membered or six membered aromatic or non-aromatic heterocyclic group is preferably furyl, thienyl, pyrrolyl, imidazolyl, thiazolyl, pyrazolyl, isothiazolyl, isoxazolyl, pyridyl, pyrimidinyl, pyridazinyl, pyrazinyl, triazolyl or tetrazolyl group. Among these groups, preferably thienyl, furyl, pyridyl, oxazolyl, isoxazolyl or thiazolyl group, more preferably thienyl, furyl, pyrimidinyl or pyridyl group, and most preferably pyridyl is used;
Said five membered or six membered aromatic or non-aromatic heterocyclic group may optionally be substituted by the following functional groups: F, Cl, Br, —OH, —NO$_2$, —CHO, —CN, —NH$_2$, —CF$_3$, —C≡CH, —C≡CCH$_2$OH, —COOH, —OR$_3$, —NHCOR$_3$, —CONR$_3$R$_4$, and —COOR$_3$, wherein each of R$_3$ and R$_4$ can independently be a C$_1$-C$_3$ alkyl group;
Or said five membered or six membered aromatic or non-aromatic heterocyclic group may optionally be substituted by C$_1$-C$_6$ straight chain or branched chain alkyl group, or C$_3$-C$_6$ cycloalkyl group, and said C$_1$-C$_6$ straight chain or branched chain alkyl group or a C$_3$-C$_6$ cycloalkyl group may optionally be substituted by —OH, —CN, or —NH$_2$;
Or said five membered or six membered aromatic or non-aromatic heterocyclic group may optionally be substituted by five membered or six membered aromatic or non-aromatic heterocyclic group, which contains at least one heteroatom selected from N and O and is either unsubstituted or substituted by C$_1$-C$_3$ alkyl group or oxygen.

Another object of the present invention is to provide the preparation method of novel benzoxazine oxazolidinone compounds represented by the general formula (I) mentioned above, various optical isomers or pharmaceutically acceptable salts thereof, with more potent antibacterial activity, especially anti-multidrug resistant bacteria activity.

A further object of the present invention is to provide a pharmaceutical composition comprising a therapeutically effective amount of one or more of the benzoxazine oxazolidinone compounds represented by the above mentioned general formula (I), various optical isomers or pharmaceutically acceptable salts thereof (including inorganic salts or organic salts) as active ingredient, as well as pharmaceutically acceptable excipients.

A further object of the present invention is to provide the application of benzoxazine oxazolidinone compounds represented by the above mentioned general formula (I), various optical isomers or pharmaceutically acceptable salts thereof in preparing medicament for treating infectious diseases, especially those caused by multi-drug resistant bacteria, including *Enterococcus, Staphylococcus aureus, Staphylococcus epidermidis*, and *pneumococcus*.

EMBODIMENTS

After extensive research, the present inventors have synthesized a series of compounds, and through antibacterial activity screening, metabolic screening and physicochemical properties research, first found that benzoxazine oxazolidinone compounds represented by the following general formula (I) have potent antibacterial activity, good drug metabolism properties and physicochemical properties, therefore are particularly suitable for use as medicaments for anti-infective therapy. On that basis, the present inventors completed the present invention.

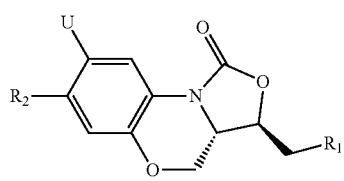
(I)

Benzoxazine oxazolidinone compounds represented by the general formula (I) of the present invention comprise at least two chiral centers, therefore they have enantiomers and diastereoisomers. For the enantiomers, two enantiomers can be obtained using the general method for chiral separation or asymmetric synthesis. Whereas for the diastereoisomers, the separation can be achieved by fractional recrystallization or chromatographic separation methods. Benzoxazine oxazolidinone compounds represented by the general formula (I) of the present invention comprise any one of the isomers mentioned above or mixtures thereof.

For pharmaceutically acceptable salts of benzoxazine oxazolidinone compounds represented by the general formula (I) of the present invention, it can be specifically listed as salts by benzoxazine oxazolidinone compounds represented by the general formula (I) mentioned above with hydrochloric acid, hydrobromic acid, hydrofluoric acid, sulfuric acid, nitric acid or phosphoric acid, and other inorganic acids, or addition salts by benzoxazine oxazolidinone compounds represented by the general formula (I) mentioned above with formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid or benzenesulfonic acid and other organic acids, as well as acidic amino acids such as aspartic acid, glutamic acid, etc.

When used for the preparation of antifungal agents, benzoxazine oxazolidinone compounds represented by the general formula (I) of the present invention or pharmaceutically acceptable salts thereof can be used alone or mixed with pharmaceutically acceptable excipients (e.g., excipients, diluents, etc.), and formulated into tablet, capsule, granule or syrup for oral administration, or liniment or injection for non-oral administration.

Preferably, the constitutional formula of representative ones among benzoxazine oxazolidinone compounds represented by the general formula (I) of the present invention is as following (or Table 1):

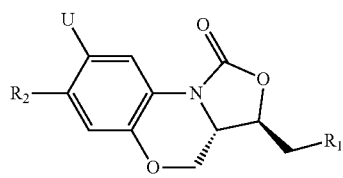
(I)

Wherein,
U represents H, $R_1$ is NHAc, $R_2$ is

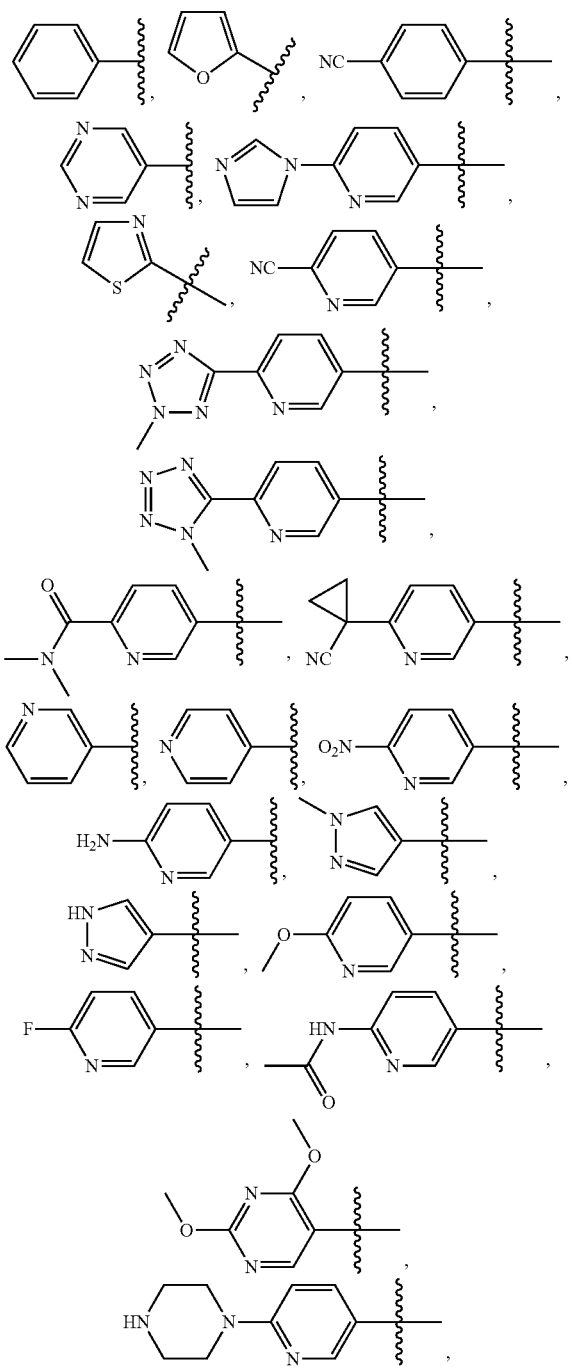

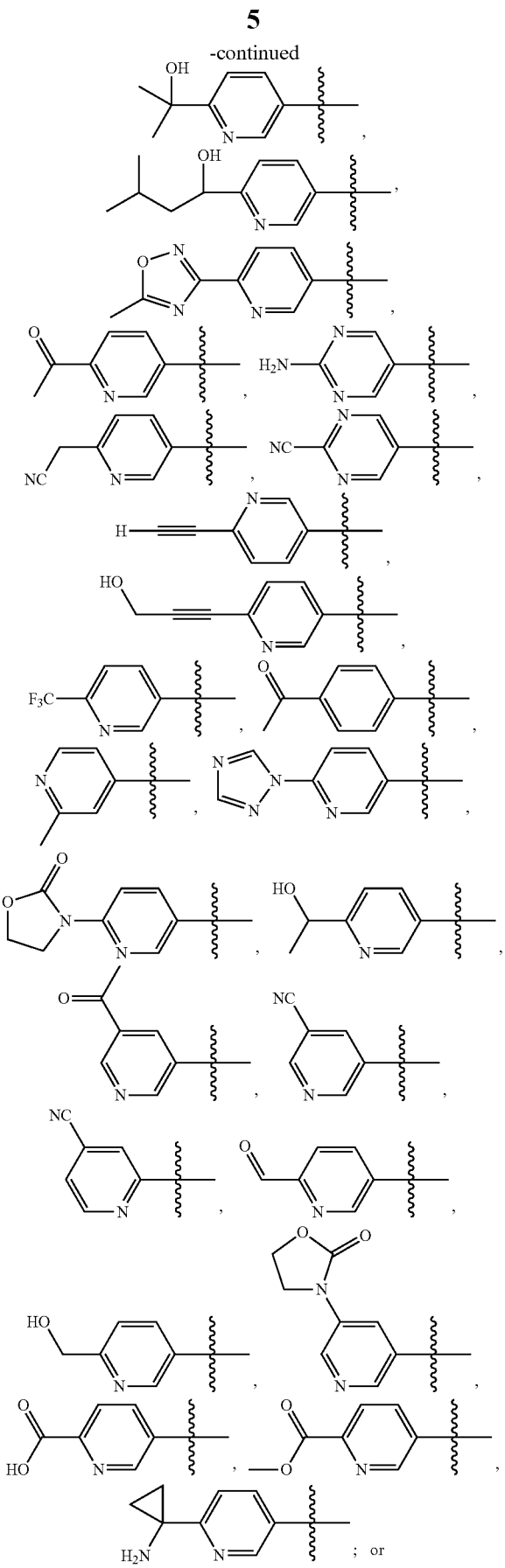
,
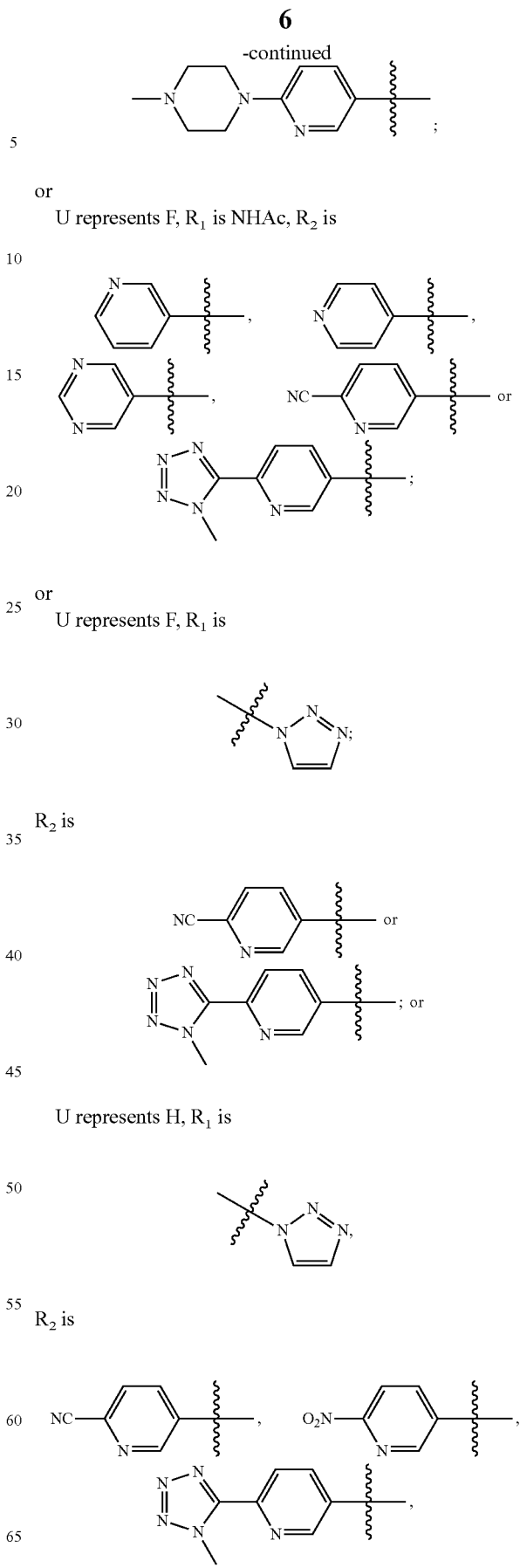
or
U represents F, $R_1$ is NHAc, $R_2$ is
or
U represents F, $R_1$ is
$R_2$ is
U represents H, $R_1$ is
$R_2$ is

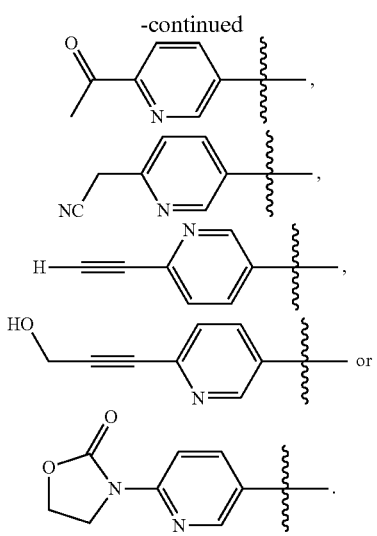

TABLE 1

Representative compounds

| Compound | U | R₁ | R₂ |
|---|---|---|---|
| 1 | H | NHAc | phenyl |
| 2 | H | NHAc | furan-2-yl |
| 3 | H | NHAc | 4-cyanophenyl |
| 4 | H | NHAc | pyrimidin-5-yl |
| 5 | H | NHAc | 2-(imidazol-1-yl)pyridin-5-yl |
| 6 | H | NHAc | thiazol-2-yl |
| 7 | H | NHAc | 6-cyanopyridin-3-yl |
| 8 | H | NHAc | 6-(2-methyltetrazol-5-yl)pyridin-3-yl |

TABLE 1-continued

Representative compounds

| Compound | U | R₁ | R₂ |
|---|---|---|---|
| 9 | H | NHAc | 6-(1-methyltetrazol-5-yl)pyridin-3-yl |
| 10 | H | NHAc | 6-(N,N-dimethylcarbamoyl)pyridin-3-yl |
| 11 | H | NHAc | 6-(1-cyanocyclopropyl)pyridin-3-yl |
| 12 | H | NHAc | pyridin-3-yl |
| 13 | H | NHAc | pyridin-4-yl |
| 14 | H | NHAc | 6-nitropyridin-3-yl |
| 15 | F | NHAc | pyridin-3-yl |
| 16 | F | NHAc | pyridin-4-yl |
| 17 | F | NHAc | pyrimidin-5-yl |
| 18 | F | NHAc | 6-cyanopyridin-3-yl |
| 19 | F | NHAc | 6-(1-methyltetrazol-5-yl)pyridin-3-yl |
| 20 | H | NHAc | 6-aminopyridin-3-yl |
| 21 | H | NHAc | 1-methylpyrazol-4-yl |

TABLE 1-continued

Representative compounds

| Compound | U | R₁ | R₂ |
|---|---|---|---|
| 22 | H | NHAc | pyrazol-4-yl |
| 23 | H | NHAc | 6-methoxypyridin-3-yl |
| 24 | H | NHAc | 6-fluoropyridin-3-yl |
| 25 | H | NHAc | 6-acetamidopyridin-3-yl |
| 26 | H | NHAc | 2,4-dimethoxypyrimidin-5-yl |
| 27 | H | NHAc | 6-(piperazin-1-yl)pyridin-3-yl |
| 28 | H | NHAc | 6-(2-hydroxypropan-2-yl)pyridin-3-yl |
| 29 | H | NHAc | 6-(1-hydroxy-3-methylbutyl)pyridin-3-yl |
| 30 | H | NHAc | 6-(5-methyl-1,2,4-oxadiazol-3-yl)pyridin-3-yl |
| 31 | H | NHAc | 6-acetylpyridin-3-yl |
| 32 | H | NHAc | 2-aminopyrimidin-5-yl |
| 33 | H | NHAc | 6-(cyanomethyl)pyridin-3-yl |
| 34 | H | NHAc | 2-cyanopyrimidin-5-yl |
| 35 | H | NHAc | 6-ethynylpyridin-3-yl |
| 36 | H | NHAc | 6-(3-hydroxyprop-1-yn-1-yl)pyridin-3-yl |
| 37 | H | NHAc | 6-(trifluoromethyl)pyridin-3-yl |
| 38 | H | NHAc | 4-acetylphenyl |
| 39 | H | NHAc | 2-methylpyridin-4-yl |
| 40 | H | NHAc | 6-(1H-1,2,4-triazol-1-yl)pyridin-3-yl |
| 41 | H | NHAc | 6-(2-oxooxazolidin-3-yl)pyridin-3-yl |
| 42 | H | NHAc | 6-(1-hydroxyethyl)pyridin-3-yl |
| 43 | H | NHAc | 5-acetylpyridin-3-yl |
| 44 | H | NHAc | 5-cyanopyridin-3-yl |
| 45 | H | NHAc | 5-cyanopyridin-2-yl |

TABLE 1-continued

Representative compounds

| Compound | U | R₁ | R₂ |
|---|---|---|---|
| 46 | H | NHAc | (5-formyl-pyridin-2-yl) |
| 47 | H | NHAc | (5-hydroxymethyl-pyridin-2-yl) |
| 48 | H | NHAc | (5-(2-oxo-oxazolidin-3-yl)-pyridin-2-yl) |
| 49 | H | triazolyl | (2-cyano-pyridin-5-yl) |
| 50 | H | triazolyl | (2-nitro-pyridin-5-yl) |
| 51 | H | triazolyl | (2-(1-methyl-tetrazol-5-yl)-pyridin-5-yl) |
| 52 | F | triazolyl | (2-cyano-pyridin-5-yl) |
| 53 | F | triazolyl | (2-(1-methyl-tetrazol-5-yl)-pyridin-5-yl) |
| 54 | H | triazolyl | (2-acetyl-pyridin-5-yl) |
| 55 | H | triazolyl | (2-cyanomethyl-pyridin-5-yl) |
| 56 | H | triazolyl | (2-ethynyl-pyridin-5-yl) |
| 57 | H | triazolyl | (2-(3-hydroxy-prop-1-ynyl)-pyridin-5-yl) |
| 58 | H | triazolyl | (2-(2-oxo-oxazolidin-3-yl)-pyridin-5-yl) |
| 59 | H | NHAc | (2-carboxy-pyridin-5-yl) |
| 60 | H | NHAc | (2-methoxycarbonyl-pyridin-5-yl) |
| 61 | H | NHAc | (2-(1-amino-cyclopropyl)-pyridin-5-yl) |
| 62 | H | NHAc | (2-(4-methyl-piperazin-1-yl)-pyridin-5-yl) |

Preferably, the constitutional formulas of representative inorganic salts and organic salts for benzoxazine oxazolidinone compounds represented by the general formula (I) of the present invention are as follows (Table 2):

TABLE 2

Salts of some compounds

| Compound | Constitutional formula |
|---|---|
| 63 | benzoxazine oxazolidinone with NC-pyridyl and NHAc, HCl salt |

TABLE 2-continued

| | Salts of some compounds |
|---|---|
| Compound | Constitutional formula |
| 64 | NC-pyridine-CH₃SO₃H–phenyl–N-oxazolidinone–NHAc |
| 65 | NC-pyridine–½ H₂SO₄–phenyl–N-oxazolidinone–NHAc |
| 66 | NC-pyridine–C₆H₅SO₃H–phenyl–N-oxazolidinone–NHAc |
| 67 | NC-CH₂-pyridine–HCl–phenyl–N-oxazolidinone–NHAc |
| 68 | NC-CH₂-pyridine–CH₃SO₃H–phenyl–N-oxazolidinone–NHAc |
| 69 | oxazolidinone-pyridine–HCl–phenyl–N-oxazolidinone–NHAc |
| 70 | oxazolidinone-pyridine–CH₃SO₃H–phenyl–N-oxazolidinone–NHAc |
| 71 | H₂N-C(cyclopropyl)-pyridine–CH₃SO₃H–phenyl–N-oxazolidinone–NHAc |

TABLE 2-continued

Salts of some compounds

| Compound | Constitutional formula |
|---|---|
| 72 | 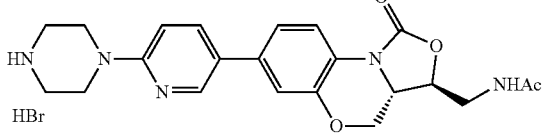 |
| 73 | 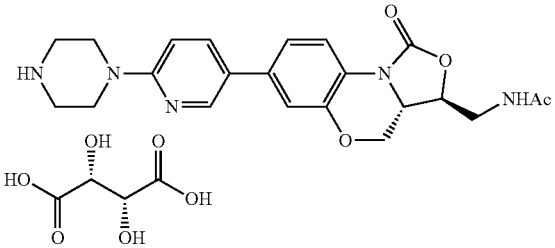 |

Preparation methods of benzoxazine oxazolidinone compounds represented by the general formula (I) of the present invention, various optical isomers or pharmaceutically acceptable salts thereof are specifically described below, but these specific methods do not constitute any limitation on the present invention. For example, reactants, solvents, alkalis, the amount of the compound used, the reaction temperature, or the time required for the reaction are not limited to the following explanation. The compounds of the present invention may also be optionally produced through combining the methods described in this specification, or a variety of synthetic methods known to those skilled in the art, and such a combination could be easily performed by a person skilled in the art, to which the present invention pertains.

In a preferred embodiment, benzoxazine oxazolidinone compounds represented by the general formula (I) of the present invention can be prepared in accordance with the method of scheme I.

Scheme I

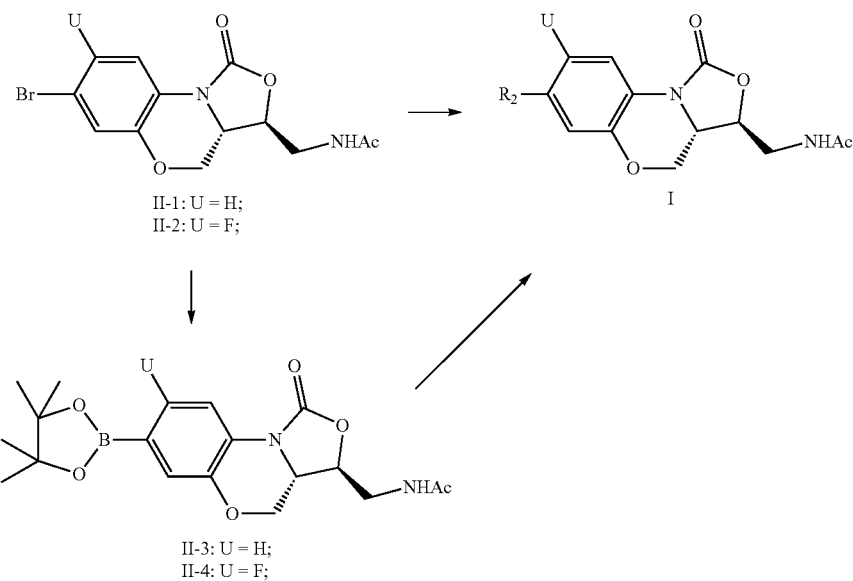

Please see above for the definition of $R_2$.

(1) Compound II-1 [J. Heterocyclic Chem., 2006, 43, 1071.] or II-2 reacts with $R_2B(OH)_2$, or $R_2$-substituted boronic acid pinacol ester under the condition of a catalyst containing metal palladium, alkaline pH, a polar solvent, as well as the protection of inert gas at a temperature range of room temperature to 120° C. for 2-48 hours, to obtain the corresponding Compound I. Said catalyst containing metal palladium can be tetrakis(triphenylphosphine)palladium [Pd(PPh$_3$)$_4$], [1,1'-bis(diphenylphosphino)ferrocene] palladium dichloride [Pd(dppf)Cl$_2$], [1,1'-bis(diphenylphosphino)ferrocene]palladium dichloride dichloromethane complex [Pd(dppf)Cl$_2$·CH$_2$Cl$_2$], tris(dibenzylidene acetone)dipalladium (0) [Pd$_2$(dba)$_3$], or bis(dibenzylidene acetone)palladium (0) [Pd(dba)$_2$]; for said alkaline condition, the following alkalis can be used: cesium carbonate (Cs$_2$CO$_3$), potassium carbonate (K$_2$CO$_3$) or potassium fluoride (KF); said polar solvent can be: 1,4-dioxane, tetrahydrofuran (THF), dimethoxyethane (DME), ethanol or water or mixtures thereof; said inert gas can be nitrogen or argon.

Or (2) Compound II-1 or II-2 reacts with bis(pinacolato)diboron under the condition of a catalyst containing metal palladium, a phosphine-containing ligand, alkaline pH, a polar solvent, as well as the protection of inert gas at a temperature range of room temperature to 100° C. for 0.5 to 48 hours, to obtain Compound II-3 or II-4 respectively. Said catalyst containing metal palladium can be Pd(PPh$_3$)$_4$, Pd(dppf)Cl$_2$, Pd(dppt)Cl$_2$·CH$_2$Cl$_2$ or Pd(dba)$_2$; said phosphine-containing ligand can be biphenyl-2-yl di-tert-butylphosphine; for said alkaline condition, the following alkalis can be used: potassium acetate (KOAc), sodium acetate (NaOAc), potassium tert-butoxide ($^t$BuOK) or sodium tert-butoxide ($^t$BuONa); said polar solvent can be: dimethyl sulfoxide (DMSO), dimethylformamide (DMF), 1,4-dioxane, THF or toluene; said inert gas can be nitrogen or argon.

Compound II-3 or II-4 reacts with bromides $R_2Br$ under the condition of a catalyst containing metal palladium, alkaline pH, a polar solvent, as well as the protection of inert gas at a temperature range of room temperature to 120° C. for 2-24 hours, to obtain corresponding Compound I. Said catalyst containing metal palladium can be Pd(PPh$_3$)$_4$, Pd(dppf)Cl$_2$·CH$_2$Cl$_2$ or Pd(dppf)Cl$_2$; for said alkaline condition, the following alkalis can be used: Cs$_2$CO$_3$, K$_2$CO$_3$ or KF; said polar solvent can be: 1,4-dioxane, THF, water, DME, ethanol, DMF or toluene or mixtures thereof; said inert gas can be nitrogen or argon.

It may further include:

(3) Compound I with $R_2$ containing —NO$_2$ in a polar solvent undergoes catalytic hydrogenation under the condition of a metal catalyst to obtain Compound I with $R_2$ containing —NH$_2$. Said polar solvent can be dichloromethane, methanol, ethanol, THF or mixtures thereof; said metal catalyst can be palladium/carbon or other palladium- or nickel-containing metal catalysts. More specifically, Compound I with $R_2$ containing —NO$_2$ undergoes catalytic hydrogenation using dichloromethane, methanol, ethanol, THF or mixtures thereof as the solvent, palladium/carbon or other palladium- or nickel-containing metal catalysts as the catalyst, at normal temperature and pressure to obtain Compound I with $R_2$ containing —NH$_2$.

In a preferred embodiment, benzoxazine oxazolidinone compounds represented by the general formula (I) of the present invention can be prepared in accordance with the method of scheme II.

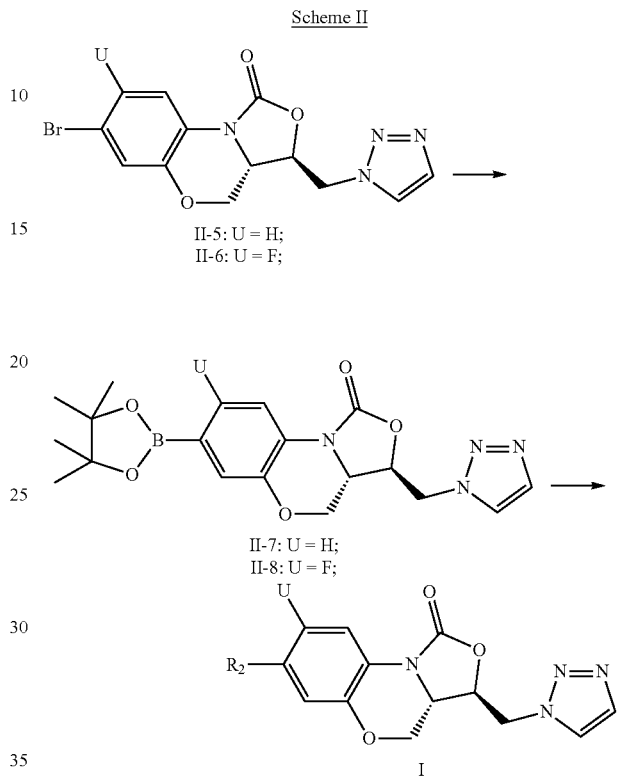

Scheme II

II-5: U = H;
II-6: U = F;

II-7: U = H;
II-8: U = F;

I

Please see above for the definition of $R_2$.

Compound II-5 or II-6 reacts with bis(pinacolato)diboron under the condition of catalysis by a catalyst containing metal palladium, a phosphine-containing ligand, alkaline pH, a polar solvent, as well as the protection of inert gas at a temperature range of room temperature to 100° C. for 0.5 to 48 hours, to obtain Compound II-7 or II-8 respectively. Said catalyst containing metal palladium can be Pd(dba)$_2$, Pd(dppf)Cl$_2$·CH$_2$Cl$_2$ or Pd(dppf)Cl$_2$; said phosphine-containing ligand can be biphenyl-2-yl di-tert-butylphosphine; for said alkaline condition, the following alkalis can be used: KOAc, NaOAc, $^t$BuOK or $^t$BuONa; said polar solvent can be DMSO, 1,4-dioxane or DME; said inert gas can be nitrogen or argon.

Compound II-7 or II-8 reacts with bromides $R_2Br$ under the condition of a catalyst containing metal palladium, alkaline pH, a polar solvent, as well as the protection of inert gas at a temperature range of room temperature to 120° C. for 2-24 hours, to obtain the corresponding Compound I. Said catalyst containing metal palladium can be Pd(dba)$_2$, Pd(dppf)Cl$_2$·CH$_2$Cl$_2$ or Pd(dppf)Cl$_2$; for said alkaline condition, the following alkalis can be used: KOAc, K$_2$CO$_3$ or NaOAc; said polar solvent can be DMF, 1,4-dioxane, ethanol, water or mixtures thereof; said inert gas can be nitrogen or argon.

In a preferred embodiment, Compound II-2 of the present invention can be prepared in accordance with the equations of scheme III.

Scheme III

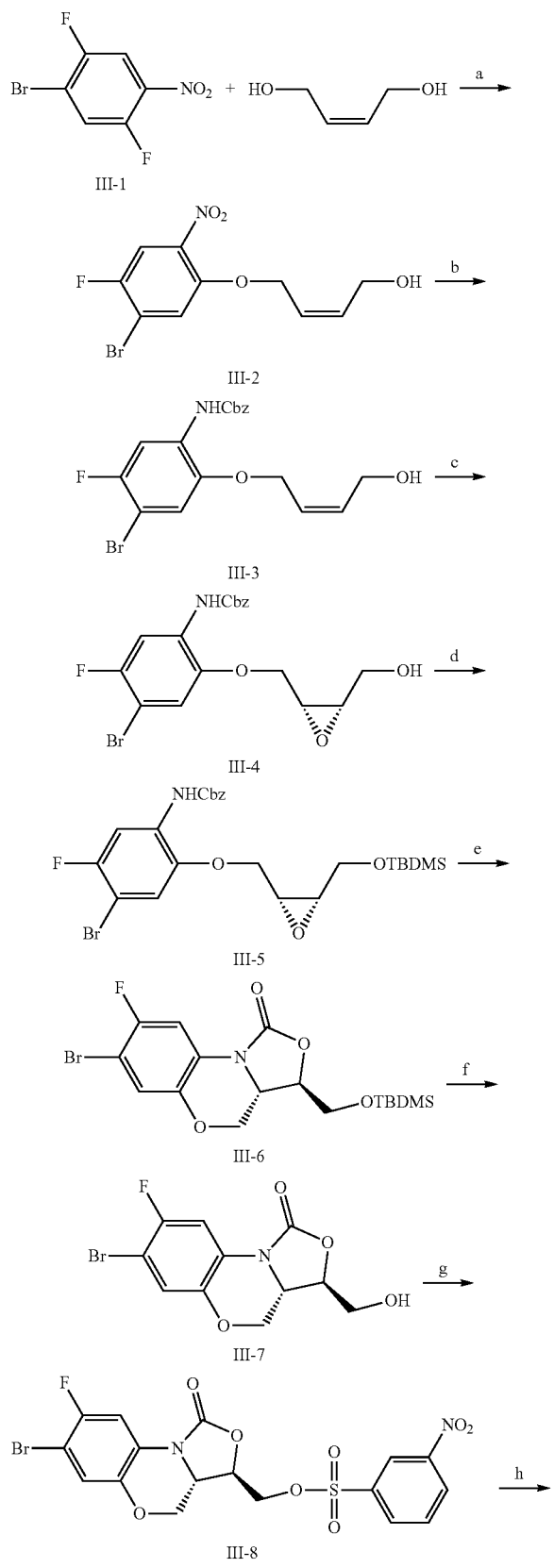

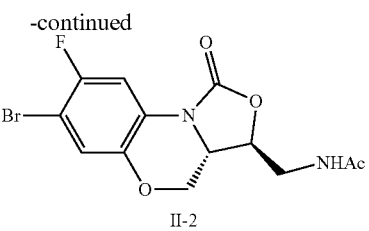

a. Compound III-1 [J. Org. Chem., 1995, 60, 5838.] reacts with (Z)-2-Butene-1,4-diol under the condition of alkaline pH, molecular sieve, a polar solvent, as well as the protection of inert gas at −20° C. to 120° C. for 1 to 24 hours to produce Compound III-2. For said alkaline condition, the following alkalis can be used: $K_2CO_3$, NaH, NaOH or KOH; said molecular sieve can be 4 Å molecular sieve; said polar solvent can be DMF, THF or DME; said inert gas can be nitrogen or argon.

b. Compound III-2 reacts under the condition of a reducing agent and a polar solvent at room temperature for 2-48 hours so that the nitro group is reduced to a corresponding amino compound. Said reducing agent can be zinc powder, iron powder, ammonium formate or ammonium chloride; said polar solvent can be methanol or THF.

The amino compound continues to react with benzyl chloroformate (CbzCl) under alkaline condition and in a polar solvent to obtain Compound III-3, in which the amino group is protected by the benzyloxycarbonyl (Cbz). For said alkaline condition, the following alkalis can be used: $NaHCO_3$, $KHCO_3$, $Na_2CO_3$ or $K_2CO_3$; said polar solvent can be water, acetone, or THF or mixtures thereof.

c. Compound III-3 and an oxidant undergo sharpless epoxidation reaction under the condition of an L-(+)-tartaric ester, a titanium reagent and molecular sieve, as well as in a polar solvent at a temperature range of room temperature to 40° C. to obtain the corresponding chiral epoxidation product III-4. Said oxidant can be tert-butylhydroperoxide (TBHP) dissolved in toluene; said tartaric ester, is L-(+)-diethyl tartrate (L-(+)-DET) or L-(+)-dimethyl tartrate; said molecular sieve can be 4 Å molecular sieve; said titanium reagent can be titanium tetraisopropoxide (Ti(O—$^i$Pr)$_4$; said polar solvent can be methylene chloride or chloroform.

d. Compound III-4 reacts with tert-butyldimethylsilyl chloride (TBDMSCl) in the presence of an organic alkali and in a polar solvent at room temperature for 2-6 hours to obtain Compound III-5. Said organic alkali can be imidazole or 4-dimethylaminopyridine (DMAP); said polar solvent can be DMF, DMSO, THF, or 1,4-dioxane.

e. Compound III-5 reacts under the alkaline condition and in a polar solvent at a temperature range of room temperature to 78° C. for 6-24 hours, to obtain Compound III-6. For said alkaline condition, the following alkalis can be used: n-butyllithium or lithium diisopropylamide (LDA); said polar solvent can be THF or DME.

f. Compound III-6 reacts in the presence of a fluorine-containing reagent, in a polar solvent and at room temperature for 1-6 hours, to produce Compound III-7 through removal of the tert-butyldimethylsilyl (TBDMS) protecting group. Said fluorine-containing reagent can be tetra-n-butylammonium fluoride ($^n$Bu$_4$NF); said polar solvent can be THF or DME.

g. Compound III-7 reacts with 3-nitrobenzenesulfonyl chloride (NOSCl) in the presence of an organic alkali, in a polar solvent, and at a temperature range of room temperature to 10° C. for 2-12 hours to obtain corresponding Compound III-8. Said organic alkali can be triethylamine or pyridine; said polar solvent can be methylene chloride or chloroform.

h. Compound III-8 reacts with stronger ammonia water in a polar solvent at a temperature range of room temperature to 80° C. for 24-72 hours to obtain corresponding amino compound. Said polar solvent can be acetonitrile, isopropanol, or ethanol or mixtures thereof. Said amino compound reacts with an acetylating agent (e.g., acetylchloride or acetic anhydride) in the presence of an organic alkali, in a polar solvent and at a temperature range of room temperature to 10° C. for 0.5-8 hours to obtain the corresponding Compound II-2. Said organic alkali can be triethylamine or pyridine; said polar solvent can be methylene chloride or chloroform.

In a preferred embodiment, Compound II-5 and II-6 of the present invention can be prepared in accordance with the equations of scheme IV.

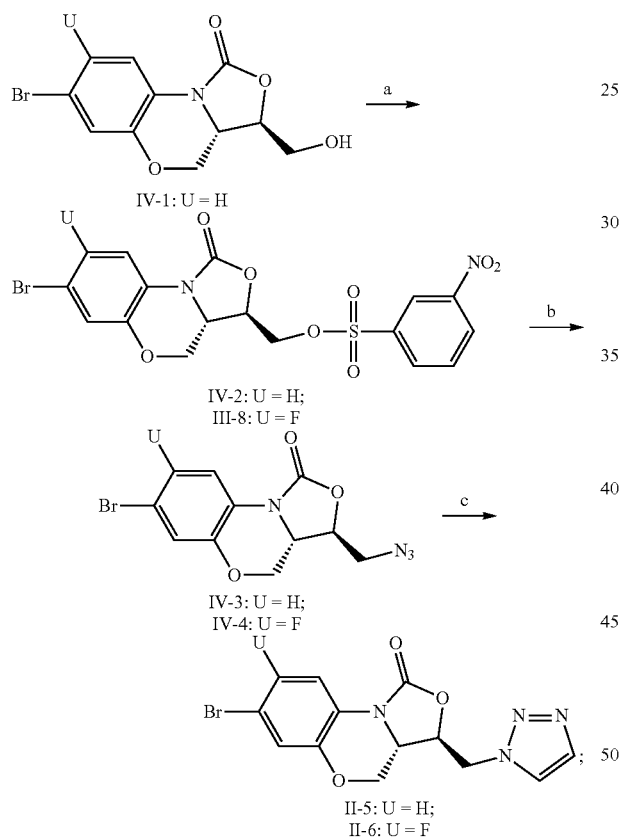

Scheme IV a. Compound IV-1 [J. Heterocyclic Chem., 43, 2006, 1071.] reacts with 3-nitrobenzene sulfonyl chloride (NOSCl) in the presence of an organic alkali, in a polar solvent, and at a temperature range of room temperature to 10° C. for 2-12 hours to obtain corresponding Compound IV-2. Said organic alkali can be triethylamine or pyridine; said polar solvent can be methylene chloride or chloroform.

b. Compound IV-2 or III-8 reacts with an azide in a polar solvent at a temperature range of room temperature to 120° C. for 1-48 hours, to obtain Compound IV-3 and IV-4 respectively. Said polar solvent can be DMF or DMSO; said azide can be sodium azide, potassium azide or trimethylsilyl azide.

c. Compound IV-3 and IV-4 reacts in vinyl acetate (CH$_3$COOCH═CH$_2$), in the presence of a copper-containing catalyst and being heated to 40-80° C. for 12-84 hours, to obtain Compound II-5 and II-6. Said copper-containing catalyst can be CuCl or CuI.

EXAMPLES

The present invention is explained more specifically in the following preparation examples and examples. However, it should be understood that these preparation examples and examples are only for illustration of the present invention, and not in any way to limit the scope of the present invention. For all preparation examples and examples, melting points are measured with X-4 melting point instrument, and the thermometer is not calibrated; $^1$H-NMR is recorded with Varian Mercury 300 or Varian Mercury 400 nuclear magnetic resonance (NMR), chemical shift is expressed in δ (ppm); silica gel is used for separation, unless otherwise specified, it is 200-300 mesh. The ratio for preparing the eluent is by volume.

I. Preparation Examples

Example 1

N(((3S,3aS)-1-oxo-7-phenyl-1,3,3a,4-tetrahydrobenzo[b]oxazole-[3,4-d][1,4]oxazin-3-yl)methyl)acetamide (1)

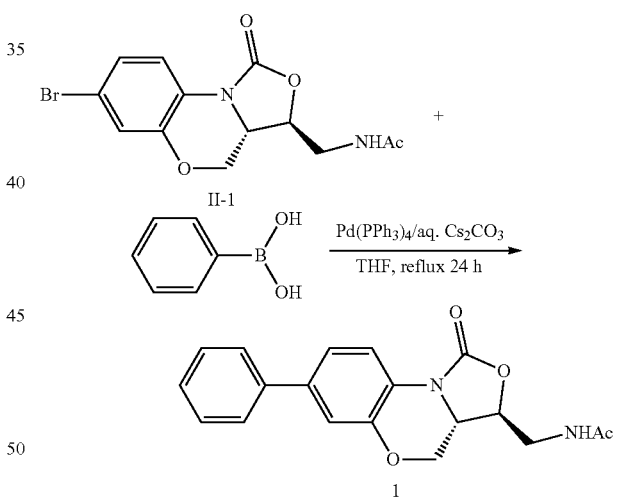

Compound II-1 [J. Heterocyclic Chem., 2006, 43, 1071.] (341 mg, 1 mmol) is dissolved in THF (30 mL), 2N cesium carbonate solution (1 mL, 2 mmol), phenylboronic acid (183 mg, 1.5 mmol) (purchased from Sigma-Aldrich Co.) and Pd(PPh$_3$)$_4$ (120 mg, 0.1 mmol) are added, under the protection of nitrogen, allow heated reflux reaction for 24 hours. TLC (CH$_2$Cl$_2$/MeOH=50:1) is used to monitor the reaction. After raw materials react completely, the reaction is stopped, and water (200 mL) is added for dilution. Extract with dichloromethane (100 mL) and the aqueous layer is re-extracted with dichloromethane (50 mL), then it is put together with dichloromethane layer, goes through water (200 mL), saturated sodium chloride solution (100 mL), drying by anhydrous sodium sulfate, and performing column chromatography (CH₂Cl₂/MeOH=100:1), to obtain 271 mg of white powdery solid (Compound 1). The yield is 80.2%.

¹H NMR (300 MHz, CDCl₃): δ 8.04 (d. J=8.39 Hz, 1H), 7.54 (m, 2 H), 7.30-7.45 (m, 3 H), 7.20-7.28 (m, 2 H), 6.17 (t, J=5.95 Hz, 1 H), 4.57 (dd, J₁=2.44 Hz, J₂=9.76 Hz, 1 H), 4.42 (m, 1 H), 3.90-4.05 (m, 2 H), 3.65-3.80 (m, 2 H), 2.05 (s, 3 H). MS (EI) m/z (%): 338 (M⁺, 100).

Example 2

N (((3S,3aS)-1-oxo-7-(furan-2-yl)-1,3,3a,4-tetrahydrobenzo[b]oxazole-[3,4-d][1,4]oxazin-3-yl)methyl)acetamide (2)

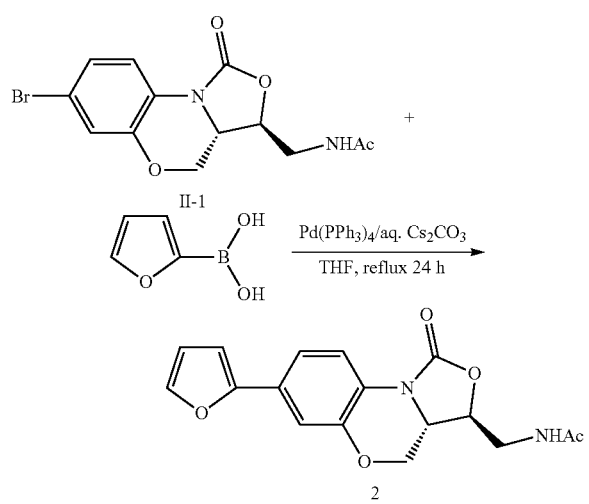

Compound II-1 (341 mg, 1 mmol) is dissolved in THF (30 mL), 2N cesium carbonate solution (1 mL, 2 mmol), 2-furanylboronic acid (168 mg, 1.5 mmol) (purchased from Sigma-Aldrich Co.) and Pd(PPh₃)₄ (120 mg, 0.1 mmol) are added, and follow the method described in example 1 to obtain 171 mg of white solid (Compound 2). The yield is 52.1%.

¹H NMR (300 MHz, CDCl₃): δ 8.01 (d, J=8.35 Hz, 1 H), 7.18-7.33 (m, 4 H), 7.12 (dd, J=3.57 Hz, J₂=4.95 Hz, 1 H), 6.17 (t, J=6.23 Hz, 1 H), 4.56 (dd, J₂=2.12 Hz, J₂=9.58 Hz, 1 H), 4.41 (m, 1 H), 3.85-4.00 (m, 2 H), 3.61-3.78 (m, 2 H), 2.03 (s, 3 H). MS (EI) m/z (%): 328 (M⁺, 100).

Example 3

N(((3S,3aS)-7-(4-cyanophenyl)-1-oxo-1,3,3a,4-tetrahydrobenzo[b]oxazole-[3,4-d][1,4]oxazin-3-yl)methyl)acetamide (3)

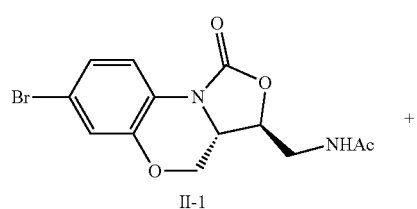

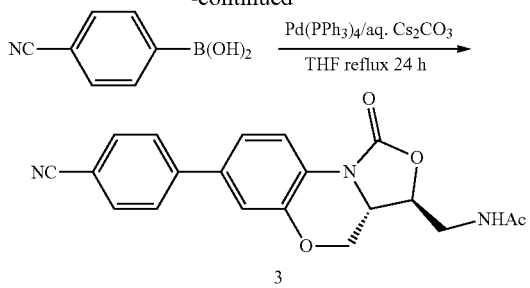

Compound II-1 (205 mg, 0.6 mmol) is dissolved in THF (20 mL), 2N cesium carbonate solution (0.6 mL, 1.2 mmol), 4-cyanophenylboronic acid (118 mg, 0.8 mmol) (J. Org. Chem., 67, 2002, 5394-5397) and Pd(PPh₃)₄ (56 mg, 0.048 mmol) are added, and follow the method described in example 1 to obtain 127 mg of white solid (Compound 3). The yield is 58.5%.

¹H NMR (300 MHz, CDCl₃): δ 8.11 (d, J=8.51 Hz, 1 H), 7.71 (d, J=6.74 Hz, 2 H), 7.63 (d, J=6.74 Hz, 2 H), 7.20-7.26 (m, 2 H), 6.07 (t, J=6.13 Hz, 1 H), 4.60 (dd, J=1.64 Hz, J₂=9.96 Hz, 1 H), 4.44 (m, 1 H), 3.90-4.08 (m, 2 H), 3.64-3.80 (m, 2 H), 2.05 (s, 3 H). MS (EI) m/z (%): 363 (M⁺, 31), 262 (100).

Example 4

N(((3S,3aS)-1-oxo-7-(pyrimidin-5-yl)-1,3,3a,4-tetrahydrobenzo[b]oxazole-[3,4-d][1,4]oxazin-3-yl)methyl)acetamide (4)

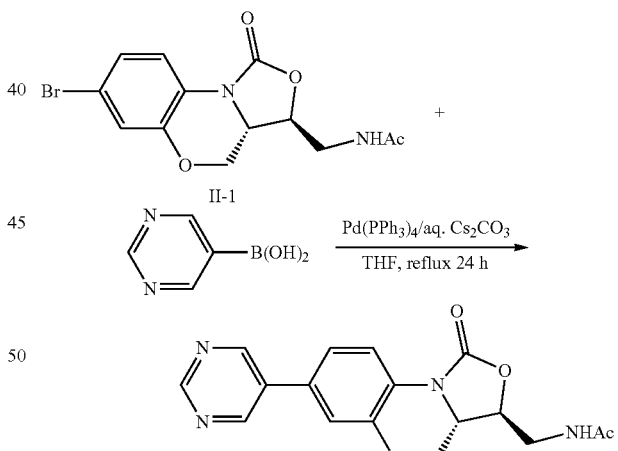

Compound II-1 (273 mg, 0.8 mmol) is dissolved in THF (20 mL), 2N cesium carbonate solution (0.8 mL, 1.6 mmol), 3-pyridinylboronic acid (124 mg, 1 mmol) (J. Org. Chem., 67, 2002, 5394-5397) and Pd(PPh₃)₄ (70 mg, 0.06 mmol) are added, and follow the method described in example 1 to obtain 214 mg of white solid (Compound 4). The yield is 78.4%.

¹H NMR (300 MHz, CDCl₃): δ 9.20 (s, 1 H), 8.92 (s, 2 H), 8.15 (d, J=8.50 Hz, 1 H), 7.20 (m, 2 H), 6.16 (t, J=6.16 Hz, 1 H), 4.61 (dd, J₁=2.63 Hz, J₂=10.14 Hz, 1 H), 4.46 (m, 1 H), 4.00-4.05 (m, 1 H), 3.94 (t, J=10.04 Hz, 1 H), 3.74 (m, 2 H), 2.06 (s, 3 H). MS (EI) m/z (%): 340 (M+, 78), 212 (100).

Example 5

N(((3S,3aS)-7-(6-(1H-imidazol-1-yl)pyridin-3-yl)-1-oxo-1,3,3a,4-tetrahydrobenzo[b]oxazole-[3,4-d][1,4]oxazin-3-yl)methyl)acetamide (5)

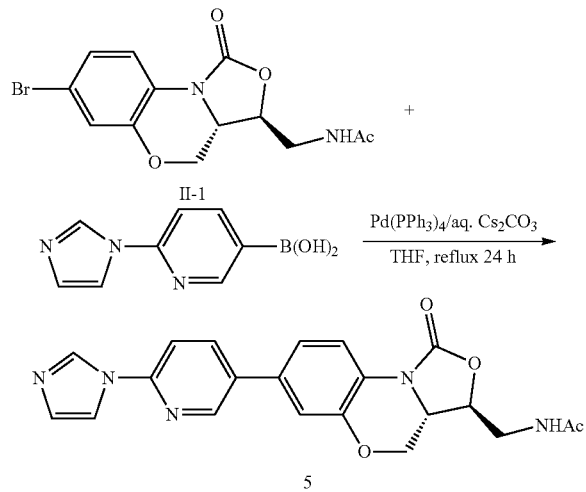

Compound II-1 (273 mg, 0.8 mmol) is dissolved in THF (20 mL), 2N cesium carbonate solution (0.8 mL, 1.6 mmol), 6-(1-imidazolyl)-3-pyridinylboronic acid (227 mg, 1.2 mmol) (J. Org. Chem., 67, 2002, 5394-5397) and Pd(PPh$_3$)$_4$ (70 mg, 0.06 mmol) are added, and follow the method described in example 1 to obtain 245 mg of white solid (Compound 5). The yield is 75.6%.

$^1$H NMR (300 MHz, DMSO-d$_6$): δ 8.81 (d, J=2.44 Hz, 2 H), 8.60 (s, 1 H), 8.32 (m, 2 H), 8.02 (m, 2 H), 7.90 (d, J=8.77 Hz, 1 H), 7.47 (m, 2 H), 7.16 (s, 1 H), 4.45-4.62 (m, 2 H), 4.00-4.14 (m, 2 H), 3.48-3.65 (m, 2 H), 1.87 (s, 3 H). MS (ESI) m/z: 460.3 (M+1)+.

Example 6

N(((3S,3aS)-1-oxo-7-(4,4,5,5-tetramethyl-1,3,2-dioxaborolan-2-yl)-1,3,3a,4-tetrahydrobenzo[b]oxazole-[3,4-d][1,4]oxazin-3-yl)methyl)acetamide (II-3)

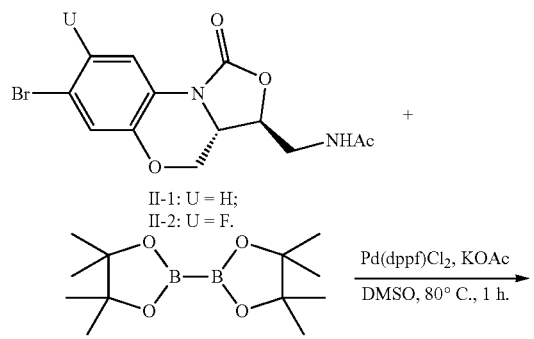

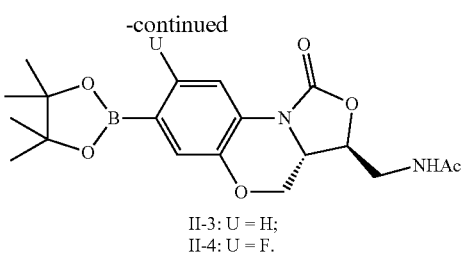

II-3: U = H;
II-4: U = F.

Bis(pinacolato)diboron (1.79 g, 7.03 mmol), potassium acetate (1.73 g, 17.58 mmol), II-1 (2.0 g, 5.86 mmol), and Pd(dppf)Cl$_2$ (480 mg, 0.59 mmol) are added to DMSO 35 mL, under stirring, replace with argon for five times, then heat to 80° C. under the protection of argon and allow reaction for 1 hour. TLC (acetone/petroleum ether=1:1) is used to monitor the reaction. After the reaction is completed, ethyl acetate (200 mL) is added for dilution, and then wash with water (100 mL×3), and saturated sodium chloride solution (50 mL), dry with anhydrous sodium sulfate, spin dry, and perform column chromatography (petroleum ether/ethyl acetate=1:1). 1.89 g of pale pink powder (Compound II-3) is obtained. The yield is 83.3%.

$^1$H NMR (300 MHz, CDCl$_3$): δ 7.95 (dd, J$_1$=1.71 Hz, J$_2$=7.82 Hz, 1 H), 6.92-7.10 (m, 2 H), 6.57 (br s, 1 H), 4.53 (dd, J$_1$=2.44 Hz, J$_2$=10.01 Hz, 1 H), 4.42 (m, 1 H), 3.96 (dd, J$_1$=2.44 Hz, J$_2$=6.84 Hz, 1 H), 3.88 (t, J=10.01 Hz, 1 H), 3.80 (m, 2 H), 2.05 (s, 3 H), 1.24 (s, 12 H). MS (ESI) m/z (%): 389.3 (M+1)+.

N(((3S,3aS)-8-fluoro-1-oxo-7-(4,4,5,5-tetramethyl-1,3,2-dioxaborolan-2-yl)-1,3,3a,4-tetrahydrobenzo[b]oxazole-[3,4-d][1,4]oxazin-3-yl)methyl)acetamide (II-4)

Bis(pinacolato)diboron (1.79 g, 7.03 mmol), potassium acetate (1.73 g, 17.58 mmol), II-2 (2.10 g, 5.86 mmol), and Pd(dppf)Cl$_2$ (480 mg, 0.59 mmol) are added to DMSO 35 mL, and follow the procedure described above to obtain 1.90 g of pale pink powder (Compound II-4). The yield is 80%.

$^1$H NMR (300 MHz, CDCl$_3$): δ 7.42 (d, J=9.61 Hz, 1 H), 7.05 (d, J=6.32 Hz, 1 H), 6.17 (t, J=6.23 Hz, 1 H), 4.58 (dd, J$_1$=2.74 Hz, J$_2$=10.41 Hz, 1 H), 4.45 (m, 1 H), 4.02 (m, 1 H), 3.88 (t, J=10.01 Hz, 1 H), 3.78 (m, 2 H), 2.05 (s, 3 H), 1.24 (s, 12 H). MS (ESI) m/z (%): 407.2 (M+1)+.

Example 7

N(((3S,3aS)-1-oxo-7-(thiazol-2-yl)-1,3,3a,4-tetrahydrobenzo[b]oxazole-[3,4-d][1,4]oxazin-3-yl)methyl)acetamide (6)

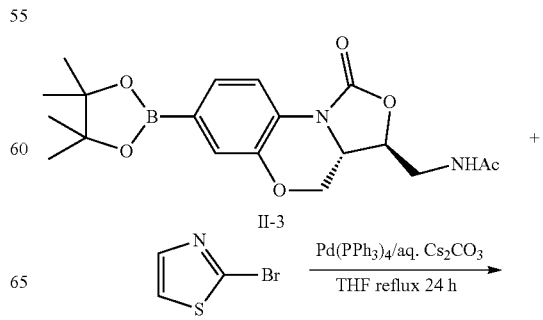

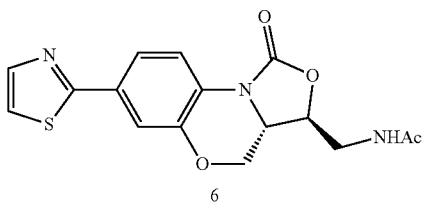

Compound II-3 (233 mg, 0.6 mmol) is dissolved in THF (20 mL), 2N cesium carbonate solution (0.6 mL, 1.2 mmol), 2-bromothiazole (purchased from Sigma-Aldrich Co.) (115 mg, 0.7 mmol) and Pd(PPh$_3$)$_4$ (70 mg, 0.06 mmol) are added, and follow the method described in example 1 to obtain 45 mg of white solid product (Compound 6). The yield is 21.7%.

$^1$H NMR (300 MHz, CDCl$_3$): δ 7.98 (d, J=8.35 Hz, 1 H), 7.84 (d, J=4.57 Hz, 1 H), 7.32 (d, J=4.57 Hz, 1 H), 7.12 (m, 1 H), 7.06 (dd, J$_1$=3.81 Hz, J$_2$=4.99 Hz, 1 H), 6.16 (t, J=6.19 Hz, 1H), 4.56 (dd, J$_1$=2.20 Hz, J$_2$=9.65 Hz, 1 H), 4.40 (m, 1 H), 3.85-4.01 (m, 2 H), 3.61-3.76 (m, 2H), 2.04 (s, 3 H). MS (EI) m/z (%): 345 (M$^+$, 100).

Example 8

N-(((3S,3aS)-7-(6-cyanopyridin-3-yl)-1-oxo-1,3,3a,4-tetrahydrobenzo[b]oxazole-[3,4-d][1,4]oxazin-3-yl)methyl)acetamide (7)

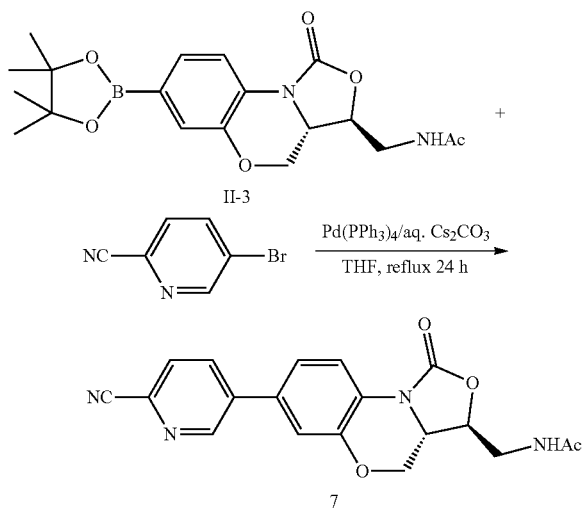

Compound II-3 (233 mg, 0.6 mmol) is dissolved in THF (20 mL), 2N cesium carbonate solution (0.6 mL, 1.2 mmol), 6-cyano-3-bromopyridine (128 mg, 0.7 mmol) (Bioorg. Med. Chem., 12, 2004, 5909-5915) and Pd(PPh$_3$)$_4$ (70 mg, 0.06 mmol) are added, and follow the method described in example 1 to obtain 41 mg of white solid product (Compound 7). The yield is 19%.

$^1$H NMR (300 MHz, CDCl$_3$): δ 8.90 (d, J=0.80 Hz, 1 H), 8.16 (d, J=8.21 Hz, 1 H), 7.96 (dd, J=2.20 Hz, J$_2$=8.07 Hz, 1 H), 7.76 (dd, J=0.80 Hz, J$_2$=8.21 Hz, 1 H), 7.22 (m, 2 H), 6.17 (t, J=6.13 Hz, 1 H), 4.62 (dd, J=2.64 Hz, J$_2$=10.06 Hz, 1 H), 4.48 (m, 1 H), 4.08 (dd, 2.63 Hz, J$_2$=7.03 Hz, 1 H), 3.94 (t, J=10.12 Hz, 1 H), 3.76 (m, 2 H), 2.07 (s, 3 H). MS (ESI) m/z: 365.2 (M+1)$^+$.

Example 9

N(((3S,3aS)-7-(6-(2-methyl-2H-tetrazol-5-yl)pyridin-3-yl)-1-oxo-1,3,3a,4-tetrahydrobenzo[b]oxazole-[3,4-d][1,4]oxazin-3-yl)methyl)acetamide (8)

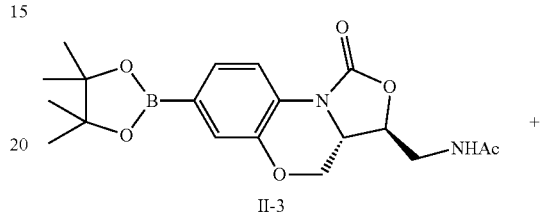

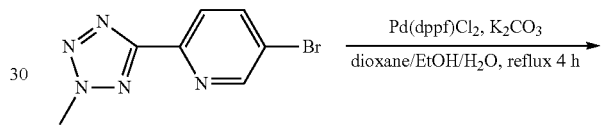

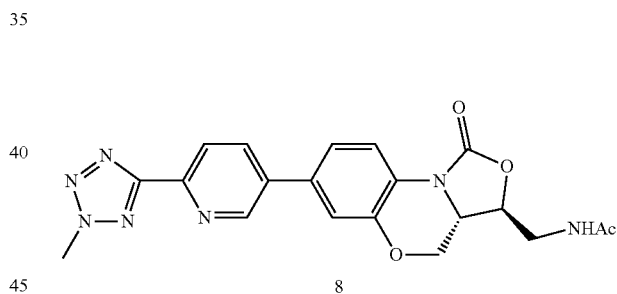

Compound II-3 (311 mg, 0.8 mmol) and 5-bromo-2-(2-methyl-2H-tetrazol-5-yl)pyridine (240 mg, 1 mmol) (Bioorg. Med. Chem., 12, 2004, 5909-5915) are dissolved in 1,4-dioxane (10 mL), ethanol (3 mL) and water (3 mL), add K$_2$CO$_3$ (311 mg, 2.4 mmol), replace with nitrogen for three times, and then add Pd(dppf)Cl$_2$ (40 mg, 0.048 mmol). Allow heated reflux reaction for 4 hours under the protection of nitrogen. TLC (CH$_2$Cl$_2$/MeOH=20:1) is used for monitoring the reaction. After the reaction is completed, water is added (200 mL) for dilution, and extract with dichloromethane (50 mL×3). Each of dichloromethane layers is washed with water (200 mL) and saturated sodium chloride solution (200 mL) successively. Then dichloromethane layers are merged together, and dried with anhydrous sodium sulfate, spin-dried and perform column chromatography (CH$_2$Cl$_2$/MeOH=100:1) to obtain 142 mg of white powdery solid (Compound 8). The yield is 42%.

$^1$H NMR (300 MHz, CD$_3$OD): δ 8.89 (d, J=1.50 Hz, 1 H), 8.26 (d, J=2.40 Hz, 1 H), 8.05 (m, 2 H), 7.24 (m, 2 H), 4.55

(dd, J=2.70 Hz, J₂=10.20 Hz, 1 H), 4.44 (m, 1 H), 3.85-4.05 (m, 2 H), 3.59 (d, J=4.80 Hz, 1 H), 3.16 (s, 3 H), 1.96 (s, 3 H). MS (ESI) m/z: 422.1 (M+1)⁺.

Example 10

N(((3S,3aS)-7-(6-(1-methyl-1H-tetrazol-5-yl)pyridin-3-yl)-1-oxo-1,3,3a, 4-tetrahydrobenzo[b]oxazole-[3,4-d][1,4]oxazin-3-yl)methyl)acetamide (9)

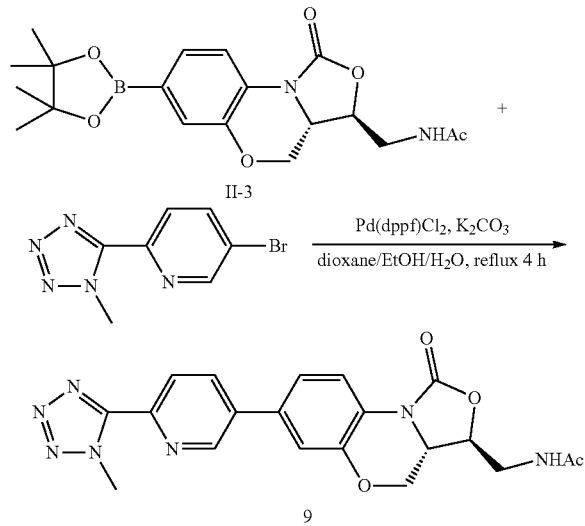

Compound II-3 (194 mg, 0.5 mmol) and 5-bromo-2-(1-methyl-2H-tetrazol-5-yl)pyridine (120 mg, 0.5 mmol) (Bioorg. Med. Chem., 12, 2004, 5909-5915) are dissolved in 1,4-dioxane (10 mL), ethanol (3 mL) and water (3 mL), add K₂CO₃ (207 mg, 1.5 mmol), replace with nitrogen, and then add Pd(dppf)Cl₂ (30 mg, 0.036 mmol). Follow the method described in example 9 to obtain 75 mg of light yellow foamy solid (Compound 9). The yield is 36.2%.

¹H NMR (300 MHz, CDCl₃): δ 8.99 (s, 1 H), 8.33 (d, J=6.62 Hz, 1 H), 8.14 (d, J=8.21 Hz, 1 H), 8.07 (d, J=7.63 Hz, 1 H), 7.30 (m, 2 H), 6.13 (br s, 1 H), 4.62 (d, J=10.51 Hz, 1 H), 4.49 (s, 3 H), 3.90-4.08 (m, 2 H), 3.76 (m, 2 H), 2.07 (s, 3 H). MS (ESI) m/z: 422.1 (M+1)⁺.

Example 11

N-(((3S,3aS)-7-(6-(N,N-dimethylaminocarbonyl)pyridin-3-yl)-1-oxo-1,3,3a,4-tetrahydrobenzo[b]oxazole-[3,4-d][1,4]oxazin-3-yl)methyl)acetamide (10)

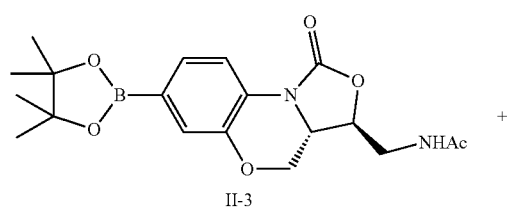

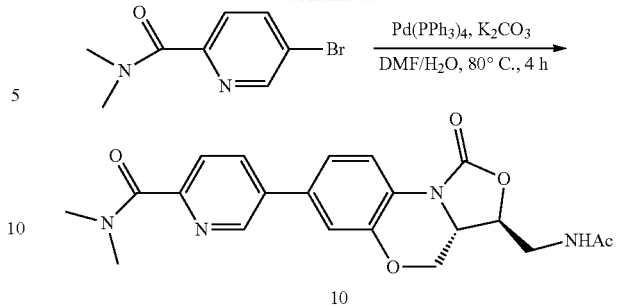

Compound II-3 (233 mg, 0.6 mmol) is dissolved in DMF/H₂O (7:1, 8 mL), potassium carbonate (414 mg, 3 mmol), 5-bromo-N,N-dimethylpicolinamide (183 mg, 0.8 mmol) (WO2005014571), Pd(PPh₃)₄ (92 mg, 0.06 mmol) are added, and follow the method described in example 1 to obtain 35 mg of white foamy solid (Compound 10). The yield is 14.0%.

¹H NMR (300 MHz, CDCl₃): δ 8.78 (s, 1 H), 8.12 (d, J=8.30 Hz, 1 H), 7.98 (dd, J₁=1.95 Hz, J₂=8.06 Hz, 1 H), 7.73 (d, J=8.06 Hz, 1 H), 7.20 7.30 (m, 2 H), 6.26 (t, J=6.13 Hz, 1 H), 4.60 (dd, J₁=2.69 Hz, J₂=10.26 Hz 1 H), 4.46 (m, 1 H), 4.05 (m, 1 H), 3.96 (t, J=10.01 Hz, 1 H), 3.85 (m, 2 H), 3.17 (s, 3 H), 3.15 (s, 3 H), 2.06 (s, 3 H). MS (ESI) m/z: 411.2 (M+1)⁺.

Example 12

N-(((3S,3aS)-7-(6-(1-cyano-cyclopropyl)pyridin-3-yl)-1-oxo-1,3,3a,4-tetrahydrobenzo[b]oxazole-[3,4-d][1,4]oxazin-3-yl)methyl)acetamide(11)

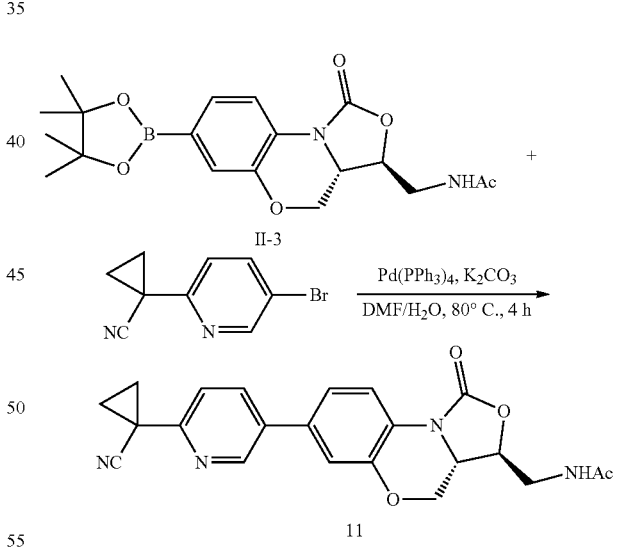

Compound II-3 (233 mg, 0.6 mmol) is dissolved in DMF/H₂O (7:1, 8 mL), potassium carbonate (414 mg, 3 mmol), 2-(1-cyano-cyclopropyl)-5-bromopyridine (178 mg, 0.8 mmol) (J. Org. Chem., 70, 2005, 10186-10189), Pd(PPh₃)₄ (92 mg, 0.06 mmol) are added, and follow the method described in example 1 to obtain 52 mg of product 11 (white foamy solid). The yield is 21.5%.

¹H NMR (300 MHz, CDCl₃): δ 8.95 (m, 1 H), 8.16 (d, J=8.16 Hz, 1 H), 7.96 (dd, J₁=2.18 Hz, J₂=8.35 Hz, 1 H), 7.76 (dd, J₁=0.81 Hz, J₂=8.21 Hz, 1 H), 7.23 (m, 2 H), 6.17 (t, J=6.16 Hz, 1 H), 4.61 (dd, J₁=2.64 Hz, J₂=10.06 Hz, 1 H), 4.48 (m, 1 H), 4.05 (dd, J$_1$=2.63 Hz, J$_2$=7.02 Hz, 1 H), 3.95 (t, J=10.02 Hz, 1 H), 3.78 (m, 2 H), 2.05 (s, 3 H), 0.71 (m, 2 H), 0.95 (m, 2 H). MS (ESI) m/z: 405.2 (M+1)$^+$.

Example 13

N(((3S,3aS)-1-oxo-7-(pyridin-3-yl)-1,3,3a,4-tetrahydrobenzo[b]oxazole[3,4-d][1,4]oxazin-3-yl)methyl)acetamide (12)

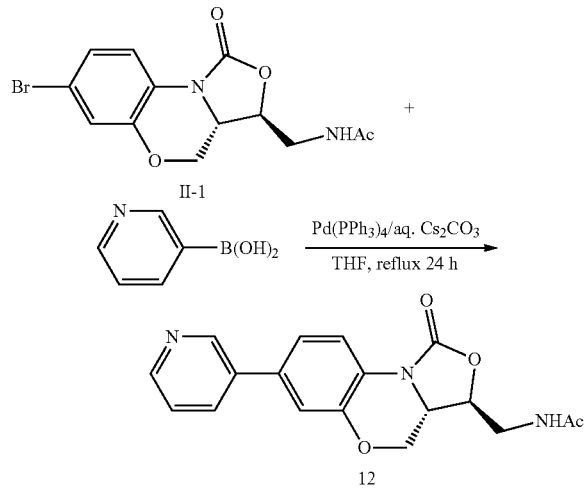

Compound II-1 (341 mg, 1 mmol) is dissolved in THF (20 mL), 2N cesium carbonate solution (1 mL, 2 mmol), 3-pyridinylboronic acid (184 mg, 1.5 mmol) (purchased from Sigma-Aldrich Co.) and Pd(PPh$_3$)$_4$ (120 mg, 0.1 mmol) are added, and follow the method described in example 1 to obtain 278 mg of white solid (Compound 12). The yield is 82.0%.

$^1$H NMR (300 MHz, CDCl$_3$): δ 8.79 (d, J=2.06 Hz, 1 H), 8.57 (dd, J$_1$=1.39 Hz, J$_2$=4.77 Hz, 1 H), 8.08 (d, J=8.36 Hz, 1H), 7.82 (m, 1 H), 7.35 (dd, J$_1$=4.77 Hz, J$_2$=7.91 Hz, 1 H), 7.16-7.22 (m, 2 H), 6.36 (t, J=6.23 Hz, 1 H), 4.59 (dd, J$_1$=2.49 Hz, J$_2$=9.96 Hz, 1 H), 4.45 (m, 1 H), 3.90-4.05 (m, 2 H), 3.70-3.80 (m, 2 H), 2.06 (s, 3 H). MS (EI) m/z (%): 339 (M$^+$, 43), 211 (100).

Example 14

N(((3S,3aS)-1-oxo-7-(pyridin-4-yl)-1,3,3a,4-tetrahydrobenzo[b]oxazole[3,4-d][1,4]oxazin-3-yl)methyl)acetamide (13)

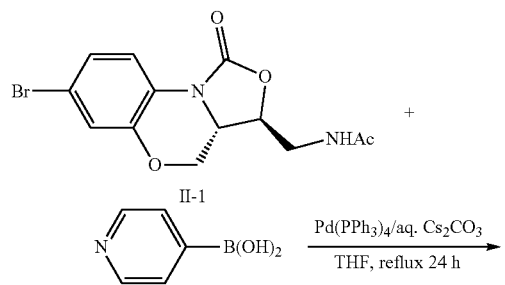

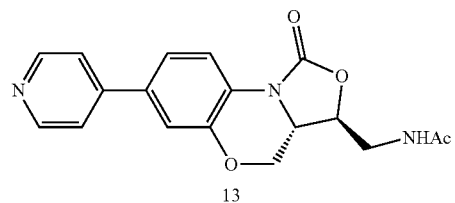

Compound II-1 (341 mg, 1 mmol) is dissolved in THF (20 mL), 2N cesium carbonate solution (1 mL, 2 mmol), 4-pyridinylboronic acid (184 mg, 1.5 mmol) (purchased from Sigma-Aldrich Co.) and Pd(PPh$_3$)$_4$ (120 mg, 0.1 mmol) are added, and follow the method described in example 1 to obtain 281 mg of white solid (Compound 13). The yield is 82.9%.

$^1$H NMR (300 MHz, CDCl$_3$): δ 8.64 (dd, J$_1$=1.47 Hz, J$_2$=4.70 Hz, 2 H), 8.12 (d, J=8.50 Hz, 1 H), 7.46 (dd, J$_1$=1.47 Hz, J$_2$=4.70 Hz, 2 H), 7.12-7.26 (m, 2 H), 6.06 (t, J=6.23 Hz, 1 H), 4.59 (dd, J$_1$=2.64 Hz, J$_2$=9.97 Hz, 1 H), 4.45 (m, 1 H), 3.90-4.05 (m, 2 H), 3.70-3.82 (m, 2 H), 2.06 (s, 3 H). MS (EI) m/z (%): 339 (M$^+$, 28), 211 (100).

Example 15

N(((3S,3aS)-1-oxo-7-(6-nitropyridin-3-yl)-1,3,3a,4-tetrahydrobenzo[b]oxazole[3,4-d][1,4]oxazin-3-yl)methyl)acetamide (14)

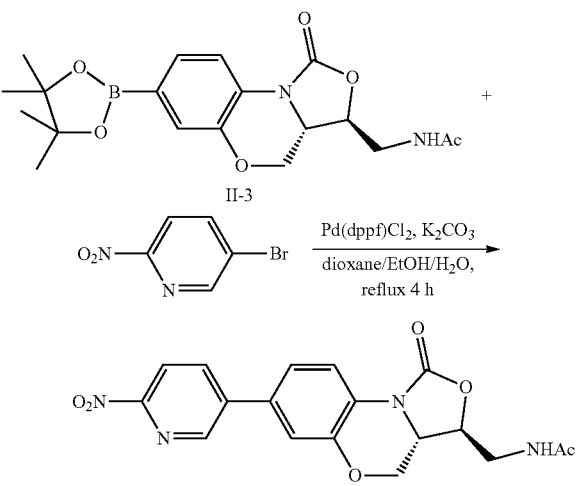

Compound II-3 (388 mg, 1 mmol) and 2-nitro-5-bromopyridine (purchased from Sigma-Aldrich Co.) (244 mg, 1.2 mmol) are dissolved in 1,4-dioxane (10 mL), ethanol (3 mL) and water (3 mL), add K$_2$CO$_3$ (405 mg, 3 mmol), replace with nitrogen, and then add Pd(dppf)Cl$_2$ (50 mg, 0.06 mmol). Follow the method described in example 9 to obtain 80 mg of yellow foamy solid (Compound 14). The yield is 20.8%.

$^1$H NMR (300 MHz, CDCl$_3$): δ 8.81 (t, J=2.05 Hz, 1 H), 8.33 (d, J=8.21 Hz, 1 H), 8.20 (d, J=8.40 Hz, 1 H), 8.15 (dd, J$_1$=2.10 Hz, J$_2$=8.40 Hz, 1 H), 7.20-7.30 (m, 2 H), 5.96 (br s,

1 H), 4.65 (m, 1 H), 4.46 (m, 1 H), 3.90-4.10 (m, 2 H), 3.85 (m, 2 H), 2.06 (s, 3 H). MS (ESI) m/z: 385.1 (M+1)⁺.

Example 16

N(((3S,3aS)-8-fluoro-1-oxo-7-(pyridin-3-yl)-1,3,3a,4-tetrahydrobenzo[b]oxazole[3,4-d][1,4]oxazin-3-yl)methyl)acetamide (15)

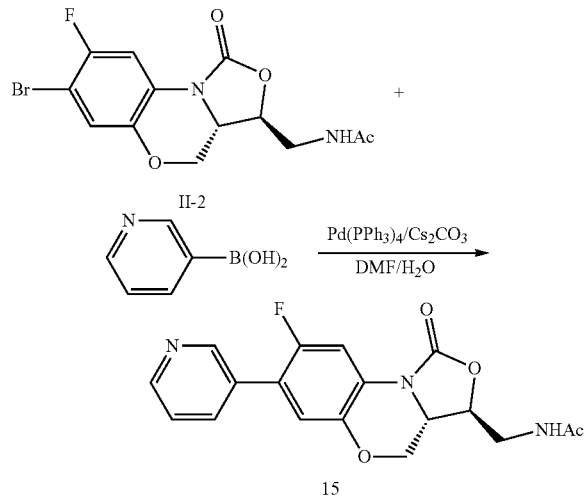

Compound II-2 (359 mg, 1 mmol) is dissolved in a mixed solvent of DMF (14 mL) and water (2 mL), cesium carbonate (652 mg, 2 mmol), 3-pyridinylboronic acid (184 mg, 1.5 mmol) (purchased from Sigma-Aldrich Co.) and Pd (PPh₃)₄ (120 mg, 0.1 mmol) are added, and follow the method described in example 1 to obtain 268 mg of white solid (Compound 15). The yield is 75.1%.

¹H NMR (300 MHz, CDCl₃): δ 8.73 (s, 1 H), 8.58 (d, J=3.44 Hz, 1 H), 7.90 (m, 2 H), 7.42 (m, 1 H), 7.06 (d, J=7.01 Hz, 1 H), 6.26 (t, J=6.13 Hz, 1 H), 4.59 (dd. J₁=2.45 Hz, J₂=10.06 Hz, 1 H), 4.42 (m, 1 H), 3.90-4.05 (m, 1 H), 3.86 (t, J=10.15 Hz, 1 H), 3.70-3.80 (m, 2 H), 2.06 (s, 3 H). MS (ESI) m/z (%): 358.2 (M+1)⁺.

Example 17

N(((3S,3a S)-8-oxo-1-oxo-7-(pyridin-4-yl)-1,3,3a,4-tetrahydrobenzo[b]oxazole[3,4-d][1,4]oxazin-3-yl)methyl)acetamide (16)

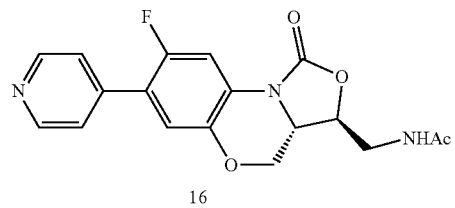

Compound II-2 (359 mg, 1 mmol) is dissolved in a mixed solvent of DMF (14 nit) and water (2 mL), cesium carbonate (652 mg, 2 mmol), 4-pyridinylboronic acid (184 mg, 1.5 mmol) (purchased from Sigma-Aldrich Co.) and Pd (PPh₃)₄ (120 mg, 0.1 mmol) are added, and follow the method described in example 1 to obtain 272 mg of white solid (Compound 16). The yield is 76.2%.

¹H NMR (300 MHz, CDCl₃): δ 8.62 (d, J=8.50 Hz, 2 H), 8.12 (d, J=8.52 Hz, 2 H), 7.45 (m, 1 H), 7.06 (d, J=7.01 Hz, 1 H), 6.23 (t, J=6.13 Hz, 1 H), 4.58 (dd, J₁=2.45 Hz, J₂=10.03 Hz, 1 H), 4.42 (m, 1 H), 3.90-4.05 (m, 1 H), 3.86 (t, J=10.12 Hz, 1 H), 3.70-3.80 (m, 2 H), 2.05 (s, 3 H). MS (ESI) m/z (%): 358.2 (M+1)⁺.

Example 18

N(((3S,3aS)-8-fluoro-1-oxo-7-(pyrimidin-5-yl)-1,3,3a,4-tetrahydrobenzo[b]oxazole[3,4-d][1,4]oxazin-3-yl-methyl)acetamide (17)

Compound II-2 (287 mg, 0.8 mmol) is dissolved in a mixed solvent of DMF (14 mL) and water (2 mL), cesium carbonate (652 mg, 2 mmol), 3-pyridinylboronic acid (124 mg, 1 mmol) (purchased from Sigma-Aldrich Co.) and Pd (PPh₃)₄ (70 mg, 0.06 mmol) are added, and follow the method described in example 1 to obtain 207 mg of white solid (Compound 17). The yield is 72.4%.

¹H NMR (300 MHz, CDCl₃): δ 9.12 (s, 1 H), 8.92 (s, 2 H), 7.45 (m, 1 H), 7.02 (d, J=7.06 Hz, 1 H), 6.23 (t, J=6.16 Hz, 1 H), 4.60 (dd, J₁=2.45 Hz, J₂=10.05 Hz, 1 H), 4.42 (m, 1 H), 3.92-4.05 (m, 1 H), 3.88 (t, J=10.08 Hz, 1 H), 3.70-3.78 (m, 2 H), 2.05 (s, 3 H). MS (ESI) m/z (%): 359.2 (M+1)⁺.

Example 19

N(((3S,3aS)-8-fluoro-1-oxo-7-(6-cyanopyridin-3-yl)-1,3,3a,4-tetrahydrobenzo[b]oxazole[3,4-d][1,4]oxazin-3-yl)methyl)acetamide (18)

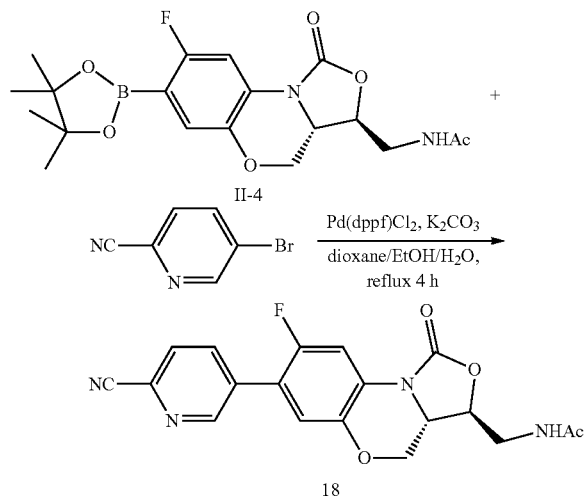

Compound II-4 (244 mg, 0.6 mmol) and 6-cyano-3-bromopyridine (128 mg, 0.7 mmol) (Bioorg. Med. Chem., 12, 2004, 5909-5915) are dissolved in 1,4-dioxane (10 mL), ethanol (3 mL) and water (3 mL), add K₂CO₃ (207 mg, 1.5 mmol), replace with nitrogen, and then add Pd(dppf)Cl₂ (30 mg, 0.036 mmol). Follow the method described in example 9 to obtain 129 mg of white solid (Compound 18). The yield is 56.3%.

¹H H NMR (300 MHz, CDCl₃): δ 8.90 (d, J=0.80 Hz, 1 H), 8.16 (d, J=8.21 Hz, 1 H), 7.76 (dd, J₁=0.80 Hz, J₂=8.21 Hz, 1 H), 7.45 (m, 1 H), 7.02 (d, J=7.03 Hz, 1 H), 6.17 (t, J=6.23 Hz, 1 H), 4.58 (dd, J₁=2.43 Hz, J₂=10.06 Hz, 1 H), 4.42 (m, 1 H), 3.95-4.02 (m, 1 H), 3.86 (t, J=10.05 Hz, 1 H), 3.70-3.82 (m, 2 H), 2.06 (s, 3 H). MS (ESI) m/z: 383.2 (M+1)⁺.

Example 20

N(((3S,3aS)-8-fluoro-1-oxo-7-(6-(1-methyl-1H-tetrazol-5-yl)pyridin-3-yl)-1,3,3a,4-tetrahydrobenzo[b]oxazole[3,4-d][1,4]oxazin-3-yl)methyl)acetamide (19)

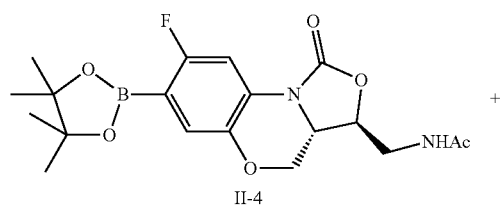

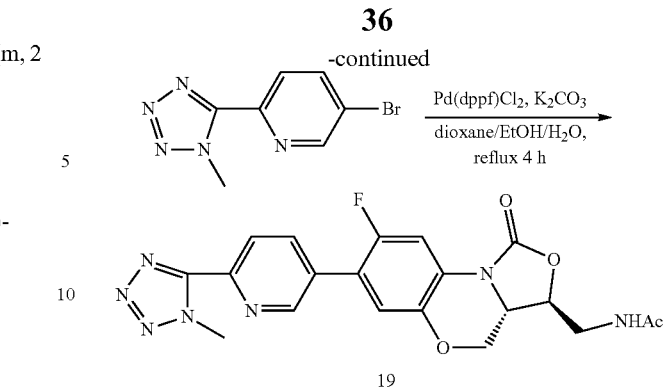

Compound II-4 (203 mg, 0.5 mmol) and 5-bromo-2-(1-methyl-2H-tetrazol-5-yl)pyridine (120 mg, 0.5 mmol) (Bioorg. Med. Chem., 12, 2004, 5909-5915) are dissolved in 1,4-dioxane (10 mL), ethanol (3 mL) and water (3 mL), add K₂CO₃ (207 mg, 1.5 mmol), replace with nitrogen, and then add Pd (dppf) Cl₂ (30 mg, 0.036 mmol). Follow the method described in example 9 to obtain 87 mg of foamy solid (Compound 19). The yield is 39.5%.

¹H NMR (300 MHz, CDCl₃): δ 8.99 (s, 1 H), 8.33 (d, J=6.62 Hz, 1 H), 8.14 (d, J=8.21 Hz, 1 H), 7.54 (m, 1 H), 7.06 (d, J=7.01 Hz, 1 H), 6.22 (t, J=6.13 Hz, 1 H), 4.58 (dd, J₁=2.47 Hz, J₂=10.06 Hz, 1 H), 4.42 (m, 1 H), 3.96-4.02 (m, 1 H), 3.86 (t, J=10.08 Hz, 1 H), 3.72-3.82 (m, 2 H), 2.05 (s, 3 H). MS (ESI) m/z: 440.2 (M+1)⁺.

Example 21

N(((3S,3aS)-1-oxo-7-(6-aminopyridin-3-yl)-1,3,3a,4-tetrahydrobenzo[b]oxazole[3,4-d][1,4]oxazin-3-yl)methyl)acetamide (20)

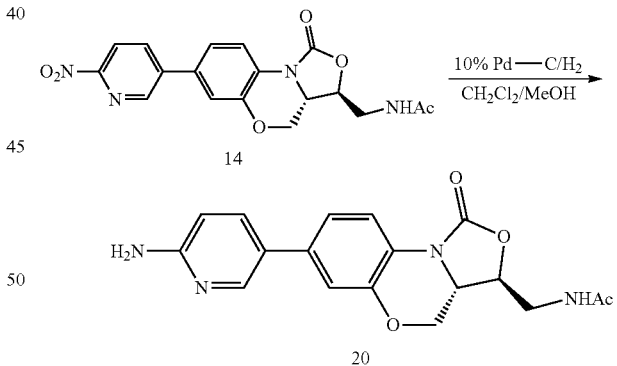

Compound 14 (112 mg, 0.29 mmol) is dissolved in a mixed solvent of dichloromethane (20 mL) and methanol (20 mL), add 10% Pd—C (50 mg), then allow hydrogenation reaction at normal pressure and temperature overnight. TLC (CH₂Cl₂/MeOH=20:1) is used to monitor the reaction. After the reaction is completed, conduct filtering, and the residue is washed with a small amount of dichloromethane, then the filtrate is concentrated and undergoes column chromatography (CH₂Cl₂/MeOH=20:1), to obtain 65 mg of white powdery solid product (Compound 20). The yield is 63%.

¹H NMR (300 MHz, DMSO-d₆): δ 8.29 (t, J=5.61 Hz, 1 H), 8.21 (s, 1 H), 7.89 (dd, J₁=2.44 Hz, J₂=8.24 Hz, 1 H), 7.70 (m,

1 H), 7.16-7.25 (m, 2 H), 6.52 (t, J=8.79 Hz, 1 H), 4.44-4.56 (m, 2 H), 3.95-4.08 (m, 2 H), 3.48-3.62 (m, 2 H), 1.86 (s, 3 H). MS (ESI) m/z: 355.3 (M+1)+.

Example 22

N-(((3S,3aS)-7-(4-methylpyrazol-1-yl)-1-oxo-1,3,3a,4-tetrahydrobenzo[b]oxazole[3,4-d][1,4]oxazin-3-yl)methyl)acetamide (21)

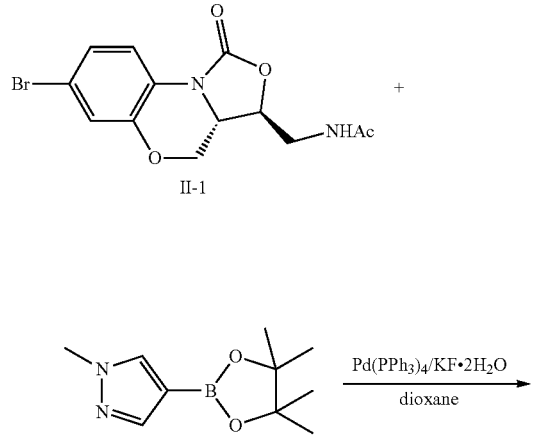

Compound II-1 (100 mg, 0.293 mmol) is dissolved in 1,4-dioxane (6 mL), and potassium fluoride dihydrate KF.2H$_2$O (55.2 mg, 0.59 mmol), 1-methylpyrazol-4-boronic acid pinacol ester (91.4 mg, 0.44 mmol) (purchased from Sigma-Aldrich Co.) and Pd (PPh$_3$)$_4$ (33.8 mg, 0.03 mmol) are added, then heat to 80° C. and allow reaction under the protection of argon for 24 hours. TLC (petroleum ether/acetone=1:1) is used to monitor the reaction. After the reaction is completed, the solvent is distilled off, then add chloroform (50 mL) to dissolve the residue, followed by wash with water (20 mL), and saturated sodium chloride solution (30 mL) successively, drying with anhydrous sodium sulfate, and column chromatography (petroleum ether/acetone=1:1) to obtain 20 mg of a white powdery solid (Compound 21). The yield is 20%.

$^1$H NMR (300 MHz, CDCl$_3$): δ 7.97 (d, J=8.55 Hz, 1 H), 7.74 (d, J=0.73 Hz, 1 H), 7.58 (s, 1 H), 7.10 (dd, J$_1$=8.55 Hz, J$_2$=1.95 Hz, 1 H), 7.05 (s, 1 H), 6.04 (t, 1 H), 4.55 (dd, J$_1$=9.97 Hz, J$_2$=2.93 Hz, 1 H), 4.38-4.46 (m, 1 H), 4.10-4.15 (m, 1 H), 3.83-4.00 (m, 4H), 3.65-3.80 (m, 2 H), 2.02 (s, 3 H). MS (EI) m/z (%): 214 (100), 342 (M+, 99).

Example 23

N(((3S,3aS)-7-(4H-pyrazol-1-yl)-1-oxo-1,3,3a,4-tetrahydrobenzo[b]oxazole[3,4-d][1,4]oxazin-3-yl)methyl)acetamide (22)

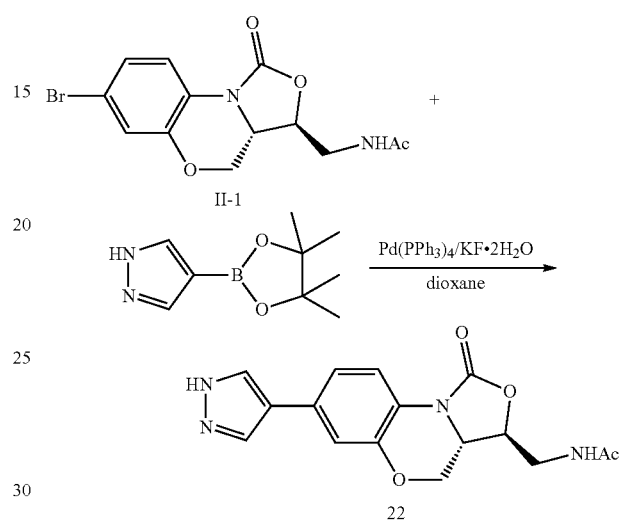

Compound II-1 (100 mg, 0.293 mmol) is dissolved in 1,4-dioxane (6 mL), and potassium fluoride dihydrate (55.2 mg, 0.59 mmol), 1H-pyrazol-4-boronic acid pinacol ester (85.4 mg, 0.44 mmol) (purchased from Sigma-Aldrich Co.) and Pd(PPh$_3$)$_4$ (33.8 mg, 0.03 mmol) are added. Follow the method described in example 22 to obtain 26.1 mg of white solid (Compound 22). The yield is 27%.

$^1$H NMR (300 MHz, DMSO-d$_6$): δ 7.90 (d, J=8.21 Hz, 1 H), 7.81 (t, 1 H), 7.75 (s, 1 H), 7.01-7.08 (m, 2 H), 4.55 (dd, J$_1$=9.97 Hz, J$_2$=2.93 Hz, 1 H), 4.38-4.46 (m, 1 H), 4.10-4.15 (m, 1 H), 3.83-4.00 (m, 1 H), 3.65-3.80 (m, 2 H), 2.02 (s, 3 H). MS (EI) m/z (%): 328 (M+, 100).

Example 24

N(((3S,3aS)-7-(6-methoxypyridin-3-yl)-1-oxo-1,3,3a,4-tetrahydrobenzo[b]oxazole[3,4-d][1,4]oxazin-3-yl)methyl)acetamide (23)

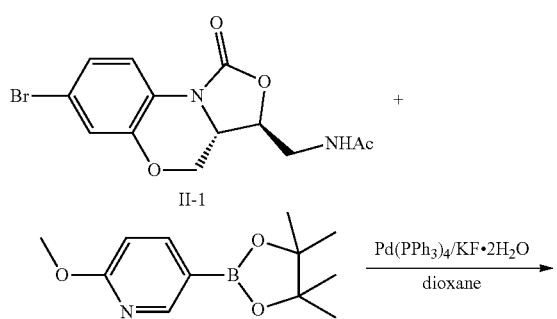

-continued

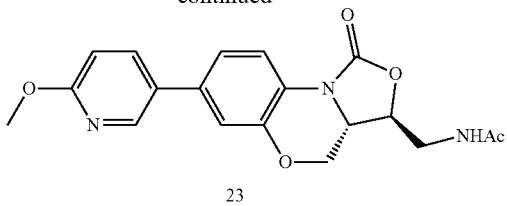

23

Compound II-1 (100 mg, 0.293 mmol) is dissolved in 1,4-dioxane (6 mL), and potassium fluoride dihydrate (55.2 mg, 0.59 mmol), 2-methoxypyridin-5-boronic acid pinacol ester (103.4 mg, 0.44 mmol) (purchased from Sigma-Aldrich Co.) and Pd(PPh$_3$)$_4$ (33.8 mg, 0.03 mmol) are added. Follow the method described in example 22 to obtain 33 mg of white solid (Compound 23). The yield is 30.5%.

$^1$H NMR (300 MHz, CDCl$_3$): δ 8.35 (d, J=2.44 Hz, 1 H), 8.05 (d, J=8.50 Hz, 1 H), 7.74 (dd, J$_1$=2.35 Hz, J$_2$=8.51 Hz, 1 H), 7.16 (td, J$_1$=1.76 Hz, J$_2$=8.50 Hz, 2 H), 6.80 (d, J=8.80 Hz, 1 H), 6.10 (t, J=6.15 Hz, 1 H), 4.58 (dd, J$_1$=2.34 Hz, J$_2$=9.68 Hz, 1 H), 4.40-4.48 (m, 1 H), 3.90-4.03 (m, 5H), 3.68-3.78 (m, 2 H), 2.05 (s, 3 H). MS (EI) m/z (%):369 (M$^+$, 100).

Example 25

N(((3S,3aS)-7-(6-fluoropyridin-3-yl)-1-oxo-1,3,3a,4-tetrahydrobenzo[b]oxazole[3,4-d][1,4]oxazin-3-yl)methyl)acetamide (24)

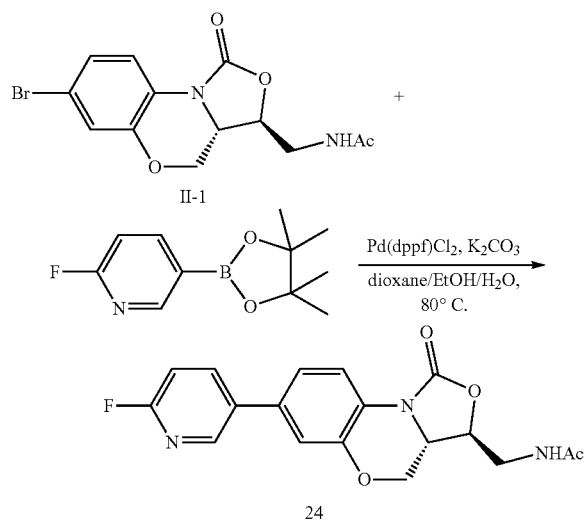

Compound II-1 (100 mg, 0.293 mmol) is dissolved in a mixed solvent of 1,4-dioxane/ethanol/water=3/1/1 (10 mL), and potassium carbonate (80.9 mg, 0.59 mmol), 2-fluoropyridin-5-boronic acid pinacol ester (98.1 mg, 0.44 mmol) (purchased from Sigma-Aldrich Co.) and Pd(dppf)Cl$_2$ (12 mg, 0.015 mmol) are added. Follow the method described in example 9 to obtain 45.9 mg of white solid (Compound 24). The yield is 43.8%.

$^1$H NMR (300 MHz, CDCl$_3$): δ 8.39 (dd, J$_1$=0.92 Hz, J$_2$=1.83 Hz, 1 H), 8.10 (d, J=8.43 Hz, 1 H), 7.96 (t, J=7.51 Hz, 1 H), 7.18 (dd, J$_1$=2.02 Hz, J$_2$=8.44 Hz, 1 H), 7.14 (d, J=1.83 Hz, 1 H), 6.99 (d, J=8.43 Hz, 1 H), 6.05 (t, J=6.15 Hz, 1H), 4.60 (d, J=10.26 Hz, 1 H), 4.45 (m, 1 H), 3.90-4.05 (m, 2 H), 3.70-3.80 (m, 2 H), 2.05 (s, 3 H), 1.58 (s, 6 H). MS (EI) m/z (%): 357 (M$^+$, 100).

Example 26

N(((3S,3aS)-7-(6-(acetyl)aminopyridin-3-yl)-1-oxo-1,3,3a,4-tetrahydrobenzo[b]oxazole[3,4-d][1,4]oxazin-3-yl)methyl)acetamide (25)

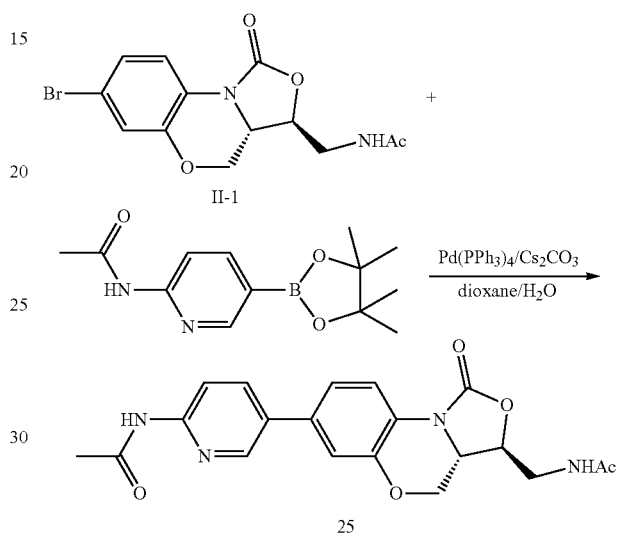

Compound II-1 (200 mg, 0.8 mmol) is dissolved in a mixed solvent of 1,4-dioxane (15 mL) and water (1 mL), and cesium carbonate (381.9 mg, 1.17 mmol), 2-N-acetylaminopyridin-5-boronic acid pinacol ester (184.4 mg, 0.7 mmol) (purchased from Sigma-Aldrich Co.) and Pd(PPh$_3$)$_4$ (67.7 mg, 0.058 mmol) are added. Follow the method described in example 22 to obtain 82 mg of white solid (Compound 25). The yield is 35.3%.

$^1$H H NMR (300 MHz, DMSO-d$_6$): δ 10.59 (s, 1 H), 8.62 (d, J=2.20 Hz, 1 H), 8.32 (t, 1 H), 8.05-8.18 (m, 2 H), 7.97 (d, J=8.29 Hz, 1 H), 7.37 (d, J=10.00 Hz, 2 H), 4.58 (d, J=7.56 Hz, 1 H), 4.50 (m, 1 H), 3.50-3.58 (m, 2 H), 2.10 (s, 3 H), 1.87 (s, 3 H). MS (EI) m/z (%):396 (M$^+$, 100)

Example 27

N(((3S,3aS)-7-(2,6-dimethoxy pyrimidine-3-yl)-1-oxo-1,3,3a,4-tetrahydrobenzo[b]oxazole[3,4-d][1,4]oxazin-3-yl)methyl)acetamide (26)

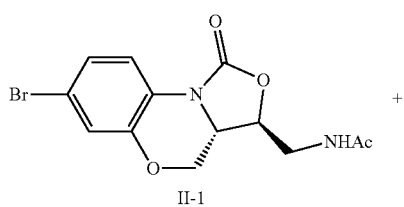

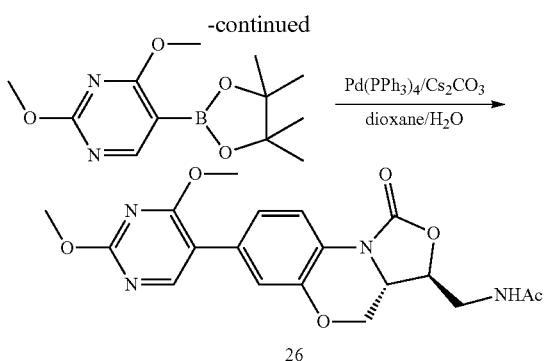

Compound II-1 (120 mg, 0.35 mmol) is dissolved in a mixed solvent of 1,4-dioxane (10 mL) and water (1 mL), and cesium carbonate (228 mg, 0.7 mmol), 2,6-dimethoxy pyrimidine-5-boronic acid pinacol ester (112.3 mg, 0.42 mmol) (purchased from Sigma-Aldrich Co.) and Pd(PPh$_3$)$_4$ (40.4 mg, 0.035 mmol) are added, then heat to 80° C. and allow reaction under the protection of argon for 2 hours. TLC (petroleum ether/acetone=1:1) is used to monitor the reaction. After the reaction is completed, stop the reaction, the solvent is distilled off, then add chloroform (50 mL) to dissolve the residue, followed by wash with water (20 mL) and saturated sodium chloride solution (30 mL) successively drying with anhydrous sodium sulfate, and column chromatography (petroleum ether/acetone=1:1) to obtain 96 mg of a white powdery solid (Compound 26). The yield is 68.5%.

$^1$H NMR (300 MHz, CDCl$_3$): δ 8.23 (s, 1 H), 8.05 (d, J=9.03 Hz, 1 H), 7.15 (m, 2H), 6.00 (t, J=7.32 Hz, 1H), 4.60 (d, J=9.51 Hz, 1 H), 4.45 (m, 1 H), 4.05 (s, 6 H), 3.90-4.00 (m, 2 H), 3.70-3.78 (m, 2 H), 2.05 (s, 3 H), MS (EI) m/z (%): 400 (M$^+$, 72), 272 (100).

Example 28

N(((3S,3aS)-7-(6-(piperazin-1-yl)pyridin-3-yl)-1-oxo-1,3,3a,4-tetrahydrobenzo[b]oxazole[3,4-d][1,4]oxazin-3-yl)methyl)acetamide (27)

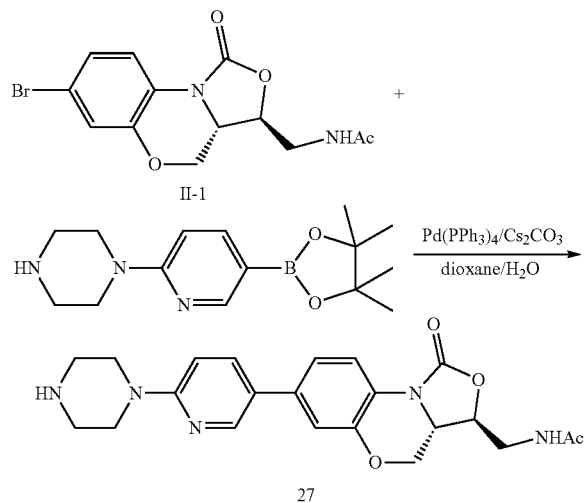

Compound II-1 (120 mg, 0.35 mmol) is dissolved in a mixed solvent of 1,4-dioxane (10 mL) and water (1 mL), and cesium carbonate (228 mg. 0.7 mmol), 2-(piperazin-1-yl)pyridin-5-boronic acid pinacol ester (112.3 mg, 0.42 mmol) (purchased from Sigma-Aldrich Co.) and Pd(PPh$_3$)$_4$ (40.4 mg, 0.035 mmol) are added, then heat to 80° C. and allow reaction under the protection of argon for 15 hours. TLC (petroleum ether/acetone=1:1) is used to monitor the reaction. After the reaction is completed, the solvent is distilled off, then add chloroform (50 mL) to dissolve the residue, followed by wash with water (20 mL) and saturated sodium chloride solution (30mL), successively, drying with anhydrous sodium sulfate, and column chromatography (CH$_2$Cl$_2$/MeOH=10:1) to obtain 29.4 mg of white powdery solid (Compound 27). The yield is 19.7%.

$^1$H NMR (300 MHz, DMSO-d$_6$): δ 8.50 (d, J=2.44 Hz, 1 H), 8.32 (t, 1 H), 7.96 (dd, J$_1$=2.92 Hz, J$_2$=5.37 Hz, 1 H), 7.93 (d, J=2.44 Hz, 1 H), 7.32 (d, J=1.95 Hz, 1 H), 7.26 (s, 1H), 6.99 (d, J=9.78 Hz, 1 H), 4.55 (d, J=7.31 Hz, 1 H), 4.50 (d, J=6.32 Hz, 1 H), 3.95-4.10 (m, 2 H), 3.85 (t, J=4.88 Hz, 4 H), 3.48-3.60 (m, 2 H), 3.25 (t, 4.88 Hz, 4 H), 2.05 (s, 3 H). MS (EI) m/z (%): 423 (M$^+$, 50), 354 (100).

Example 29

N(((3S,3aS)-7-(6-(2-hydroxypropan-2-yl)pyridin-3-yl)-1-oxo-1,3,3a,4-tetrahydrobenzo[b]oxazole[3,4-d][1,4]oxazin-3-yl)methyl)acetamide (28)

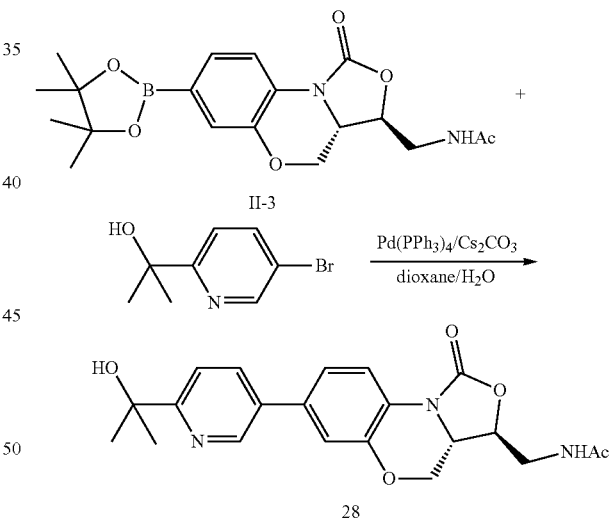

Compound II-1 (150 mg, 0.386 mmol) is dissolved in a mixed solvent of 1,4-dioxane (10 mL) and water (1 mL), and cesium carbonate (251.5 mg, 0.77 mmol), 2-(2-hydroxypropan-2-yl)-5-bromopyridine (100.24 mg, 0.464 mmol) (Tetrahedron Lett., 41,2000, 4335-4338) and Pd(PPh$_3$)$_4$ (44.6 mg, 0.039 mmol) are added. Follow the method described in example 27 to obtain 83.6 mg of white powdery solid (Compound 28). The yield is 54.5%.

$^1$H NMR (300 MHz, CDCl$_3$): δ 8.69 (d, J=2.01 Hz, 1 H), 8.10 (d, J=8.43 Hz, 1 H), 7.85 (dd, J$_1$=2.20 Hz, J$_2$=8.25 Hz, 1 H), 7.43 (d, J=8.24 Hz, 1 H), 7.22 (d, J=6.96 Hz, 1 H), 7.09 (d, J=1.82 Hz, 1H), 6.05(t, J=6.15 Hz, 1H), 4.92 (s, 1 H), 4.60 (d,

J=10.26 Hz, 1 H), 4.45 (m, 1 H), 3.90-4.05 (m, 2 H), 3.70-3.80 (m, 2 H), 2.05 (s, 3 H). MS (EI) m/z (%):397 (Mt 100)

Example 30

N(((3S,3aS)-7-(6-(1-hydroxy-3-methylbutyl)pyridin-3-yl)-1-oxo-1,3,3a,4-tetrahydrobenzo[b]oxazole[3,4-d][1,4]oxazin-3-yl)methyl)acetamide (29)

Step 1, Preparation of 1-(5-bromopyridin-2-yl)-3-methyl-butanol (29-B)

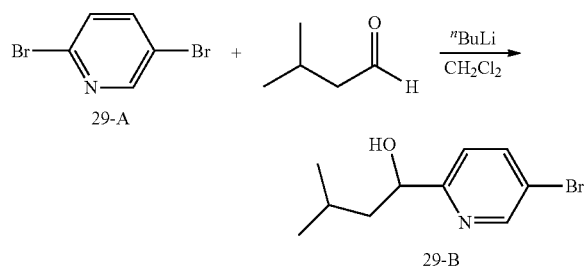

Compound 29-A (2,5-dibromopyridine) (3 g, 12.66 mmol) (purchased from Darui Chemical Technology (Shanghai) Co., Ltd.) is dissolved in dichloromethane (150 mL), and the resultant solution is cooled to −78° C., stir and slowly add dropwise n-butyllithium (2.5 M n-hexane solution) (6.1 mL, 15.2 mmol). When addition is done, maintain it at −78° C., stir for 2 hours, and then added isovaleraldehyde (1.31 g, 15.20 mmol) dropwise, continue stirring at −78° C. for 1 hour. TLC (petroleum ether/ethyl acetate=5:1) is used to monitor the reaction. Once all the raw materials are consumed in the reaction, add saturated ammonium chloride solution (100 mL) into reaction solution, rise to room temperature and stir for 0.5 hours. After that, the organic phase is separated, followed by wash with water (100 mL) and saturated sodium chloride solution (100 mL), successively, drying with anhydrous sodium sulfate, and column chromatography (petroleum ether/ethyl acetate=5:1), to obtain 1.55 g of oily liquid (Compound 29-B). The yield is 50.15%.

$^1$H NMR (300 MHz, CDCl$_3$): δ 8.59 (d, J=2.34 Hz 1 H), 7.78 (dd, J$_1$=2.35 Hz, J$_2$=8.21 Hz, 1 H), 7.18 (d, J=8.21 Hz 1 H), 4.70-4.80 (m, 1 H), 3.60 (d, J=5.86 Hz, 1 H), 1.80-1.95 (m, 1 H), 1.45-1.65 (m, 2 H) 1.00(d, J=6.45 Hz, 3 H), 0.93 (d, J=6.45 Hz, 3 H). MS (EI) m/z (%):230 (M$^+$, 4), 200 (100).

Step 2, Preparation of N(((3S,3aS)-7-(6-(1-hydroxy-3-methylbutyl)pyridin-3-yl)-1-oxo-1,3,3a,4-tetrahydrobenzo[b]oxazole[3,4-d][1,4]oxazin-3-yl)methyl)acetamide (29)

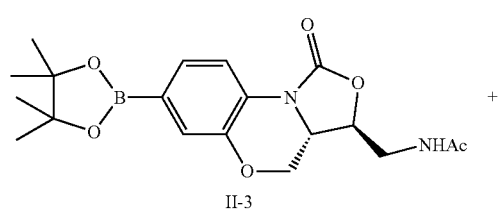

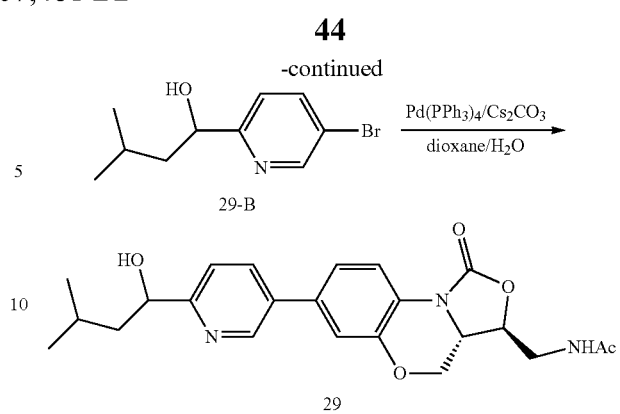

Compound II-3 (100 mg, 0.258 mmol) is dissolved in a mixed solvent of 1,4-dioxane (6 mL) and water (1 mL), and cesium carbonate (168 mg, 0.516 mmol), 29-B (75.5 mg, 0.309 mmol) and Pd(PPh$_3$)$_4$ (29.8 mg, 0.026 mmol) are added. Follow the method described in example 27 to obtain 55.2 mg of white solid (Compound 29). The yield is 50.3%.

$^1$H NMR (300 MHz, CDCl$_3$): δ8.69 (s, 1 H), 8.10 (d, J=8.55 Hz, 1 H), 7.85 (dd, J$_1$=1.52 Hz, J$_2$=6.72 Hz, 1 H), 7.30 (d, J=8.24 Hz, 1 H), 7.16-7.22 (m, 2 H), J=6.10 Hz, 1H), 4.84 (s, 1 H), 4.60 (d, J=7.63 Hz, 1 H), 4.45 (m, 1 H), 3.90-4.05 (m, 2 H), 3.70-3.78 (m, 2 H), 2.05 (s, 3 H), 1.83 (m, 1 H), 1.73 (m, 1 H), 1.03 (d, J=6.72 Hz, 3 H), 0.98 (d, J=6.72 Hz, 3 H); MS (EI) m/z (%): 425 (M$^+$, 7), 369 (100).

Example 31

N(((3S,3aS)-7-(6-(5-methyl-1,2,4-oxazol-3-yl)pyridin-3-yl)-1-oxo-1,3,3a,4-tetrahydrobenzo[b]oxazole[3,4-d][1,4]oxazin-3-yl)methyl)acetamide (30)

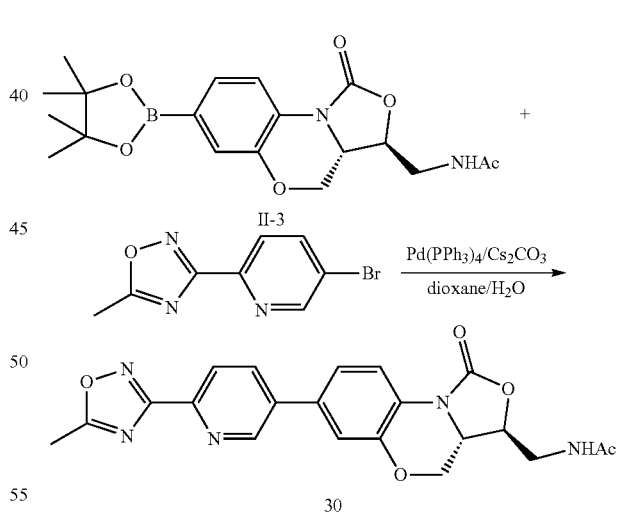

Compound II-3 (120 mg, 0.309 mmol) is dissolved in a mixed solvent of 1,4-dioxane (6 mL) and water (0.5 mL), and cesium carbonate (201.3 mg, 0.62 mmol), 5-bromo-2-(5-methyl-1,2,4-oxazol-3-yl)pyridine (89 mg, 0.37 mmol) (Bioorg. Med. Chem., 12, 2004, 5909-5915) and Pd(PPh$_3$)$_4$ (35.7 mg, 0.03 mmol) are added. Follow the method described in example 27 to obtain 59.2 mg of white solid (Compound 30). The yield is 45.5%.

$^1$H NMR (300 MHz, DMSO-d$_6$): δ 9.08 (d, J=1.46 Hz, 1 H), 8.30 (m. 2 H), 8.12 (d, J=8.29 Hz, 1 H), 8.05 (d, J=9.26

Hz, 1 H), 7.50 (t, 1 H), 4.62 (d, J=7.80 Hz, 1 H), 4.55 (m, 1 H), 4.16-4.01 (m, 2 H), 3.55 (m, 2H), 2.72 (s, 3 H), 1.88 (s, 3 H); MS (EI) m/z (%): 421 (M+, 20), 293 (100)

Example 32

N(((3S,3a S)-7-(6-(2-acetyl)pyridin-3-yl)-1-oxo-1,3,3a,4-tetrahydro benzo[b]oxazole[3,4-d][1,4]oxazin-3-yl)methyl)acetamide (31)

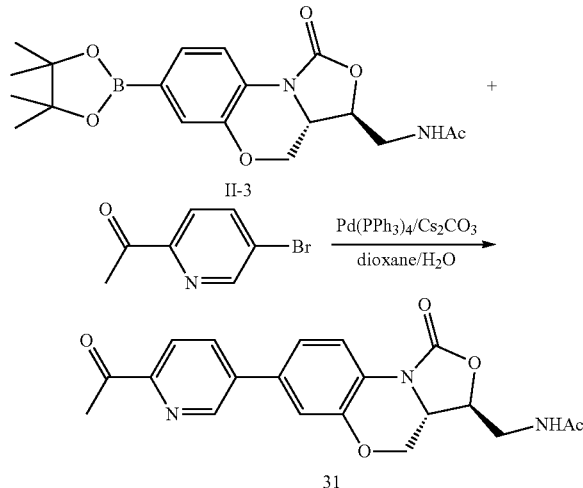

Compound II-3 (120 mg, 0.309 mmol) is dissolved in a mixed solvent of 1,4-dioxane (6 mL) and water (0.5 mL), and cesium carbonate (201.3 mg, 0.62 mmol), 2-acetyl-5-bromopyridine (74 mg, 0.37 mmol) (Bioorg. Med. Chem., 13, 2005, 6763-6770) and Pd(PPh$_3$)$_4$ (35.7 mg, 0.03 mmol) are added. Follow the method described in example 27 to obtain 49.2 mg of white solid (Compound 31). The yield is 41.7%.

$^1$H NMR (300 MHz, DMSO-d$_6$): δ 9.08 (d, J=1.95 Hz, 1 H), 8.32-8.28 (m, 1 H), 8.26 (d, J=2.43 Hz, 1 H), 8.04-7.98 (m, 2 H), 7.50 (m, 2 H), 4.60 (d, J=7.80 Hz, 1 H), 4.55 (m, 1 H), 4.13-4.05 (m, 2 H), 3.58-3.55 (m, 2H), 2.65 (s, 3 H), 1.88 (s, 3 H). MS (EI) m/z (%): 381 (M+, 100)

Example 33

N(((3S,3aS)-7-(2-aminopyrimidin-5-yl)-1-oxo-1,3,3a,4-tetrahydrobenzo[b]oxazole[3,4-d][1,4]oxazin-3-yl)methyl)acetamide (32)

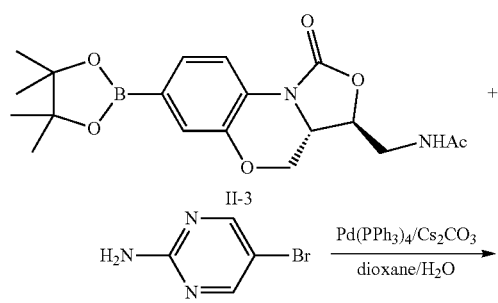

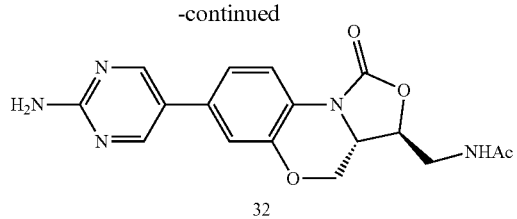

Compound II-3 (120 mg, 0.309 mmol) is dissolved in a mixed solvent of 1,4-dioxane (6 mL) and water (0.5 mL), and cesium carbonate (201.3 mg, 0.62 mmol), 2-amino-5-bromopyridine (64.5 mg, 0.37 mmol) (purchased from J&K CHEMICAL LTD., Shanghai) and Pd(PPh$_3$)$_4$ (35.7 mg, 0.03 mmol) are added. Follow the method described in example 27 to obtain 37.1 mg of white solid (Compound 32). The yield is 33.8%.

$^1$H NMR (300 MHz, DMSO-d$_6$): δ 8.56 (s, 1H), 8.31 (t, 1 H), 7.92 (d, J=9.16 Hz, 1 H), 7.28 (m, 2 H), 4.55 (d, J=7.33 Hz, 1 H), 4.50 (d, J=6.72 Hz, 1 H), 3.95-4.08 (m, 2 H), 3.50-3.58 (m, 2 H), 1.87 (s, 3 H). MS (EI) m/z (%): 355 (M+, 100).

Example 34

N(((3S,3aS)-7-(6-(acetonitrile-2-yl)aminopyridin-3-yl)-1-oxo-1,3,3a,4-tetrahydrobenzo[b]oxazole[3,4-d][1,4]oxazin-3-yl)methyl)acetamide (33)

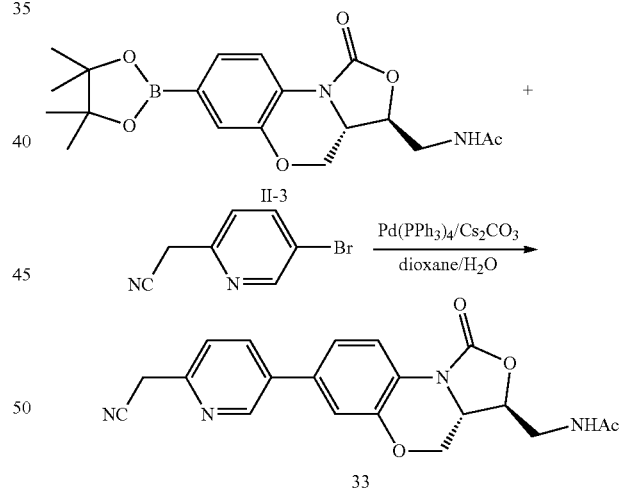

Compound II-3 (100 mg, 0.258 mmol) is dissolved in a mixed solvent of 1,4-dioxane (6 mL) and water (0.5 mL), and cesium carbonate (168 mg, 0.516 mmol), 2-(5-bromopyridin-2-yl)acetonitrile (60.9 mg, 0.309 mmol) (J. Med. Chem. 51, 2008, 6558-6562) and Pd(PPh$_3$)$_4$ (29.8 mg, 0.026 mmol) are added. Follow the method described in example 27 to obtain 62.5 mg of light yellow solid (Compound 33). The yield is 63.5%.

$^1$H NMR (300 MHz, CDCl$_3$): δ 8.79 (d, J=2.02 Hz, 1 H), 8.14 (d, J=8.43 Hz, 1 H), 7.92 (dd, J$_1$=2.38 Hz, J$_2$=8.06 Hz, 1 H), 7.53 (t, J=3.66 Hz, 1 H), 7.21 (td, J$_1$=2.01 Hz, J$_2$=8.43 Hz, 2 H), 5.98 (t, J=6.23 Hz, 1 H), 4.60 (d, J=10.08 Hz, 1 H), 4.45

(m, 1 H), 3.97-4.05 (m, 1 H), 3.95 (t, J=10.08 Hz, 1H) 3.70-3.78 (m, 2 H), 2.05 (s, 3 H). MS (EI) m/z (%): 378 (M+, 40), 250 (100).

Example 35

N(((3S,3aS)-7-(2-cyanopyrimidin-5-yl)-1-oxo-1,3,3a,4-tetrahydrobenzo[b]oxazole[3,4-d][1,4]oxazin-3-yl)methyl)acetamide (34)

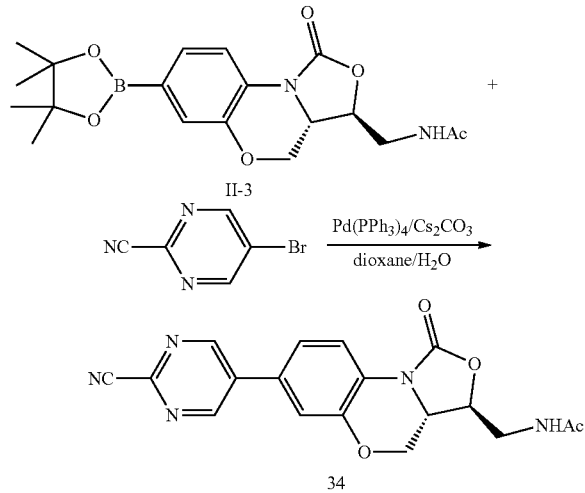

Compound II-3 (100 mg, 0.258 mmol) is dissolved in a mixed solvent of 1,4-dioxane (6 mL) and water (0.5 mL), and cesium carbonate (168 mg, 0.516 mmol), 2-cyano-5-bromopyridine (57 mg, 0.309 mmol) (purchased from J&K CHEMICAL LTD., Shanghai) and Pd(PPh$_3$)$_4$ (29.8 mg, 0.026 mmol) are added. Follow the method described in example 27 to obtain 93.9 mg of white solid (Compound 34). The yield is 98.8%.

$^1$H NMR (300 MHz, DMSO-d$_6$): δ 9.36 (s, 2 H), 8.28 (t, J=5.87 Hz, 1 H), 8.06 (d, J=8.61 Hz, 1 H), 7.55-7.64 (m, 2 H), 4.79 (d, J=7.43 Hz, 1 H)4.53 (m, 1 H), 4.02-4.10 (m, 2 H), 3.50-3.58 (m, 2 H), 1.83 (s, 3 H). MS (EI) m/z (%): 365 (M+, 4), 262 (100).

Example 36

N(((3S,3aS)-7-(6-ethynylpyridin-3-yl)-1-oxo-1,3,3a,4-tetrahydrobenzo[b]oxazole[3,4-d][1,4]oxazin-3-yl)methyl)acetamide (35)

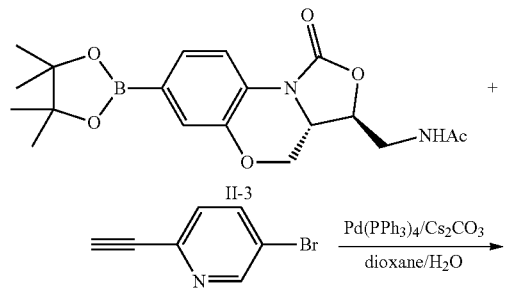

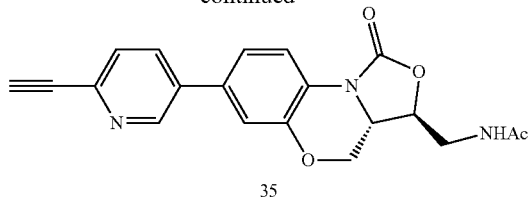

Compound II-3 (100 mg, 0.258 mmol) is dissolved in a mixed solvent of 1,4-dioxane (6 mL) and water (0.5 mL), and cesium carbonate (168 mg, 0.516 mmol), 2-ethynyl-5-bromopyridine (57 mg, 0.309 mmol) (J. Org. Chem., 52, 1988, 386-390) and Pd(PPh$_3$)$_4$ (29.8 mg, 0.026 mmol) are added. Follow the method described in example 27 to obtain 35.1 mg of white solid (Compound 35). The yield is 30%.

$^1$H H NMR (300 MHz, DMSO-d$_6$): δ 8.90 (t, J=0.55 Hz, 1 H), 8.32 (t, 1 H), 8.12 (dd, J$_1$=2.47 Hz, J$_2$=8.25 Hz, 1 H), 8.02 (d, J=9.07 Hz, 1 H), 7.61 (d, J=8.24 Hz, 1 H), 7.40-7.44 (dd, J$_1$=2.20 Hz, J$_2$=6.33 Hz, 2H), 4.58 (d, J=7.15 Hz, 1 H), 4.53 (m, 1 H), 4.39 (s, 1 H), 4.02-4.10 (m, 2 H), 3.48-3.60 (m, 2 H), 1.87 (s, 3 H). MS (EI) m/z (%): 363 (M+, 100).

Example 37

N(((3S,3aS)-7-(6-(3-hydroxyprop-1-ynyl)pyridin-3-yl)-1-oxo-1,3,3a,4-tetrahydrobenzo[b]oxazole[3,4-d][1,4]oxazin-3-yl)methyl)acetamide (36)

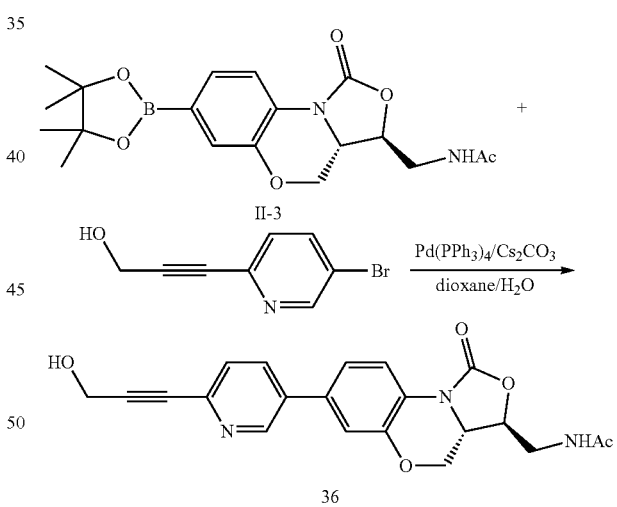

Compound II-3 (100 mg, 0.258 mmol) is dissolved in a mixed solvent of 1,4-dioxane (6 mL) and water (0.5 mL), and cesium carbonate (168 mg, 0.516 mmol), 3-(5-bromopyridin-2-yl)propargyl alcohol (65.5 mg, 0.309 mmol) (J. Org. Chem., 69, 2004, 8723-8730) and Pd(PPh$_3$)$_4$ (29.8 mg, 0.026 mmol) are added. Follow the method described in example 27 to obtain 50.3 mg of white solid (Compound 36). The yield is 41.1%.

$^1$H NMR (300 MHz, DMSO-d$_6$): δ 8.90 (d, J=2.44 Hz, 1 H), 8.30 (t, 1 H), 8.08 (dd, J$_1$=2.43 Hz, J$_2$=10.92 Hz, 1 H), 8.00 (d, J=9.75 Hz, 1 H), 7.58 (d, J=8.29 Hz, 1 H), 7.40 (d, J=6.33 Hz, 2H), 4.60 (d, J=7.31 Hz, 1 H), 4.53 (m, 1 H), 4.37

(s, 2H), 4.02-4.10 (m, 2 H), 3.50-3.58 (m, 2 H), 1.85 (s, 3 H). MS (EI) m/z (%): 393 (M⁺, 100).

Example 38

N(((3S,3aS)-7-(6-trifluoromethylpyridin-3-yl)-1-oxo-1,3,3a,4-tetrahydrobenzo[b]oxazole[3,4-d][1,4]oxazin-3-yl)methyl)acetamide (37)

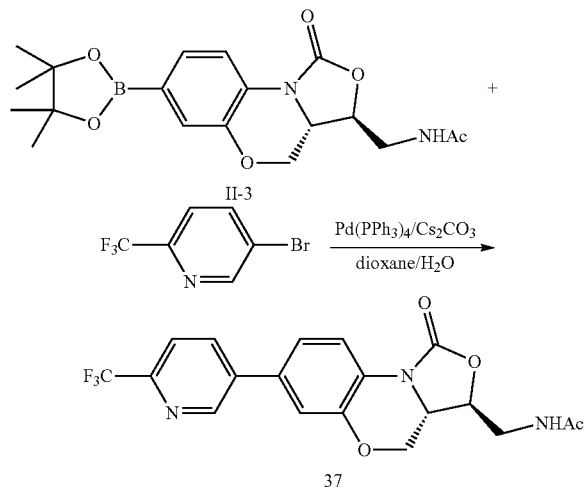

Compound II-3 (120 mg, 0.309 mmol) is dissolved in a mixed solvent of 1,4-dioxane (6 mL) and water (0.5 mL), and cesium carbonate (201.3 mg, 0.62 mmol), 2-trifluoromethyl-5-bromopyridine (83.8 mg, 0.37 mmol) (purchased from J&K CHEMICAL LTD., Shanghai) and Pd(PPh₃)₄ (35.7 mg, 0.03 mmol) are added. Follow the method described in example 27 to obtain 95.1 mg of white solid (Compound 37). The yield is 75%.

¹H NMR (300 MHz, CDCl₃): δ 8.90 (s, 1 H), 8.15 (d, J=8.42 Hz, 1 H), 8.00 (dd, J₁=2.92 Hz, J₂=6.04 Hz, 1 H), 7.75 (d, J=5.67 Hz, 1 H), 7.24 (d, J=6.40 Hz, 1 H), 6.95-7.10 (m, 1H), 6.10 (t, J=6.22 Hz, 1 H), 4.63 (d, J=7.31 Hz, 1 H), 4.50 (m, 1 H), 3.61-4.80 (m, 2 H), 3.48-3.60 (m, 2 H), 2.05 (s, 3 H). MS (EI) m/z (%): 407 (M⁺, 100).

Example 39

N(((3S,3aS)-7-(4-acetylphenyl)-1-oxo-1,3,3a,4-tetrahydrobenzo[b]oxazole[3,4-d][1,4]oxazin-3-yl)methyl)acetamide (38)

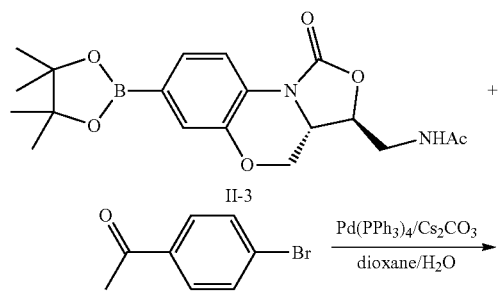

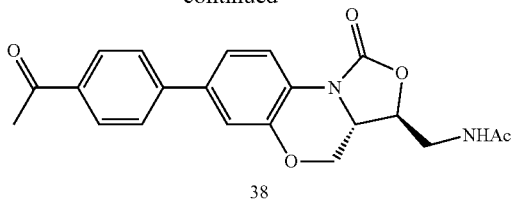

Compound II-3 (120 mg, 0.309 mmol) is dissolved in a mixed solvent of 1,4-dioxane (6 mL) and water (0.5 mL), and cesium carbonate (201.3 mg, 0.62 mmol), p-acetyl bromobenzene (73.8 mg, 0.37 mmol) (purchased from J&K CHEMICAL LTD., Shanghai) and Pd(PPh₃)₄ (35.7 mg, 0.03 mmol) are added. Follow the method described in example 27 to obtain 48.7 mg of white solid (Compound 38). The yield is 41.5%.

¹H NMR (300 MHz, DMSO-d₆): δ 8.33 (t, J=5.81 Hz, 1 H), 8.02 (d, J=7.94 Hz, 3 H), 7.82 (d, J₂=8.25 Hz, 2 H), 7.35-7.50 (m, 2 H), 4.60 (d, J=7.64 Hz, 1 H), 4.50 (dd, J₁=3.97 Hz, J₂=10.69 Hz, 1 H), 4.00-4.10 (m, 2 H), 3.50-3.60 (m, 2 H), 2.60 (s, 3H), 1.85 (s, 3 H). MS (EI) m/z (%): 380 (M⁺, 100).

Example 40

N(((3S,3aS)-7-(2-methylpyridin-4-yl)-1-oxo-1,3,3a,4-tetrahydrobenzo[b]oxazole[3,4-d][1,4]oxazin-3-yl)methyl)acetamide (39)

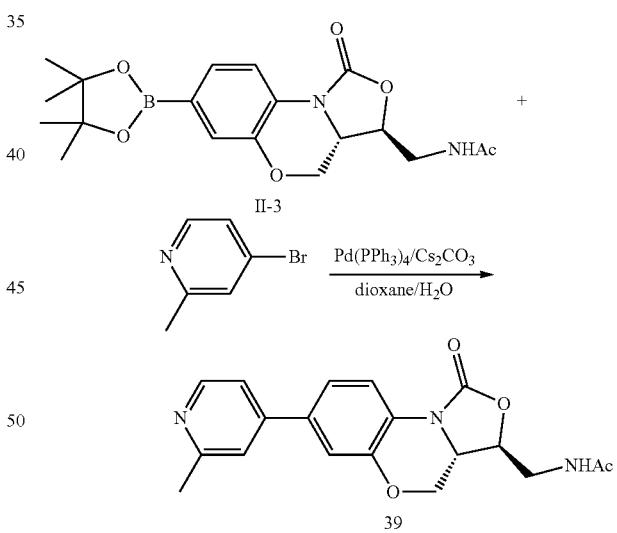

Compound II-3 (120 mg, 0.309 mmol) is dissolved in a mixed solvent of 1,4-dioxane (6 mL) and water (0.5 mL), and cesium carbonate (201.3 mg, 0.62 mmol), 2-methyl-5-bromopyridine (63.6 mg, 0.37 mmol) (purchased from J&K CHEMICAL LTD., Shanghai) and Pd(PPh₃)₄ (35.7 mg, 0.03 mmol) are added. Follow the method described in example 27 to obtain 80 mg of white solid (Compound 39). The yield is 73.3%.

¹H NMR (300 MHz, CDCl₃): δ 8.51 (d, J=5.37 Hz, 1 H), 8.10 (d, J=8.10 Hz, 1 H), 7.20-7.35 (m, 4 H), 6.13 (t, J=6.35 Hz, 1 H), 4.59 (dd, J₁=2.44 Hz, J₂=10.01 Hz, 1 H), 4.45 (m, 1

H), 3.90-4.04 (m, 2 H), 3.60-3.80 (m, 2 H), 2.60 (s, 3H), 2.05 (s, 3 H). MS (EI) m/z (%): 353 (M+, 20), 149 (100).

Example 41

N(((3S,3aS)-7-(6-(1H-1,2,4-triazol-1-yl)pyridin-3-yl)-1-oxo-1,3,3a,4-tetrahydrobenzo[b]oxazole[3,4-d][1,4]oxazin-3-yl)methyl)acetamide (40)

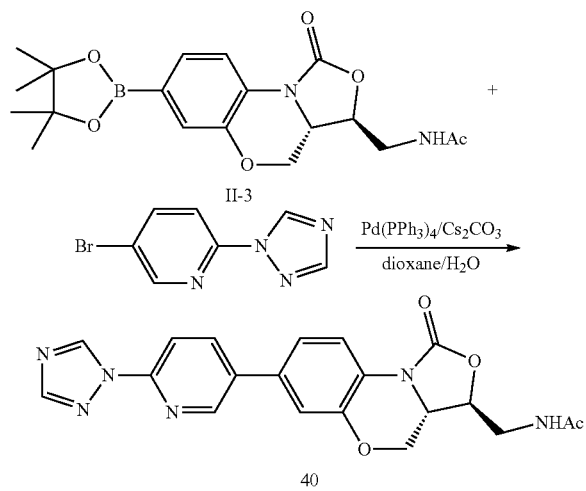

Compound II-3 (120 mg, 0.309 mmol) is dissolved in a mixed solvent of 1,4-dioxane (6 mL) and water (0.5 mL), and cesium carbonate (201.3 mg, 0.62 mmol). 5-bromo-2-(1H-1,2,4-triazol-1-yl)pyridine (83.4 mg, 0.37 mmol) (WO 01/94342) and Pd(PPh$_3$)$_4$ (35.7 mg, 0.03 mmol) are added. Follow the method described in example 27 to obtain 76 mg of white solid (Compound 40). The yield is 60.5%.

$^1$H NMR (300 MHz, DMSO-d$_6$): δ 9.41 (s, 1H), 8.85 (d, J=2.45 Hz, 1 H), 8.35 (d, J=8.56 Hz, 2H), 8.30 (t, J=5.81 Hz, 1 H), 8.03 (d, J=8.86 Hz, 1 H), 7.93 (d, J=8.56 Hz, 1 H), 7.47 (M, 2 H), 4.60 (d, J=7.63 Hz, 1 H), 4.55 (m, 1 H), 4.00-4.10 (m, 2 H), 3.50-3.58 (m, 2 H),1.85 (s, 3H). MS (EI) m/z (%): 406 (M+, 16), 278 (100).

Example 42

N(((3S,3aS)-7-(6-(oxazolidin-2-one-3-yl)pyridin-3-yl)-1-oxo-1,3,3a,4-tetrahydrobenzo[b]oxazole[3,4-d][1,4]oxazin-3-yl)methyl)acetamide (41)

Step 1, Preparation of 3-(5-bromopyridin-2-yl)oxazolidin-2-one (41-B)

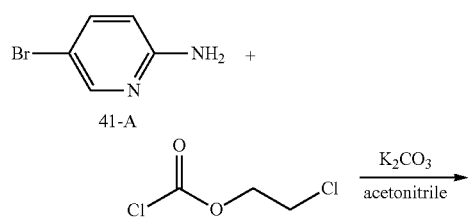

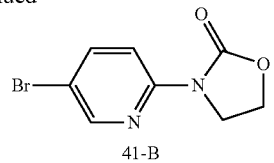

Compound 41-A (2-amino-5-bromopyridine) (3 g, 17.34 mmol) (purchased from Sun Chemical Technology (Shanghai) Co. Ltd.) and K$_2$CO$_3$ (6 g, 43.4 mmol) are added to acetonitrile (35 mL), and cooled by ice-salt bath to 0° C. Stir and slowly add dropwise with 2-chloroethyl chloroformate (2.98 g, 20.81 mmol). Once the addition is completed, allow rising to room temperature. Stir for 1 hour and then allow heated reflux for 3 hours. TLC (petroleum ether/ethyl acetate=3:1) is used to monitor the reaction. Once the raw materials are completely consumed by the reaction, the acetonitrile is evaporated, and add dichloromethane (100 mL) for dilution, followed by wash with water (100 mL) and saturated sodium chloride solution (100 mL) successively, drying with anhydrous sodium sulfate, and column chromatography (petroleum ether/ethyl acetate=5:1), to obtain 2.62 g of white powdery solid (Compound 41-B). The yield is 62.2%.

$^1$H NMR (300 MHz, CDCl$_3$): δ 8.57 (d, J=2.45 Hz 1 H), 8.18 (d, J=9.04 Hz 1 H), 7.80 (dd, J$_1$=2.45 Hz, J$_2$=9.04 Hz, 1 H), 4.50 (t, J=7.70 Hz, 2 H), 4.25 (d, J=7.70 Hz, 1 H). MS (EI) m/z (%): 244 (M+, 56), 199 (100).

Step 2, Preparation of N(((3S,3aS)-7-(6-(oxazolidin-2-one-3-yl)pyridin-3-yl)-1-oxo-1,3,3a,4-tetrahydrobenzo[b]oxazole[3,4-d][1,4]oxazin-3-yl)methyl)acetamide (41)

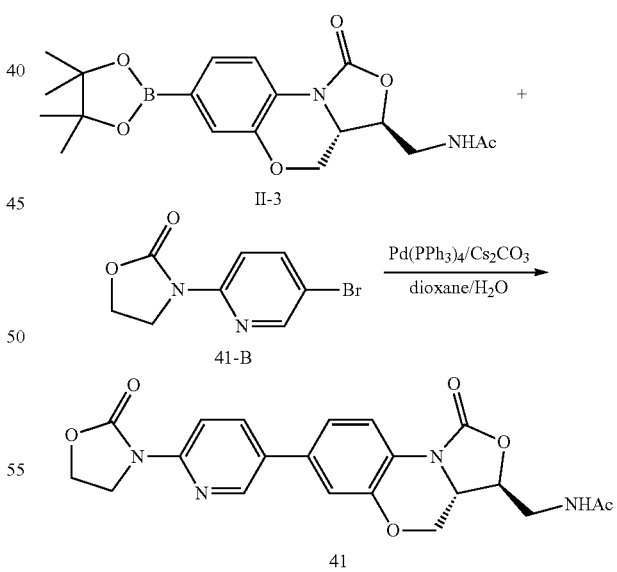

Compound II-3 (120 mg, 0.309 mmol) is dissolved in a mixed solvent of 1,4-dioxane (6 mL) and water (0.5 mL), and cesium carbonate (201.3 mg, 0.62 mmol), Compound 41-B (89.0 mg, 0.37 mmol) and Pd(PPh$_3$)$_4$ (35.7 mg, 0.03 mmol) are added. Follow the method described in example 27 to obtain 81 mg of white solid (Compound 41). The yield is 61.8%.

¹H NMR (300 MHz, DMSO-d₆): δ 8.68 (s, 1 H), 8.28 (t, 1 H), 8.15 (d, J=1.47 Hz, 2 H), 7.98 (dd, J₁=1.46 Hz, J₂=7.33 Hz, 1 H), 7.40 (d, J=2.20 Hz, 1 H), 7.36 (d, J=1.47 Hz, 1 H), 4.57 (d, J=7.69 Hz, 1 H), 4.45-4.52 (m, 3 H), 4.21 (t, J=7.70 Hz, 2H), 4.02-4.10 (m, 2 H), 3.50-3.61 (m, 2 H), 1.85 (s, 3 H). MS (EI) m/z (%): 424 (M⁺, 8), 296 (100).

Example 43

N(((3S,3aS)-7-(6-(hydroxyethyl-1-yl)pyridin-3-yl)-1-oxo-1,3,3a,4-tetrahydrobenzo[b]oxazole[3,4-d][1,4]oxazin-3-yl)methyl)acetamide (42)

Step 1, Preparation of 2-(hydroxyethyl-1-yl)-5-bromopyridine (42-A)

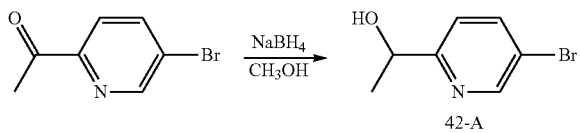

2-acetyl-5-bromopyridine (1 g, 5.0 mmol) (Bioorg. Med. Chem., 13, 2005, 6763-6770.) is dissolved in methanol (10 mL), and stir at room temperature. NaBH₄ (0.57 g, 15 mmol) is added in batches and stir at room temperature for 10 minutes. TLC (petroleum ether/ethyl acetate=10:1) is used to monitor the reaction. Once the reaction is completed, add water (15 mL) into the reaction solution, and stir for 0.5 hours. After that, methanol is evaporated, extract with dichloromethane (25 mL×3), merge the organic phases, followed by anhydrous Na₂SO₄ drying and filtering. The solvent is evaporated to obtain 0.93 g of oily liquid (Compound 42-A). The yield is 91.9%.

¹H NMR (300 MHz, CDCl₃) δ 8.62 (d, J=2.14 Hz, 1 H), 7.83 (dd, J₁=1.52 Hz, J₂=8.23 Hz, 1 H), 7.20 (d. J=8.24 Hz, 1 H), 4.76 (m, 1 H), 1.58 (d, J=6.41 Hz, 3 H), MS (EI) m/z (%): 201 (M⁺, 100).

Step 2, Preparation of N(((3S,3aS)-7-(6-(hydroxyethyl-1-yl)pyridin-3-yl)-1-oxo-1,3,3a,4-tetrahydrobenzo[b]oxazole[3,4-d][1,4]oxazin-3-yl)methyl)acetamide (42)

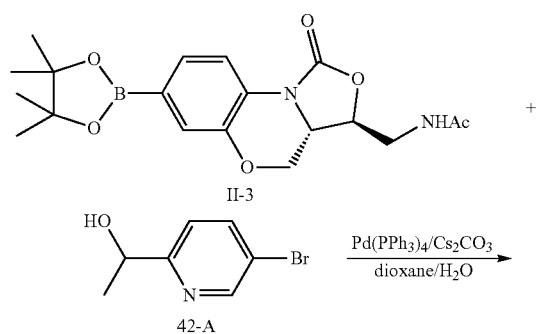

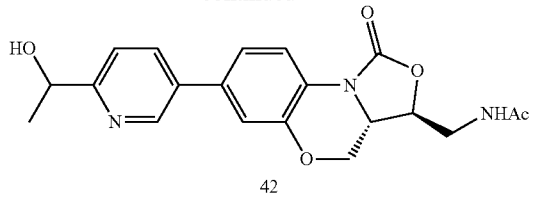

Compound II-3 (120 mg, 0.309 mmol) is dissolved in a mixed solvent of 1,4-dioxane (6 mL) and water (0.5 mL), and cesium carbonate (201.3 mg, 0.62 mmol), 42-A (74.9 mg, 0.37 mmol) and Pd(PPh₃)₄ (35.7 mg, 0.03 mmol) are added. Follow the method described in example 27 to obtain 65 mg of white solid (Compound 42). The yield is 54.9%.

¹H NMR (300 MHz, CDCl₃): δ 8.63 (d, J=1.83 Hz, 1 H), 8.10 (d, J=8.24 Hz, 1 H), 7.88 (dd, J₁=2.13 Hz, J₂=5.37 Hz, 1 H), 7.63 (d, J=14.04 Hz, 1 H), 7.38 (d, J=8.24 Hz, 1 H), 7.21 (d, J=9.77 Hz,1H), 6.10 (t, J=5.8 Hz, 1 H), 4.96 (q, J=6.41 Hz, 1H), 4.61 (dd, J₁=2.44 Hz, J₂=9.75 Hz, 1 H), 4.45 (m, 1 H), 3.90-4.10 (m, 2 H), 3.70-3.80 (m, 2 H), 2.05 (s, 3 H), 1.58 (d, J=6.41 Hz, 3H). MS (EI) m/z (%): 383 (M⁺, 50), 255 (100).

Example 44

N(((3S,3aS)-7-(5-acetylpyridin-3-yl)-1-oxo-1,3,3a,4-tetrahydrobenzo[b]oxazole[3,4-d][1,4]oxazin-3-yl)methyl)acetamide (43)

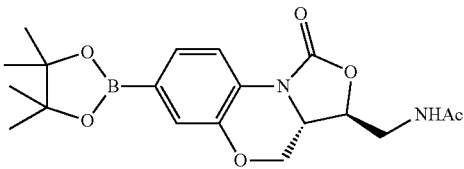

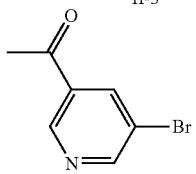

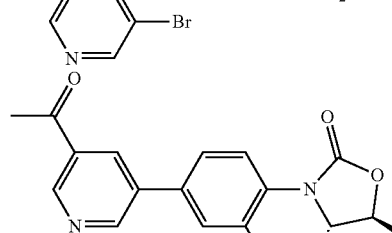

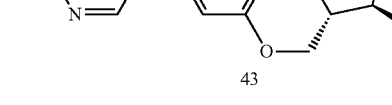

Compound II-3 (150 mg, 0.387 mmol) is dissolved in a mixed solvent of 1,4-dioxane (6 mL) and water (0.5 mL), and cesium carbonate (252.2 mg, 0.774 mmol), 3-acetyl-5-bromopyridine (92.81 mg, 0.464 mmol) (purchased from Sun Chemical Technology (Shanghai) Co. Ltd.) and Pd(PPh₃)₄ (44.7 mg, 0.039 mmol) are added. Follow the method described in example 27 to obtain 84 mg of white solid (Compound 43). The yield is 56.9%.

¹H NMR (300 MHz, CDCl₃): δ 9.14 (s, 1 H), 8.98 (s, 1 H), 8.40 (s, 1 H), 8.16 (d, J=8.54 Hz, 1 H), 7.21-7.30 (m, 2 H), 6.03 (t, J=6.10 Hz, 1 H), 4.62 (dd, J₁=2.44 Hz, J₂=10.06 Hz,

1 H), 4.45 (m, 1 H), 3.90-4.07 (m, 2 H), 3.68-3.78 (m, 2 H), 2.70 (s, 3 H), 2.05 (s, 3 H). MS (EI) m/z (%): 381 (M⁺, 86), 253 (100).

Example 45

N(((3S,3aS)-7-(5-cyanopyridin-3-yl)-1-oxo-1,3,3a,4-tetrahydrobenzo[b]oxazole[3,4-d][1,4]oxazin-3-yl)methyl)acetamide (44)

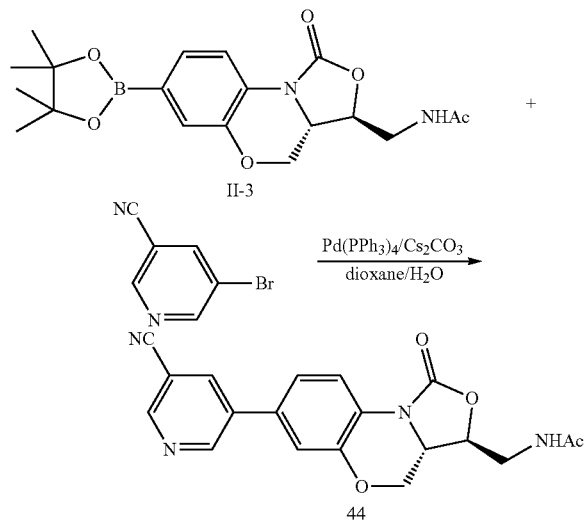

Compound II-3 (150 mg, 0.387 mmol) is dissolved in a mixed solvent of 1,4-dioxane (6 mL) and water (0.5 mL), and cesium carbonate (252.2 mg, 0.774 mmol), 3-cyano-5-bromopyridine (84.9 mg, 0.464 mmol) (purchased from Sun Chemical Technology (Shanghai) Co. Ltd.) and Pd(PPh₃)₄ (44.7 mg, 0.039 mmol) are added. Follow the method described in example 27 to obtain 95.1 mg of white solid (Compound 44). The yield is 67.6%.

¹H NMR (300 MHz, DMSO-d₆): δ 9.31 (s, 1 H), 9.18 (s, 1 H), 8.69 (s, 1 H), 8.01 (t, J=6.13 Hz, 1 H), 7.96 (dd, J₁=2.20 Hz, J₂=8.07 Hz, 1 H), 7.76 (dd, J₁=0.80 Hz, J₂=8.21 Hz, 1 H), 6.97 (d, J=8.07 Hz, 1 H), 4.62 (dd, J₁=2.64 Hz, J₂=10.06 Hz, 1 H), 4.48 (m, 1 H), 4.08 (dd, J₁=2.63 Hz, J₂=7.03 Hz, 1 H), 3.94 (t, J=10.12 Hz, 1 H), 3.76 (m, 2 H), 2.05 (s, 3 H). MS (EI) m/z (%): 364 (M⁺, 100).

Example 46

N(((3S,3aS)-7-(4-cyanopyridin-2-yl)-1-oxo-1,3,3a,4-tetrahydrobenzo[b]oxazole[3,4-d][1,4]oxazin-3-yl)methyl)acetamide (45)

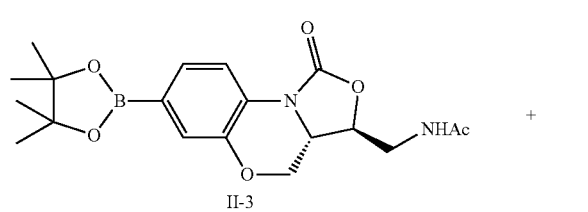

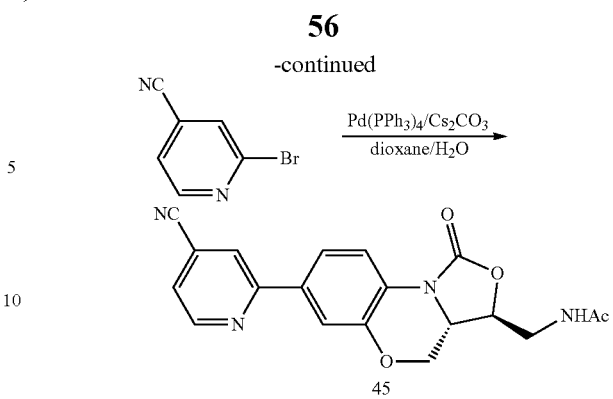

Compound II-3 (150 mg, 0.387 mmol) is dissolved in a mixed solvent of 1,4-dioxane (6 mL) and water (0.5 mL), and cesium carbonate (252.2 mg, 0.774 mmol), 2-bromo-4-cyanopyridine (84.9 mg, 0.464 mmol) (purchased from Sun Chemical Technology (Shanghai) Co. Ltd.) and Pd(PPh₃)₄ (44.7 mg, 0.039 mmol) are added. Follow the method described in example 27 to obtain 80 mg of white solid (Compound 45). The yield is 56.7%.

¹H NMR (300 MHz, DMSO-d₆): δ 8.87 (d, J=5.13 Hz,1 H), 8.48 (s, 1 H), 8.27 (t, J=6.13 Hz, 1 H), 8.05 (d, J=8.43 Hz, 1 H), 7.77-7.85 (m, 2 H), 7.70 (d, J=8.43 Hz, 1 H), 4.62 (d, J=7.33 Hz, 1 H), 4.52 (m, 1 H), 4.02-4.13 (m, 2 H), 3.50-3.60 (m, 2 H). 3.76 (m, 2 H), 1.85 (s, 3 H). MS (EI) m/z (%): 364 (M⁺, 76), 236 (100).

Example 47

N(((3S,3aS)-7-(6-formylpyridin-3-yl)-1-oxo-1,3,3a,4-tetrahydrobenzo[b]oxazole[3,4-d][1,4]oxazin-3-yl)methyl)acetamide (46)

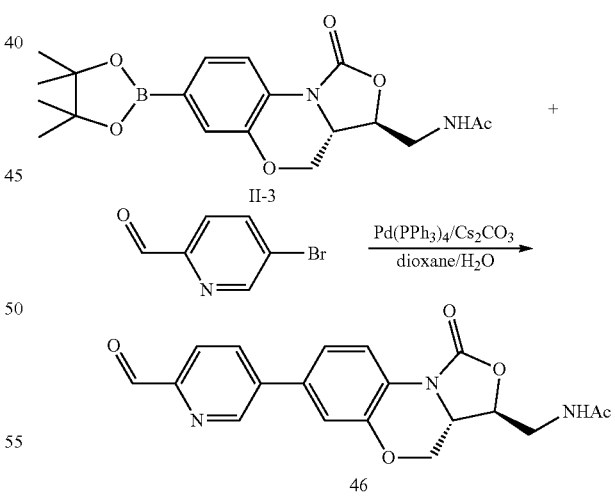

Compound II-3 (150 mg, 0.387 mmol) is dissolved in a mixed solvent of 1,4-dioxane (6 mL) and water (0.5 mL), and cesium carbonate (252.2 mg, 0.774 mmol), 5-bromo-2-pyridylaldehyde (86.3 mg, 0.464 mmol) (Tetrahedron. Lett., 41, 2000, 4335-4338.) and Pd(PPh₃)₄ (44.7 mg, 0.039 mmol) are added. Follow the method described in example 27 to obtain 50 mg of white solid (Compound 46). The yield is 35.2%.

¹H NMR (300 MHz, DMSO-d₆): δ 10.01 (s, 1H), 9.17 (d, J=1.47 Hz, 1 H), 8.27-8.36 (m, 2 H), 8.05 (dd, J₁=4.76 Hz, $J_2$=9.16 Hz, 1 H), 7.96 (d, J=8.44 Hz, 1 H), 7.53 (d, J=4.77 Hz, 1 H), 4.61 (d, J=7.70 Hz, 1 H), 4.50 (m, 1 H), 4.01-4.10 (m, 2 H), 3.50-3.60 (m, 2 H), 1.85 (s, 3 H). MS (ESI) m/z: 368 (M+1)$^+$.

Example 48

N(((3S,3aS)-7-(6-(hydroxymethylpyridin-3-yl)-1-oxo-1,3,3a,4-tetrahydrobenzo[b]oxazole[3,4-d][1,4]oxazin-3-yl)methyl)acetamide (47)

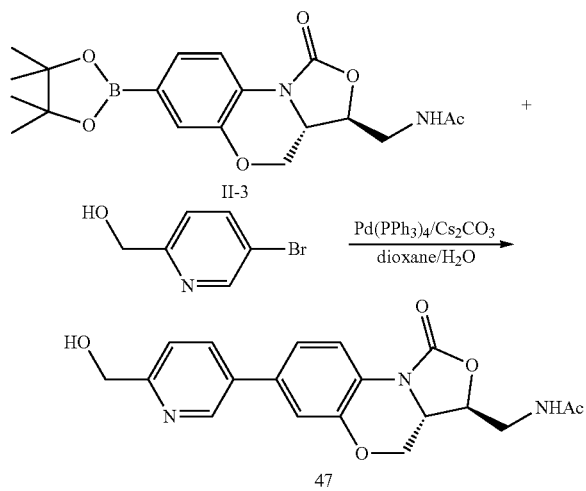

Compound II-3 (100 mg, 0.258 mmol) is dissolved in a mixed solvent of 1,4-dioxane (6 mL) and water (0.5 mL), and cesium carbonate (168.1 mg, 0.516 mmol), 2-hydroxymethyl-5-bromopyridine (58.11 mg, 0.309 mmol) (Tetrahedron. Lett., 41, 2000, 4335-4338.) and Pd(PPh$_3$)$_4$ (29.8 mg, 0.026 mmol) are added. Follow the method described in example 27 to obtain 50 mg of white solid (Compound 47). The yield is 52.5%.

$^1$H NMR (300 MHz, DMSO-d$_6$): δ 8.78 (s, 1 H), 8.30 (t, J=5.50 Hz, 1 H), 8.10 (dd, $J_1$=2.20 Hz, $J_2$=8.07 Hz, 1 H), 7.55 (d, J=8.06 Hz, 1 H), 7.33-7.40 (m, 2 H), 5.45 (brs, 1H), 4.55-4.63 (m, 3H), 4.50 (m, 1 H), 4.00-4.10 (m, 2 H), 3.50-3.60 (m, 2 H), 1.85 (s, 3 H). MS (EI) m/z (%): 369 (M$^+$, 24), 241 (100).

Example 49

N(((3S,3aS)-7-(5-(oxazolidin-2-one-3-yl)pyridin-3-yl)-1-oxo-1,3,3a,4-tetrahydrobenzo[b]oxazole[3,4-d][1,4]oxazin-3-yl)methyl)acetamide (48)

Step 1, Preparation of 3-(oxazolidin-2-one-3-yl)-5-bromopyridine (48-B)

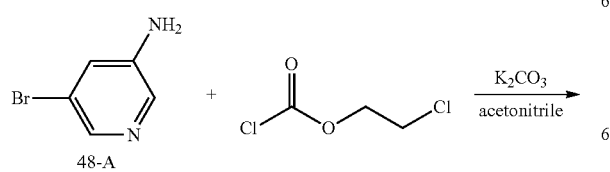

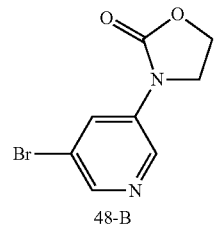

Compound 48-A (3-amino-5-bromopyridine) (1 g, 5.78 mmol) (purchased from Sun Chemical Technology (Shanghai) Co. Ltd.) and K$_2$CO$_3$ (1.99 g, 14.4 mmol) are added to acetonitrile (15 mL), and cooled by ice-salt bath to 0□. Stir and slowly add dropwise with 2-chloroethyl chloroformate (0.99 g, 6.94 mmol). Once the addition is completed, allow rising to room temperature. Stir for 1 hour and then allow heated reflux for 3 hours. TLC (petroleum ether/ethyl acetate=3:1) is used to monitor the reaction. Once the raw materials are completely consumed by the reaction, the acetonitrile is evaporated, add dichloromethane (100 mL) for dilution, followed by wash with water (50 mL) and saturated sodium chloride solution (50 mL) successively, drying with anhydrous sodium sulfate, and column chromatography (petroleum ether/ethyl acetate=5:1), to obtain 0.65 g of white powdery solid (Compound 48-B). The yield is 46.3%.

$^1$H NMR (300 MHz, CDCl$_3$): δ 8.56 (d, J=2.14 Hz 1 H), 8.47 (d, J=2.14 Hz 1 H), 8.44 (d, J=2.44 Hz, 1 H), 4.58 (t, 8.08 Hz,2 H), 4.14 (d, J=8.08 Hz, 1 H). MS (ET) m/z (%):242 (M$^+$, 100).

Step 2, Preparation of N(((3S,3aS)-7-(5-(oxazolidin-2-one-3-yl)pyridin-3-yl)-1-oxo-1,3,3a,4-tetrahydrobenzo[b]oxazole[3,4-d][1,4]oxazin-3-yl)methyl)acetamide (48)

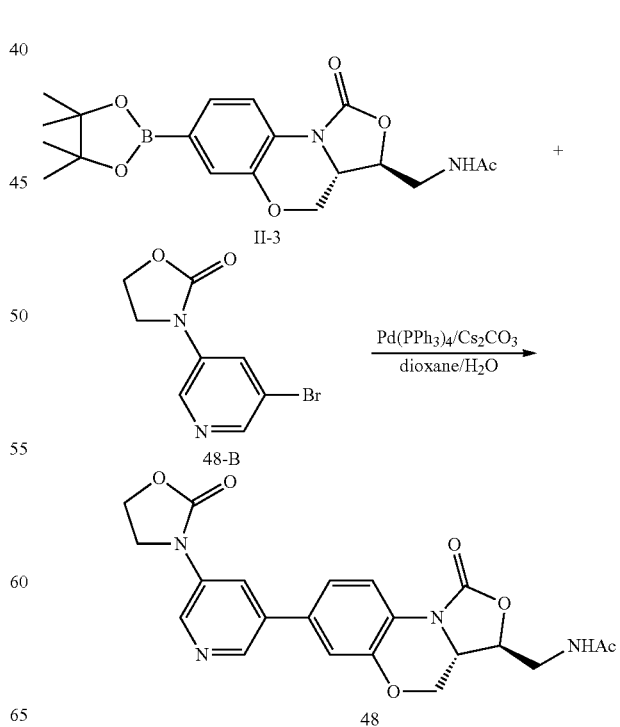

Compound II-3 (150 mg, 0.387 mmol) is dissolved in a mixed solvent of 1,4-dioxane (6 mL) and water (0.5 mL), and cesium carbonate (252.2 mg, 0.774 mmol), 48-B 3-(oxazolidin-2-one-3-yl)-5-bromopyridine (112.78 mg, 0.464 mmol) and Pd(PPh$_3$)$_4$ (44.7 mg, 0.039 mmol) are added. Follow the method described in example 27 to obtain 90 mg of white solid (Compound 48). The yield is 54.8%.

$^1$H NMR (300 MHz, DMSO-d$_6$): δ 8.80 (d, J=2.35 Hz, 1 H), 8.63 (d, J=2.05 Hz, 1 H), 8.33 (t, 1H), 8.16 (d, J=2.35 Hz, 1 H), 8.02 (d, J=9.08 Hz, 1 H), 7.32-7.41 (m, 2 H), 4.58 (d, J=7.62 Hz, 2H), 4.50 (t, J=7.33 Hz, 2 H), 4.18 (t, J=7.33 Hz, 2 H), 3.97-4.10 (m, 2 H), 3.47-3.60 (m, 2 H), 1.85 (s, 3 H). MS (EI) m/z (%): 424 (M$^+$, 4), 296 (100).

Example 50

(3R,3aS)-3-((1H-1,2,3-triazol-1-yl)methyl)-7-(4,4,5,5-tetramethyl-1,3,2 dioxaborolan-2-yl)-3a,4-dihydrobenzo[b]oxazole-[3,4-d][1,4]oxazine-1(3H)-one (II-7)

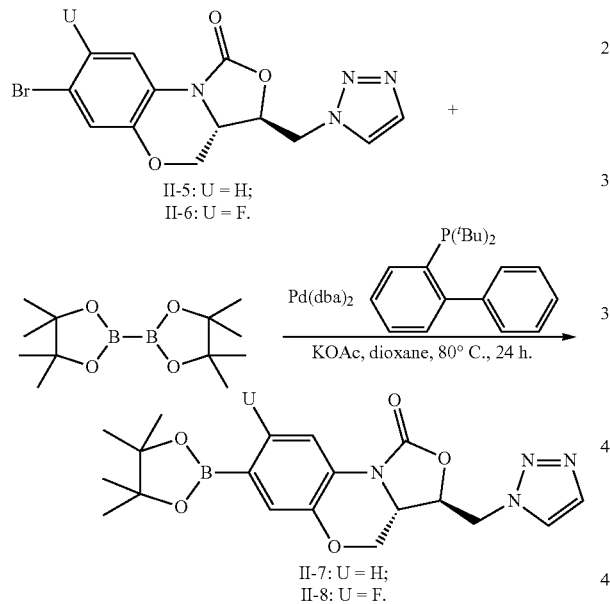

Pd(dba)$_2$ (92 mg, 0.16 mmol) and biphenyl-2-yl-di-tert-butylphosphine (60 mg, 0.20 mmol) are replaced with nitrogen for three times. Add 1,4-dioxane (60 mL) and stir at room temperature for 30 minutes, Bis(pinacolato)diboron (1.22 g, 4.8 mmol), potassium acetate KOAc (588 mg, 6 mmol), II-5 (1.40 g, 4 mmol) are added, and allow heated reaction under the protection of nitrogen at 80° C. for 24 hours. TLC (CH$_2$Cl$_2$/MeOH=50:1) is used for monitoring the reaction. After the reaction is completed, water is added (300 mL) for dilution, and extract with dichloromethane (100 mL×3). Each of dichloromethane layer is washed with water (200 mL) and saturated sodium chloride solution (200 mL) successively. Then dichloromethane layers are merged together, and dried with anhydrous sodium sulfate, spin-dried and go through column chromatography (CH$_2$Cl$_2$/MeOH=100:1) to obtain 1.13 g of light yellow viscous material (Compound II-7). The yield is 72.0%.

$^1$H NMR (300 MHz, CDCl$_3$): δ 7.95 (dd, J$_1$=1.71 Hz, J$_2$=7.82 Hz, 1 H), 7.80 (s, 1 H), 7.72 (s, 1 H), 6.92-7.10 (m, 2 H), 4.73 (dd, J$_1$=1.44 Hz, J$_2$=4.96 Hz, 2 H), 4.68 (m, 1 H), 4.45 (dd, J$_1$=3.05 Hz, J$_2$=10.17 Hz, 1 H), 4.05 (m, 1 H), 3.92 (d, J=10.12 Hz, 1 H), 1.24 (s, 12 H). MS (ESI) m/z (%): 399.3 (M+1)$^+$.

(3R,3aS)-8-fluoro-3-((1H-1,2,3-triazol-1-yl)methyl)-7-(4,4,5,5-tetramethyl-1,3,2 dioxaborolan-2-yl)-3a,4-dihydrobenzo[b]oxazole-[3,4-d][1,4]oxazine-1(3H)-one(II-8)

Pd(dba)$_2$ (92 mg, 0.16 mmol) and biphenyl-2-yl-di-tert-butylphosphine (60 mg, 0.20 mmol) are replaced with nitrogen for three times. Add 1,4-dioxane (60 mL) and stir at room temperature for 30 minutes. Bis(pinacolato)diboron (1.22 g, 4.8 mmol), potassium acetate KOAc (588 mg, 6 mmol), II-6 (1.48 g, 4 mmol) are added. Follow the method described above to obtain 1.18 g of light yellow powder (Compound II-8). The yield is 70.6%.

$^1$H NMR (300 MHz, CDCl$_3$): δ 7.97 (dd, J$_1$=1.71 Hz, J$_2$=7.82 Hz, 1 H), 7.81 (s, 1 H), 7.72 (s, 1 H), 6.96 (m, 1 H), 4.72 (dd, J$_1$=1.74 Hz, J$_2$=4.96 Hz, 2 H), 4.66 (m, 1 H), 4.45 (dd, J$_1$=2.86 Hz, J$_2$=10.15 Hz, 1 H), 4.03 (m, 1 H), 3.91 (d, J=10.11 Hz, 1 H), 1.24 (s, 12 H). MS (ESI) m/z (%): 417.2 (M+1)$^+$.

Example 51

(3R,3aS)-3-((1H-1,2,3-triazol-1-yl)methyl)-7-(6-cyanopyridin-3-yl)-3a,4-dihydrobenzo[b]oxazole[3,4-d][1,4]oxazine-1(3H)-one (49)

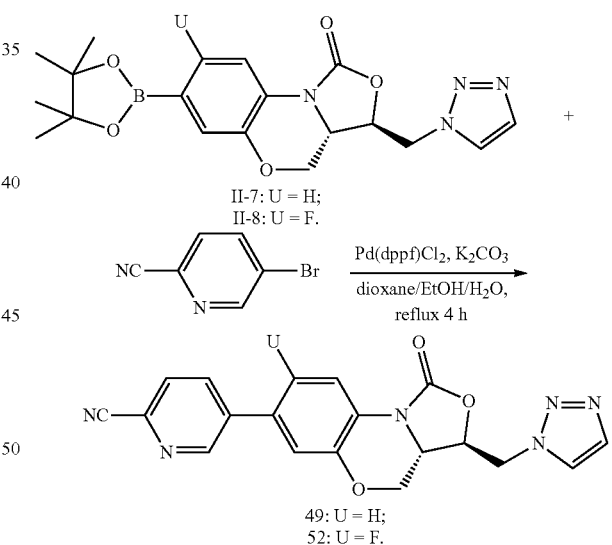

Compound II-7 (199 mg, 0.5 mmol) and 6-cyano-3 bromopyridine (128 mg, 0.7 mmol) (Bioorg. Med. Chem., 12, 2004, 5909-5915) are dissolved in 1,4-dioxane (10 mL), ethanol (3 mL) and water (3 mL), add K$_2$CO$_3$ (207 mg, 1.5 mmol), replace with nitrogen, and then add Pd(dppf)Cl$_2$ (30 mg, 0.036 mmol). Follow the method described in example 9 to obtain 72 mg of white solid (Compound 49). The yield is 38.5%.

$^1$H NMR (300 MHz, CDCl$_3$): δ 8.90 (d, J=0.81 Hz, 1 H), 8.15 (d, J=8.21 Hz, 1 H), 7.96 (dd, J$_1$=2.18 Hz, J$_2$=8.35 Hz, 1 H), 7.70-7.82 (m, 3 H), 6.92-7.10 (m, 2 H), 4.73 (dd, J$_1$=1.44 Hz, J$_2$=4.96 Hz, 2 H), 4.68 (m, 1 H), 4.45 (dd, J$_1$=3.05 Hz, $J_2$=10.17 Hz, 1 H), 4.06 (m, 1 H), 3.92 (d, J=10.12 Hz, 1 H). MS (ESI) m/z (%): 375.2 (M+1)⁺.

(3R,3aS)-8-fluoro-((1H-1,2,3-triazol-1-yl)methyl)-7-(6-cyanopyridin-3-yl)-3a,4-dihydrobenzo[b]oxazole[3,4-d][1,4]oxazine-1(3H)-one (52)

Compound II-8 (208 mg, 0.5 mmol) and 6-cyano-3-bromopyridine (128 mg, 0.7 mmol) (Bioorg. Med. Chem., 12, 2004, 5909-5915) are dissolved in 1,4-dioxane (10 mL), ethanol (3 mL) and water (3 mL), add $K_2CO_3$ (207 mg, 1.5 mmol), replace with nitrogen, and then add Pd(dppf)Cl$_2$ (30 mg, 0.036 mmol). Follow the method described in example 9 to obtain 69.6 mg of white solid (Compound 52). The yield is 35.5%.

¹H NMR (300 MHz, CDCl$_3$): δ 8.89 (d, 0.85 Hz, 1 H), 8.154 (d, J=8.18 Hz, 1 H), 7.94 (dd, $J_1$=2.34 Hz, $J_2$=8.35 Hz, 1 H), 7.70-7.83 (m, 3 H), 6.92-7.10 (m, 1 H), 4.72 (dd, $J_1$=1.74 Hz, $J_2$=4.96 Hz, 2 H), 4.67 (m, 1 H), 4.44 (dd, $J_1$=3.05 Hz, $J_2$=10.17 Hz, 1 H), 4.05 (m, 1 H), 3.94 (d, J=10.15 Hz, 1 H). MS (ESI) m/z (%): 393.2 (M+1)⁺.

Example 52

(3R,3aS)-3-((1H-1,2,3-triazol-1-yl)methyl)-7-(6-nitropyridin-3-yl)-3a,4-dihydrobenzo[b]oxazole[3,4-d][1,4]oxazine-1(3H)-one (50)

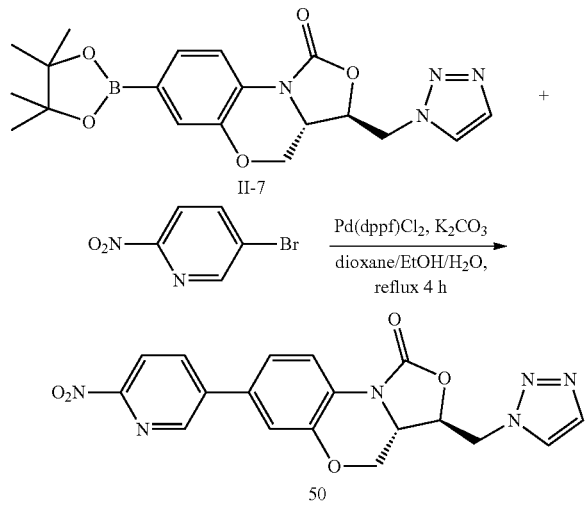

Compound II-7 (199 mg, 0.5 mmol) and 2-nitro-5 bromopyridine (122 mg, 0.6 mmol) (purchased from Sigma-Aldrich Co.) are dissolved in 1,4-dioxane (10 mL), ethanol (3 mL) and water (3 mL), and add $K_2CO_3$ (207 mg, 1.5 mmol), replace with nitrogen, and then add Pd(dppf)Cl$_2$ (30 mg, 0.036 mmol). Follow the method described in example 9 to obtain 54 mg of yellow foamy solid (Compound 50). The yield is 27.4%.

¹H NMR (300 MHz, CDCl$_3$): δ 8.81 (t, J=2.05 Hz, 1 H), 8.33 (d, J=8.21 Hz, 1 H), 8.20 (d, J=8.40 Hz, 1 H), 8.15 (dd, $J_1$=2.10 Hz, $J_2$=8.40 Hz, 1 H), 7.70-7.82 (m, 3 H), 6.92-7.10 (m, 2 H), 4.72 (dd, $J_1$=1.44 Hz, $J_2$=4.95 Hz, 2 H), 4.68 (m, 1 H), 4.46 (dd, $J_1$=3.06 Hz, $J_2$=10.12 Hz, 1 H), 4.06 (m, 1 H), 3.92 (d, J=10.12 Hz, 1 H), MS (ESI) m/z (%): 395.2 (M+1)⁺.

Example 53

(3R,3aS)-3-((1H-1,2,3-triazol-1-yl)methyl)-7-(6-(1-methyl-1H-tetrazol-5-yl)pyridin-3-yl)-3a,4-dihydrobenzo[b]oxazole[3,4-d][1,4]oxazine-1(3H)-one (51)

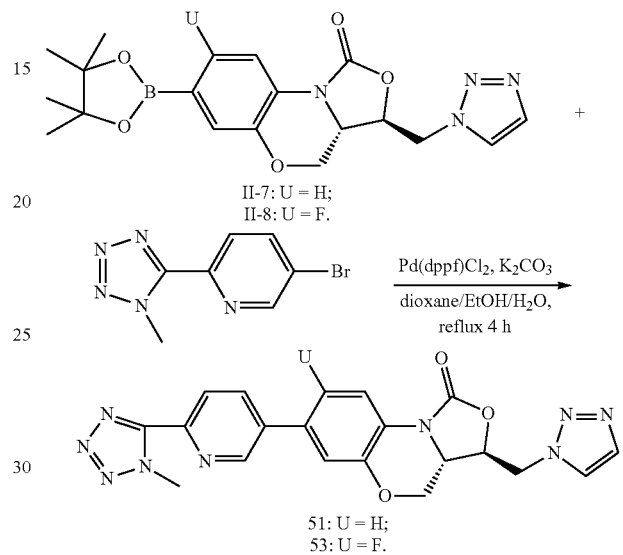

Compound II-7 (199 mg, 0.5 mmol) and 5-bromo-2-(1-methyl-2H-tetrazol-5-yl)pyridine (120 mg, 0.5 mmol) (Bioorg. Med. Chem., 12, 2004, 5909-5915.) are dissolved in 1,4-dioxane (10 mL), ethanol (3 mL) and water (3 mL), add $K_2CO_3$ (207 mg, 1.5 mmol), replace with nitrogen, and then add Pd(dppf)Cl$_2$ (30 mg, 0.036 mmol). Follow the method described in example 9 to obtain 85 mg of yellow foamy solid (Compound 51). The yield is 39.4%.

¹H NMR (300 MHz, CDCl$_3$): δ 8.99 (s, 1 H), 8.33 (d, J=6.62 Hz, 1 H), 8.14 (d, J=8.21 Hz, 1 H), 8.07 (d, J=7.63 Hz, 1 H), 7.70-7.82 (m, 3 H), 6.92-7.10 (m, 2 H), 4.72 (dd, $J_1$=1.44 Hz, $J_2$=4.95 Hz, 2 H), 4.68 (m, 1 H), 4.46 (dd, $J_1$=3.06 Hz, $J_2$=10.12 Hz, 1 H), 4.06 (m, 1 H), 3.92 (d, J=10.12 Hz, 1 H). MS (ESI) m/z (%): 432.2 (M+1)⁺.

(3R,3aS)-8-fluoro-3-((1H-1,2,3-triazol-1-yl)methyl)-7-(6-(1-methyl-1H-tetrazol-5-yl)pyridin-3-yl)-3a,4-dihydrobenzo[b]oxazole[3,4-d][1,4]oxazine-1(3H)-one (53)

Compound II-8 (208 mg, 0.5 mmol) and 5-bromo-2-(1-methyl-2H-tetrazol-5-yl)pyridine (120 mg, 0.5 mmol) (Bioorg. Med. Chem., 12, 2004, 5909-5915.) are dissolved in 1,4-dioxane (10 mL), ethanol (3 mL) and water (3 mL), add $K_2CO_3$ (207 mg, 1.5 mmol), replace with nitrogen, and then add Pd(dppf)Cl$_2$ (30 mg, 0.036 mmol). Follow the method described in example 9 to obtain 83.14 mg of yellow foamy solid (Compound 53). The yield is 37%.

¹H NMR (300 MHz, CDCl$_3$): δ 8.98 (s, 1 H), 8.33 (d, J=6.62 Hz, 1 H), 8.14 (d, J=8.21 Hz, 1 H), 8.07 (d, J=7.63 Hz, 1 H), 7.70-7.82 (m, 3 H), 6.92-7.10 (m, 1 H), 4.74 (dd, $J_1$=1.45 Hz, $J_2$=4.95 Hz, 2 H), 4.67 (m, 1 H), 4.45 (dd, $J_1$=3.06

Hz, $J_2$=10.15 Hz, 1 H), 4.05 (m, 1 H), 3.94 (d, J=10.10 Hz, 1 H). MS (ESI) m/z (%): 450.2 $(M+1)^+$.

Example 54

(3R,3aS)-3-((1H-1,2,3-triazol-1-yl)methyl)-7-(6-acetylpyridin-3-yl)-3a,4-dihydrobenzo[b]oxazole[3,4-d][1,4]oxazine-1(3H)-one (54)

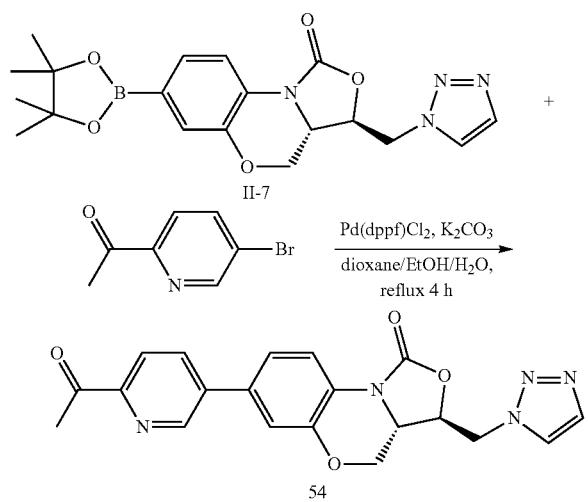

Compound II-7 (199 mg, 0.5 mmol) and 2-acetyl-5-bromopyridine (100 mg, 0.5 mmol) (Bioorg. Med. Chem., 13, 2005, 6763-6770.) are dissolved in 1,4-dioxane (10 mL), ethanol (3 mL) and water (3 mL), add $K_2CO_3$ (207 mg, 1.5 mmol), replace with nitrogen, and then add Pd(dppf)$Cl_2$ (30 mg, 0.036 mmol) Follow the method described in example 9 to obtain 85 mg of white solid (Compound 54). The yield is 43.4%.

$^1$H NMR (300 MHz, DMSO-$d_6$): δ 8.90 (d, J=0.81 Hz, 1 H), 8.15 (d, J=8.21 Hz, 1 H), 7.96 (dd, $J_1$=2.18 Hz, $J_2$=8.35 Hz, 1 H), 7.70-7.82 (m, 3 H), 6.92-7.10 (m, 2 H), 4.73 (dd, $J_1$=1.44 Hz, $J_2$=4.96 Hz, 2 H), 4.68 (m, 1 H), 4.45 (dd, $J_1$=3.05 Hz, $J_2$=10.17 Hz, 1 H), 4.06 (m, 1 H), 3.92 (d, J=10.12 Hz, 1 H). MS (EI) m/z (%): 374 ($M^+$, 100).

Example 55

(3R,3aS)-3-((1H-1,2,3-triazol-1-yl)methyl)-7-(6-cyanomethylpyridin-3-yl)-3a,4-dihydrobenzo[b]oxazole[3,4-d][1,4]oxazine-1(3H)-one (55)

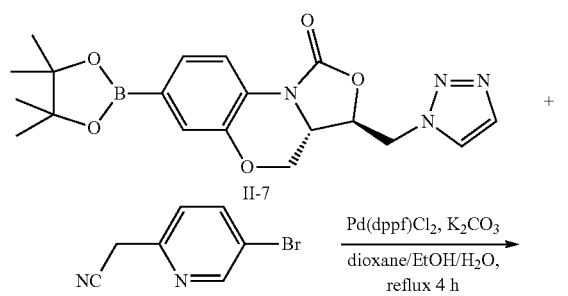

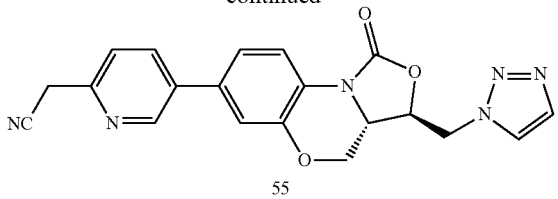

Compound II-7 (199 mg, 0.5 mmol) and 2-(5-bromopyridin-2-yl)acetonitrile (98.5 mg, 0.5 mmol) (J. Med. Chem. 51, 2008, 6558-6562) are dissolved in 1,4-dioxane (10 mL), ethanol (3 mL) and water (3 mL), add $K_2CO_3$ (207 mg, 1.5 mmol), replace with nitrogen, and then add Pd(dppf)$Cl_2$ (30 mg, 0.036 mmol). Follow the method described in example 9 to obtain 79 mg of white solid (Compound 55). The yield is 40.7%.

$^1$H NMR (300 MHz, DMSO-$d_6$): δ 8.79 (d, J=2.02 Hz, 1 H), 8.14 (d, J=8.43 Hz, 1 H), 7.92 (dd, $J_1$=2.38 Hz, $J_2$=8.06 Hz, 1 H), 7.53 (t, J=3.66 Hz, 1 H), 7.21 (td, $J_1$=2.01 Hz, $J_2$=8.43 Hz, 2 H), 6.92-7.10 (m, 2 H), 4.60 (d, J=10.08 Hz, 1 H), 4.45 (m, 1 H), 4.37 (s, 2H), 3.97-4.05 (m, 1 H), 3.95 (t,J=10.08 Hz, 1H) 3.70-3.78 (m, 2 H), MS (EI) m/z (%): 388 ($M^+$, 100).

Example 56

(3R,3aS)-3-((1H-1,2,3-triazol-1-yl)methyl)-7-(6-ethynylpyridin-3-yl)-3a,4-dihydrobenzo[b]oxazole[3,4-d][1,4]oxazine-1(3H)-one (56)

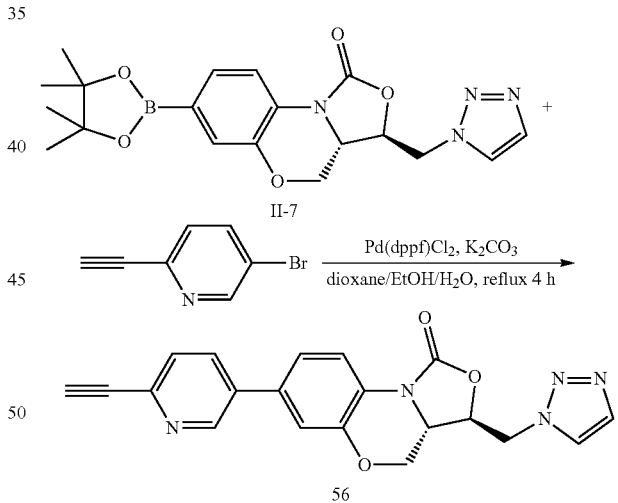

Compound II-7 (199 mg, 0.5 mmol) and 2-ethynyl-5-bromopyridine (91 mg, 0.5 mmol) (J. Org. Chem., 52, 1988, 386-390) are dissolved in 1,4-dioxane (10 mL), ethanol (3 mL) and water (3 mL), \add $K_2CO_3$ (207 mg, 1.5 mmol), replace with nitrogen, and then add Pd(dppf)$Cl_2$ (30 mg, 0.036 mmol). Follow the method described in example 9 to obtain 70 mg of white solid (Compound 56). The yield is 37.5%.

$^1$H NMR (300 MHz, DMSO-$d_6$): δ 8.90 (t, J=0.55 Hz, 1 H), 8.12 (dd, $J_1$=2.47 Hz, $J_2$=8.25 Hz, 1 H), 8.02 (d, J=9.07 Hz, 1 H), 7.61 (d, J=8.24 Hz, 1 H), 7.40-7.44 (dd, $J_1$=2.20 Hz, $J_2$=6.33 Hz, 2H), 6.92-7.10 (m, 2 H), 4.58 (d, J=7.15 Hz, 1 H), 4.53 (m, 1 H), 4.39 (s, 1 H), 4.02-4.10 (m, 2 H), 3.48-3.60 (m, 2 H), 1.87 (s, 3 H). MS (EI)m/z (%): 373 (M+, 100).

Example 57

(3R,3aS)-3-((1H-1,2,3-triazol-1-yl)methyl)-7-(6-(3-hydroxypropyn-1-yl)pyridin-3-yl)-3a,4-dihydrobenzo[b]oxazole[3,4-d][1,4]oxazine-1(3H)-one (57)

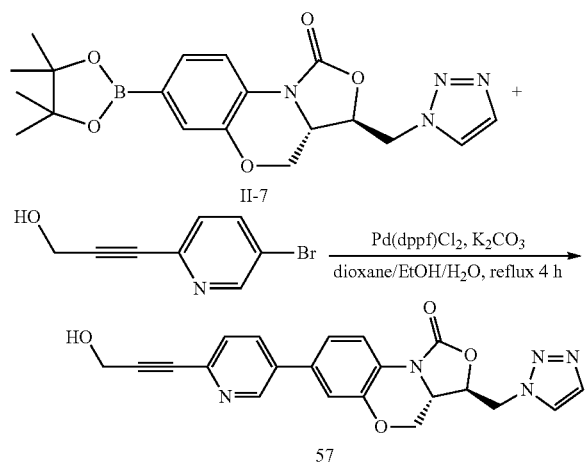

Compound II-7 (199 mg, 0.5 mmol) and 3-(5-bromopyridin-2-yl)propargyl alcohol (106.02 mg, 0.5 mmol) (J. Org. Chem., 69, 8723-8730) are dissolved in 1,4-dioxane (10 mL), ethanol (3 mL) and water (3 mL), add K$_2$CO$_3$ (207 mg, 1.5 mmol), replace with nitrogen, and then add Pd(dppf)Cl$_2$ (30 mg, 0.036 mmol). Follow the method described in example 9 to obtain 98 mg of white solid (Compound 57). The yield is 48.6%.

$^1$H NMR (300 MHz, DMSO-d$_6$): δ 8.90 (d, J=2.44 Hz, 1 H), 8.08 (dd, J$_1$=2.43 Hz, J$_2$=10.92 Hz, 1 H), 8.00 (d, J=9.75 Hz, 1 H), 7.58 (d, J=8.29 Hz, 1 H), 7.40 (d, J=6.33 Hz, 2H), 6.92-7.10 (m, 2 H), 4.60 (d, J=7.31 Hz, 1 H), 4.53 (m, 1 H), 4.37 (s, 2H), 4.02-4.10 (m, 2 H), 3.50-3.58 (m, 2 H), 1.85 (s, 3 H). MS (EI) m/z (%): 403 (M+, 100).

Example 58

(3R,3aS)-3-((1H-1,2,3-triazol-1-yl)methyl)-7-(6-(oxazolidin-2-one-3-yl)pyridin-3-yl)-3a,4-dihydrobenzo[b]oxazole[3,4-d][1,4]oxazine-1(3H)-one (58)

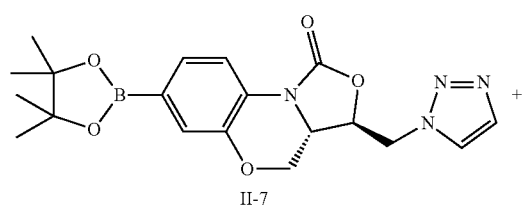

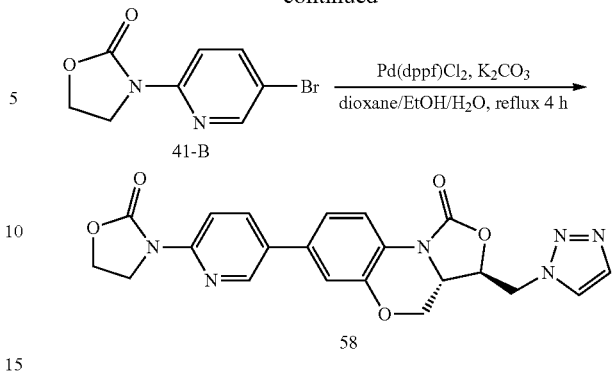

Compound II-7 (199 mg, 0.5 mmol) and 41-B (121.5 mg, 0.5 mmol) are dissolved in 1,4-dioxane (10 mL), ethanol (3 mL) and water (3 mL), add K$_2$CO$_3$ (207 mg, 1.5 mmol), replace with nitrogen, and then add Pd(dppf)Cl$_2$ (30 mg, 0.036 mmol). Follow the method described in example 9 to obtain 109.3 mg of white solid (Compound 58). The yield is 50.2%.

$^1$H NMR (300 MHz, DMSO-d$_6$): δ 8.68 (s, 1 H), 8.15 (d, J=1.47 Hz, 2 H), 7.98 (dd, J$_1$=1.46 Hz, J$_2$=7.33 Hz, 1 H), 7.40 (d, J=2.20 Hz,1 H), 7.36 (d, J=1.47 Hz,1 H), 6.92-7.10 (m, 2 H), 4.57 (d, J=7.69 Hz, 1 H), 4.45-4.52 (m, 3 H), 4.21 (t, J=7.70 Hz, 2H), 4.02-4.10 (m, 2 H), 3.50-3.61 (m, 2 H), 1.85 (s, 3 H). MS (EI) m/z (%): 434 (M+, 100).

Example 59

N(((3S,3aS)-7-(6-carboxypyridin-3-yl)-1-oxo-1,3,3a,4-tetrahydrobenzo[b]oxazole[3,4-d][1,4]oxazin-3-yl)methyl)acetamide (59)

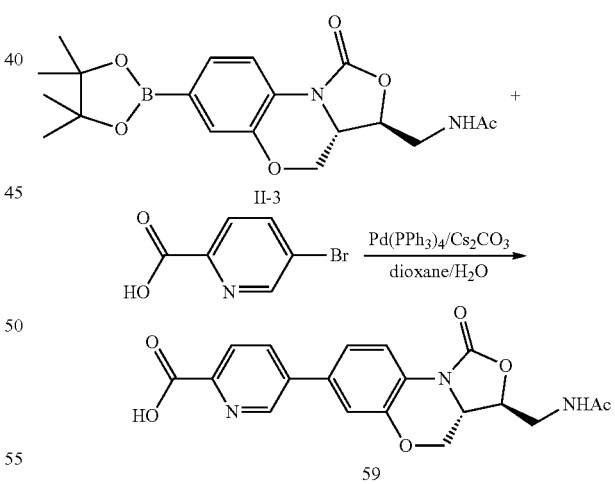

Compound II-3 (150 mg, 0.386 mmol) is dissolved in a mixed solvent of 1,4-dioxane (10 mL) and water (1 mL), and cesium carbonate (251.5 mg, 0.77 mmol), 5-bromopyridine-2-carboxylic acid (93.7 mg, 0.464 mmol) (purchased from Sigma-Aldrich Co.) and Pd(PPh$_3$)$_4$ (44.6 mg, 0.039 mmol) are added. Follow the method described in example 27 to obtain 54 mg of white powdery solid (Compound 59). The yield is 35.7%.

$^1$H NMR (300 MHz, DMSO-d$_6$): δ 9.00 (s, 1 H), 8.20-8.34 (m, 2 H), 8.01-8.12 (m, 2 H), 7.51 (d, J=4.77 Hz, 2 H), 4.60 (d,

J=7.73 Hz, 1 H), 4.56 (d, J=5.49 Hz, 1 H), 4.02-4.17 (m, 2 H), 3.53-3.60 (m, 2 H), 1.82 (s, 3 H). MS (EI) m/z (%):383 (M+, 16), 211(100).

Example 60

N(((3S,3aS)-7-(6-carboxylate pyridin-3-yl)-1-oxo-1,3,3a,4-tetrahydrobenzo[b]oxazole[3,4-d][1,4]oxazin-3-yl)methyl)acetamide (60)

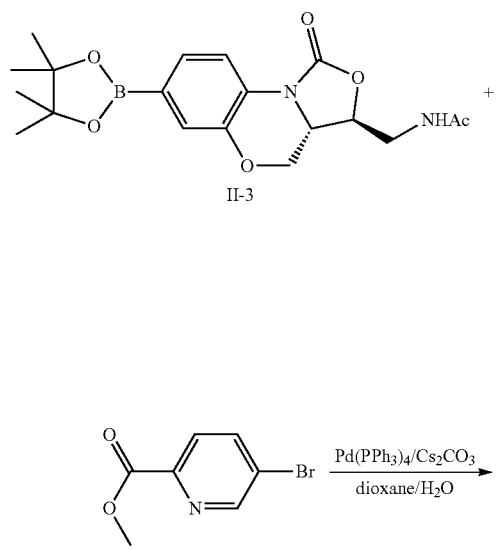

Compound II-3 (500 mg, 1.29 mmol) is dissolved in a mixed solvent of 1,4-dioxane (25 mL) and water (2.5 mL), and cesium carbonate (840.6 mg, 2.58 mmol), 5-bromopyridine-2-carboxylate (334 mg, 1.55 mmol) (purchased from J&K CHEMICAL LTD., Shanghai) and Pd(PPh$_3$)$_4$ (149 mg, 0.13 mmol) are added. Follow the method described in example 27 to obtain 204 mg of white powdery solid (Compound 60). The yield is 39.8%.

$^1$H NMR (300 MHz, CDCl$_3$): δ 8.92 (d, J=2.14 Hz, 1 H), 8.16 (m, 2 H), 7.98 (dd, J$_1$=2.24 Hz, J$_2$=8.24 Hz, 1 H), 7.15 (d, J=1.83 Hz. 1 H), 7.12 (d, J=2.14 Hz, 1 H), 6.05 (t, J=6.10 Hz, 1 H), 4.61 (dd, J$_1$=2.44 Hz, J$_2$=9.77 Hz, 1 H), 4.45 (m, 1 H), 3.90-4.00 (m, 2 H), 4.02 (s, 3 H), 3.70-3.78 (m, 2 H), 2.07 (s, 3 H), MS (EI) m/z (%): 397 (M+, 26), 269(100).

Example 61

N(((3S,3aS)-7-(6-(1-aminocycloprop-1-yl)pyridin-3-yl)-1-oxo-1,3,3a,4-tetrahydrobenzo[b]oxazole-[3,4-d][1,4]oxazin-3-yl)methyl)acetamide (61)

Step 1: N(((3S,3aS)-7-(6-(1-(Boc-amino)cycloprop-1-yl)pyridin-3-yl)-1-oxo-1,3,3a,4-tetrahydrobenzo[b]oxazole-[3,4-d][1,4]oxazin-3-yl)methyl)acetamide (61-A)

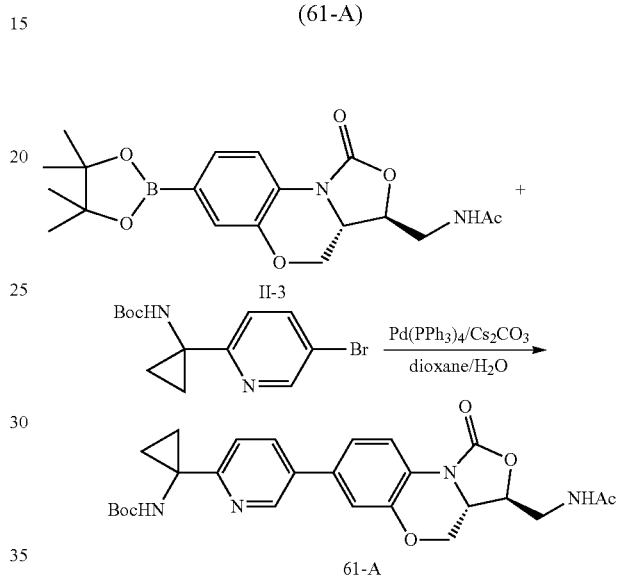

Compound II-3 (300 mg, 0.77 mmol) is dissolved in a mixed solvent of 1,4-dioxane (15 mL) and water (1.5 mL), and cesium carbonate (502 mg, 1.54 mmol), 2-(1-(Boc-amino)cycloprop-1-yl)-5-bromopyridine (290 mg, 0.93 mmol) (WO2004/020737) and Pd(PPh$_3$)$_4$ (89 mg, 0.077 mmol) are added. Follow the method described in example 27 to obtain 234 mg of white powdery solid (Compound 61-A). The yield is 61.5%.

$^1$H NMR (300 MHz, CDCl$_3$): δ 8.62 (d, J=1.65 Hz, 1 H), 8.06 (d, 9.51 Hz, 1 H), 7.77 (dd, J$_1$=2.20 Hz, J$_2$=8.23 Hz, 1 H), 7.47 (d, J=8.24 Hz, 1 H), 7.10-7.18 (m, 2 H), 6.13 (t, J=6.10 Hz, 1 H), 5.45 (s, 1 H), 4.56 (d, J=17.96 Hz 1 H), 4.37-4.48 (m, 1 H), 3.85-4.05 (m, 2 H), 3.60-3.78 (m, 2 H), 2.07 (s, 3 H), 1.60 (s, 9 H). MS (ESI) m/z (%):495 (M+, 100).

Step 2: N(((3S,3aS)-7-(6-(1-aminocycloprop-1-yl)pyridin-3-yl)-1-oxo-1,3,3a,4-tetrahydrobenzo[b]oxazole-[3,4-d][1,4]oxazin-3-yl)methyl)acetamide (61)

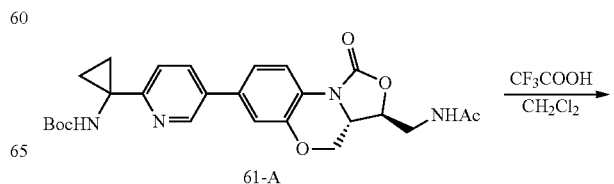

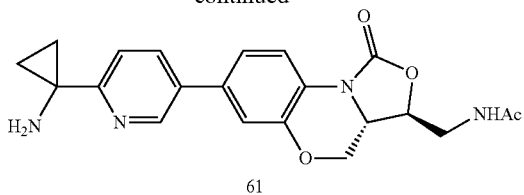

Compound 61-A (130 mg, 0.26 mmol) is dissolved in dichloromethane (5 mL), add trifluoroacetic acid (2.5 mL) and stir at room temperature for 1 hour. TLC (dichloromethane/methanol=10:1) is used for monitoring the reaction. After the reaction is completed, stop the reaction, and the solvent is evaporated. Then add a mixture solution of dichloromethane/methanol=20:1 (30 mL) for dissolution, stir and adjust to pH greater than 10 with 10% sodium hydroxide aqueous solution. After standing for layering, the organic phase is separated. Extract with a mixture solution of dichloromethane/methanol=20:1 (30 mL) twice before merging the organic phases, then wash with saturated sodium chloride solution (30 mL), dry with anhydrous sodium sulfate, evaporate the solvent, and perform C-18 reverse phase column chromatography, to obtain 96 mg of white powdery solid (Compound 61). The yield is 93.6%.

$^1$H NMR (300 MHz, DMSO-d$_6$): δ 8.69 (d, J=1.83 Hz, 1 H), 8.30 (t, J=6.23 Hz, 1 H), 7.95-8.03 (m, 2 H), 7.79 (d, J=8.43 Hz, 1 H), 7.30-7.38 (dd, J$_1$=2.20 Hz, J$_2$=10.27 Hz, 2 H), 4.56 (d, J=7.33 Hz, 1 H), 4.50 (dd, J$_1$=5.13 Hz, J$_2$=11.73 Hz 1 H), 3.97-4.06 (m, 2 H), 3.47-4.00 (m, 2 H),1.87 (s, 3 H), 1.60 (s, 9 H), 1.25 (dd, J$_1$=3.67 Hz, J$_2$=6.97 Hz 2 H), 0.98 (dd, J$_1$=3.30 Hz, J$_2$=6.60 Hz 2 H). MS (ESI) m/z (%): 394 (M$^+$, 64), 350(100).

Example 62

N(((3S,3aS)-7-(6-(4-methyl piperazin-1-yl)pyridin-3-yl)-1-oxo-1,3,3a,4-tetrahydrobenzo[b]oxazole-[3,4-d][1,4]oxazin-3-yl)methyl)acetamide (62)

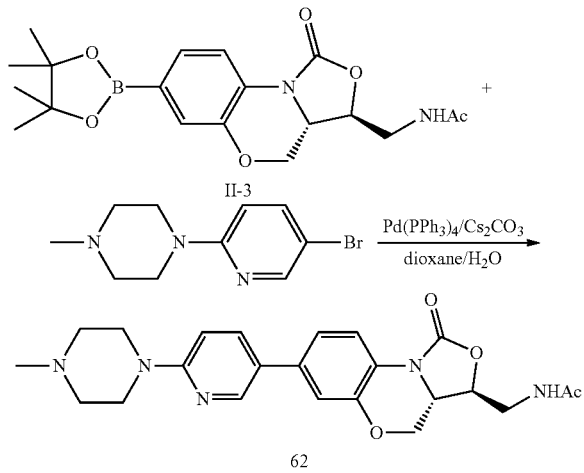

Compound II-3 (150 mg, 0.386 mmol) is dissolved in a mixed solvent of 1,4-dioxane (10 mL) and water (1 mL), and cesium carbonate (251.5 mg, 0.77 mmol), 2-(4-methyl piperazin-1-yl)-5-bromopyridine (118.6 mg, 0.464 mmol) (purchased from Sigma-Aldrich Co.) and Pd(PPh$_3$)$_4$ (44.6 mg, 0.039 mmol) are added. Follow the method described in example 27 to obtain 32.3 mg of white powdery solid (Compound 62). The yield is 19.1%.

$^1$H NMR (300 MHz, DMSO-d$_6$): δ 8.50 (d, J=2.44 Hz, 1 H), 8.32 (t, 1 H), 7.96 (dd, J$_1$=2.92 Hz, J$_2$=5.37 Hz, 1 H), 7.93 (d, J=2.44 Hz, 1 H), 7.32 (d, J=1.95 Hz, 1 H), 7.26 (s, 1H), 6.99 (d, J=9.78 Hz, 1 H), 4.55 (d, J=7.31 Hz, 1 H), 4.50 (d, J=6.32 Hz, 1 H), 3.95-4.10 (m, 2 H), 3.85 (t, J=4.88 Hz, 4 H), 3.48-3.60 (m, 2 H), 3.25 (t, J=4.88 Hz, 4 H), 2.21 (s, 3 H)2.05 (s, 3 H). MS (EI) m/z (%):423 (M$^+$, 50), 354 (100).

Example 63

N(((3S,3aS)-7-(6-cyanopyridin-3-yl)-1-oxo-1,3,3a,4-tetrahydrobenz[b]oxazole-[3,4-d][1,4]oxazin-3-yl)methyl)acetamide hydrochloride (63)

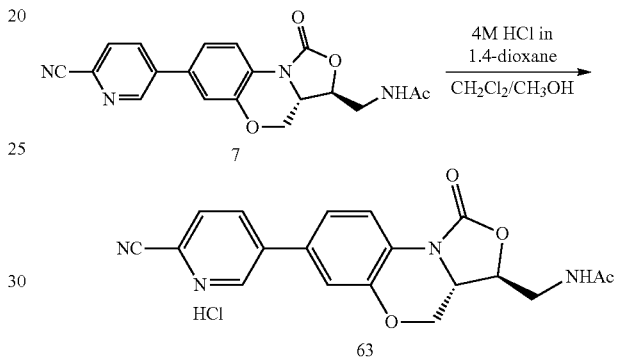

Compound 7 (364.4 mg, 1 mmol) is dissolved in a mixed solvent of CH$_2$Cl$_2$/CH$_3$OH=10:1 (10 mL). Add dropwise with 4M HCl in 1,4-dioxane (2.5 mL) at room temperature and stir for 0.5 hours. After that, evaporate the solvent and the residue is washed with methanol (5 ml) and filtered to obtain 300 mg of white solid (Compound 63). The yield is 74.8%.

Elemental analysis: calculated value: C, 56.93; H, 4.28; Cl, 8.85; N, 13.98; O, 15.97, measured value: C, 56.90; H, 4.32; Cl, 8.83; N, 13.97; O, 16.00.

Example 64

N(((3S,3aS)-7-(6-cyanopyridin-3-yl)-1-oxo-1,3,3a,4-tetrahydrobenzo[b]oxazole-[3,4-d][1,4]oxazin-3-yl)methyl)acetamide methanesulfonate (64)

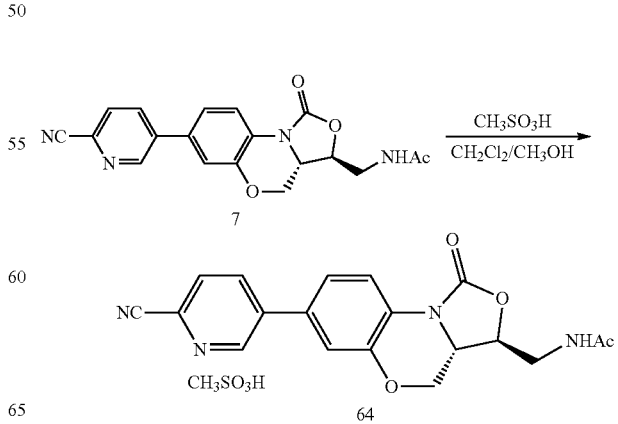

Compound 7 (364.4 mg. 1 mmol) is dissolved in a mixed solvent of CH$_2$Cl$_2$/CH$_3$OH=10:1 (10 mL). Add dropwise with CH$_3$SO$_3$H (105.7 mg, 1.1 mmol) in 1,4-dioxane (2.5 ml) at room temperature and stir for 0.5 hours. After that, evaporate the solvent and the residue is washed with methanol (5 ml) and filtered to obtain 333 mg of white solid (Compound 64). The yield is 72.3%.

Elemental analysis: calculated value: C, 52.17; H, 4.38; N, 12.17; O, 24.32; S, 6.96, measured value: C, 52.20; H, 4.40; N, 12.18; O, 24.27; S, 6.93.

Example 65

N(((3S,3aS)-7-(6-cyanopyridin-3-yl)-1-oxo-1,3,3a,4-tetrahydrobenzo[b]oxazole-[3,4-d][1,4]oxazin-3-yl)methyl)acetamide sulfate (65)

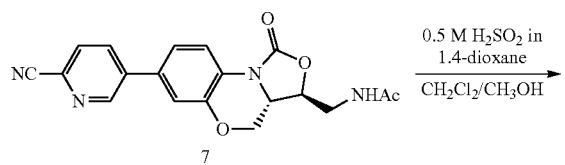

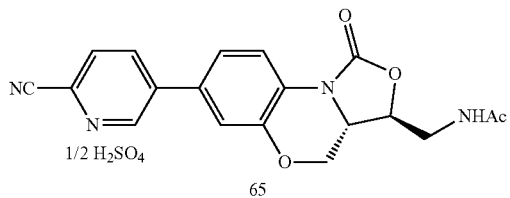

Compound 7 (364.4 mg, 1 mmol) is dissolved in a mixed solvent of CH$_2$Cl$_2$/CH$_3$OH=10:1 (10 mL). Add dropwise 0.5M H$_2$SO$_4$ in 1,4-dioxane (1.1 mL) at room temperature. Follow the method of example 63 to obtain 322 mg of gray solid (Compound 65). The yield is 77.9%.

Elemental analysis: calculated value: C, 55.20; H, 4.14; N, 13.55; O, 23.22; S, 3.88, measured value: C, 55.18; H, 4.12; N, 13.57; O, 23.23; S, 3.90.

Example 66

N((3S,3aS)-7-(6-cyanopyridin-3-yl)-1-oxo-1,3,3a,4-tetrahydrobenzo[b]oxazole-[3,4-d][1,4]oxazin-3-yl)methyl)acetamide benzene sulfonate (66)

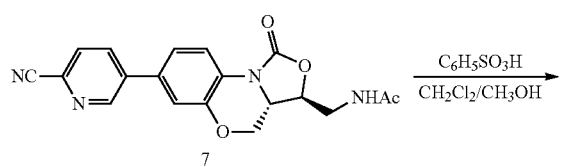

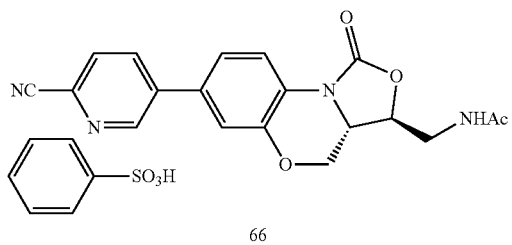

Compound 7 (364.4 mg, 1 mmol) is dissolved in a mixed solvent of CH$_2$Cl$_2$/CH$_3$OH=10:1 (10 mL). Add dropwise benzenesulfonic acid (174 mg, 1.1 mmol) in 1,4-dioxane (2.5 mL) at room temperature. Follow the method of example 64 to obtain 311.5 mg of white solid (Compound 66). The yield is 61.1%.

Elemental analysis: calculated value: C, 57.46; H, 4.24; N, 10.72; O, 21.43; S, 6.14, measured value: C, 57.49; H, 4.24; N, 10.70; O, 21.46; S, 6.11.

Example 67

N(((3S,3aS)-7-(6-(cyano-2-yl)pyridin-3-yl)-1-oxo-1,3,3a,4-tetrahydrobenzo[b]oxazole-[3,4-d][1,4]oxazin-3-yl)methyl)acetamide hydrochloride (67)

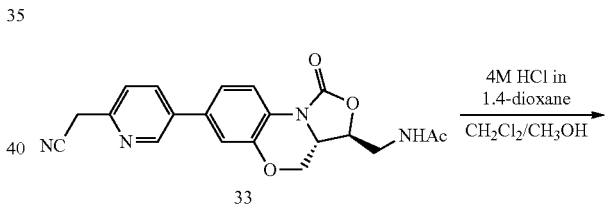

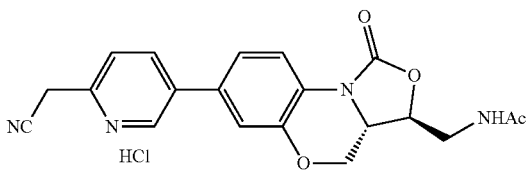

Compound 33 (378.4 mg, 1 mmol) is dissolved in a mixed solvent of CH$_2$Cl$_2$/CH$_3$OH=10:1 (10 mL). Add dropwise 4M HCl in 1,4-dioxane (2.5 ml) at room temperature. Follow the method of example 63 to obtain 308 mg of white solid (Compound 67). The yield is 74.2%.

Elemental analysis: calculated value: C, 57.90; H, 4.62; Cl, 8.55; N, 13.51; O, 15.43, measured value: C, 57.93; H, 4.63; Cl, 8.54; N, 13.50; O, 15.40.

Example 68

N(((3S,3aS)-7-(6-(cyano-2-yl)pyridin-3-yl)-1-oxo-1,3,3a,4-tetrahydrobenzo[b]oxazole-[3,4-d][1,4]oxazin-3-yl)methyl)acetamide methanesulfonate (68)

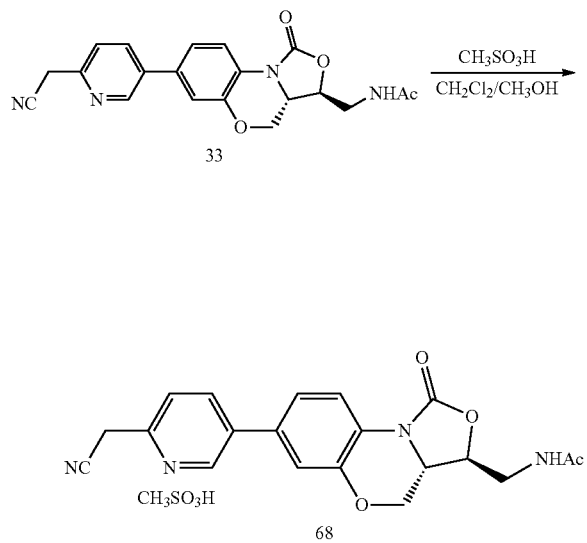

Compound 33 (378.4 mg, 1 mmol) is dissolved in a mixed solvent of $CH_2Cl_2/CH_3OH$=10:1 (10 mL). Add dropwise $CH_3SO_3H$ (105.7 mg, 1.1 mmol) in 1,4-dioxane (2.5 ml) at room temperature. Follow the method of example 64 to obtain 353.3 mg of white solid (Compound 68). The yield is 74.5%.

Elemental analysis: calculated value: C, 53.16; H, 4.67; N, 11.81; O, 23.60; S, 6.76, measured value: C, 53.15; H, 4.69; N, 11.83; O, 23.58; S, 6.79.

Example 69

N(((3S,3aS)-7-(6-(oxazolidin-2-one-3-yl)pyridin-3-yl)-1-oxo-1,3,3a,4-tetrahydrobenzo[b]oxazole-[3,4-d][1,4]oxazin-3-yl)methyl)acetamide hydrochloride (69)

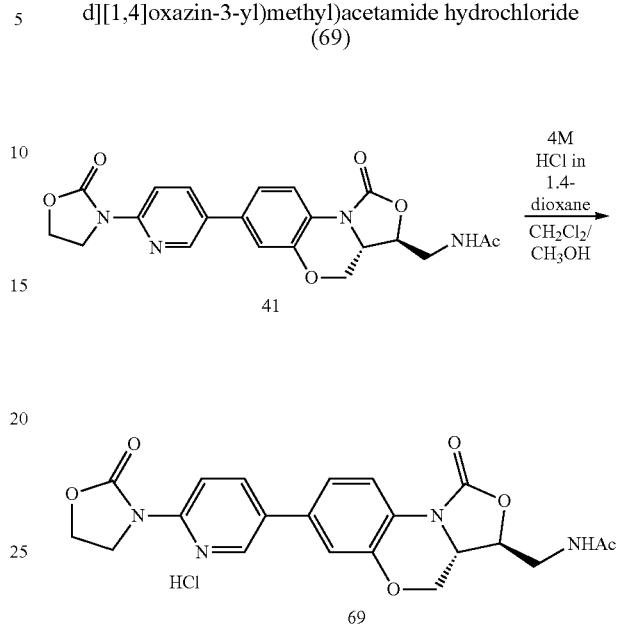

Compound 41 (424.4 mg, 1 mmol) is dissolved in a mixed solvent of $CH_2Cl_2/CH_3OH$=10:1 (10 mL). Add dropwise 4M HCl in 1,4-dioxane (2.5 ml) at room temperature. Follow the method of example 63 to obtain 393.5 mg of white solid (Compound 69). The yield is 85.4%.

Elemental analysis: calculated value: C, 54.73; H, 4.59; Cl, 7.69; N, 12.16; O, 20.83, measured value: C, 54,75; H, 4.61; Cl, 7.67; N, 12.14; O, 20.80.

Example 70

N(((3S,3aS)-7-(6-(oxazolidin-2-one-3-yl)pyridin-3-yl)-1-oxo-1,3,3a,4-tetrahydrobenzo[b]oxazole-[3,4-d][1,4]oxazin-3-yl)methyl)acetamide methanesulfonate (70)

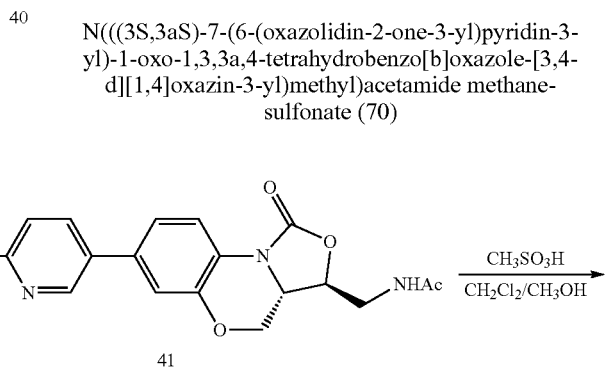

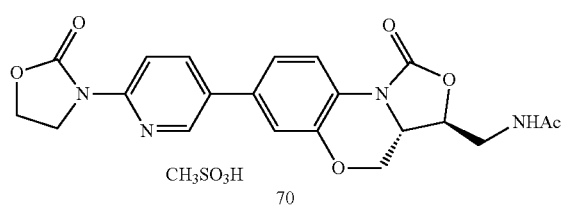

Compound 41 (424.4 mg, 1 mmol) is dissolved in a mixed solvent of $CH_2Cl_2/CH_3OH=10:1$ (10 mL). Add dropwise $CH_3SO_3H$ (105.7 mg, 1.1 mmol) in 1,4-dioxane (2.5 mL) at room temperature. Follow the method of example 64 to obtain 405.7 mg of white solid (Compound 70). The yield is 77.9%.

Elemental analysis: calculated value: C, 50.76; H, 4.65; N, 10.76; O, 27.66; S, 6.16, measured value: C, 50.79; H, 4.68; N, 10.74; O, 27.69; S, 6.14.

Example 71

N(((3S,3aS)-7-(6-(1-aminocycloprop-1-yl)pyridin-3-yl)-1-oxo-1,3,3a,4-tetrahydrobenzo[b]oxazole-[3,4-d][1,4]oxazin-3-yl) methyl)acetamide methanesulfonate (71)

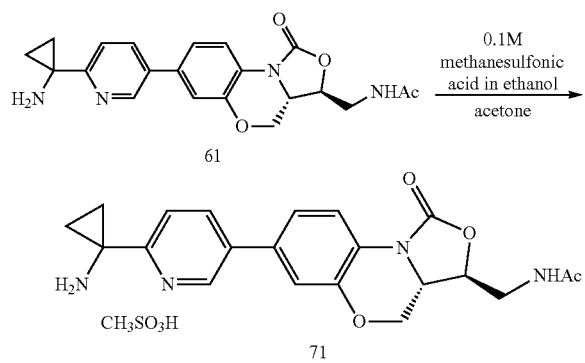

Compound 61 (150 mg, 0.38 mmol) is dissolved in acetone (2.5 mL). Add dropwise 0.1 M $CH_3SO_3H$ in ethanol (4.2 mL) at room temperature. Follow the method of example 64 to obtain 149.1 mg of white solid (Compound 71). The yield is 80%.

Elemental analysis: calculated value: C, 53.87; H, 5.34; N, 11.42; O, 22.83; S, 6.54, measured value: C, 53.91; H, 5.36; N, 11.38; O, 22.82; S, 6.53.

Example 72

N(((3S,3aS)-7-(6-(piperazin-1-yl)pyridin-3-yl)-1-oxo-1,3,3a,4-tetrahydrobenzo[b]oxazole-[3,4-d][1,4]oxazin-3-yl)methyl) acetamide hydrobromide (72)

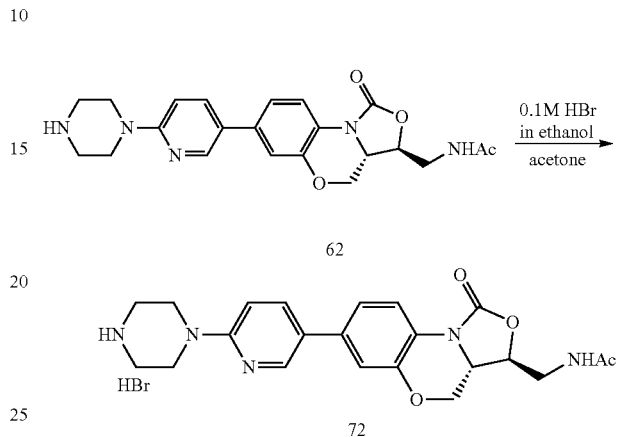

Compound 62 (100 mg, 0.236 mmol) is dissolved in acetone (8 mL). Add dropwise 0.1 M HBr in ethanol (2.6 ml) at room temperature. Follow the method of example 63 to obtain 100 mg of white solid (Compound 72). The yield is 84%.

Elemental analysis: calculated value: 52.39; H, 5.20; Br, 15.84; N, 13.89; O, 12.69, measured value: C, 52.42; H, 5.21; Br, 15.86; N, 13.86; O, 12.68.

Example 73

N(((3S,3aS)-7-(6-(piperazin-1-yl)pyridin-3-yl)-1-oxo-1,3,3a,4-tetrahydrobenzo[b]oxazole-[3,4-d][1,4]oxazin-3-yl)methyl)acetamide L-(+)-tartrate (73)

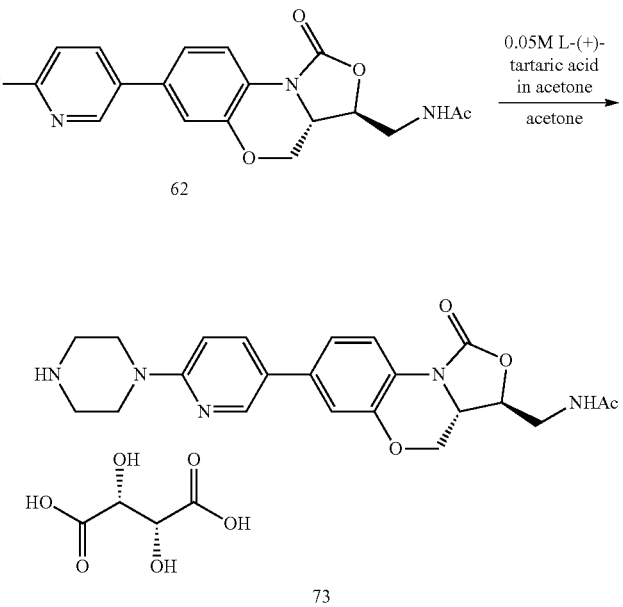

Compound 62 (100 mg, 0.236 mmol) is dissolved in acetone (8 mL). Add dropwise 0.05 mL-(+) tartaric acid in acetone (5.19 ml) at room temperature. Follow the method of example 64 to obtain 110 mg of white solid (Compound 73). The yield is 81.3%.

Elemental analysis: calculated value: C, 54.45; H, 5.45; N, 12.21; O, 27.90, measured value: C, 54.48; H, 5.42; N, 12.23; O, 27.88.

Example 74

(Z)-4-(5-bromo-4-fluoro-2-nitrophenoxy)-2-buten-1-ol (III-2)

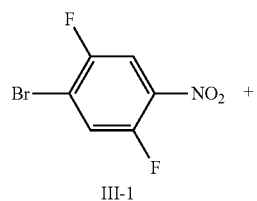

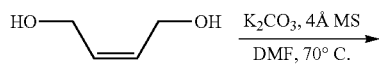

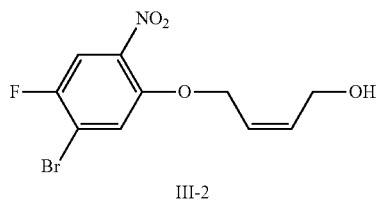

Compound III-1 (8 g, 33.6 mmol) [J. Org. Chem., 1995, 60, 5838] is dissolved in DMF (50 mL), add anhydrous $K_2CO_3$ (23.19 g, 168 mmol) and (Z)-2-Butene-1,4-diol, as well as a small amount of 4 Å molecular sieves (4 Å MS). Allow heated reaction at 70° C. under the protection of nitrogen for 24 hours. TLC (petroleum ether/ethyl acetate=5:1) is used to monitor the reaction. Once the reaction is completed, water (200 mL) is added for dilution, and extract with diethyl ether (60 mL×2). Then merge the organic phases, and wash with water (60 mL) and saturated NaCl solution (50 mL) successively. Afterwards, dry with anhydrous sodium sulfate, conduct filtration, spin-dry and go through column chromatography (petroleum ether/ethyl acetate=5:1), to obtain 6.37 g of light yellow solid (Compound III-2). The yield is 62%.

III-2: $^1$H NMR (300 MHz, CDCl$_3$): δ 7.45 (d ,J=7.71 Hz, 1 H), 7.70 (d, J=5.50 Hz, 1 H), 5.85 (m, 1 H), 5.95 (m, 1 H), 4.80 (d, J=5.78 Hz, 1 H) 4.32 (d, J=5.78 Hz, 1 H).

Example 75

(Z)-4-(2-(benzyloxycarbonylamino)-4-bromo-5-fluorophenoxy)-2-buten-1-ol (III-3)

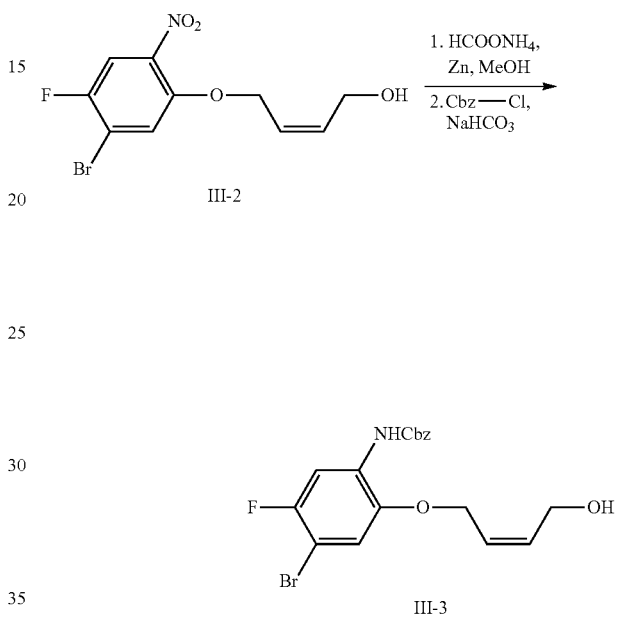

Get Compound III-2 (10 g, 32.7 mmol) and zinc powder (10.6 g), add methanol (120 mL), stir and add ammonium formate (10.3 g, 163 mmol) in batches. Stir at room temperature for 24 hours. TLC (petroleum ether/ethyl acetate=1:1) is used to monitor the reaction. Once the reaction is completed, the reaction solution is filtered and methanol is evaporated. Afterwards, dissolve with ethyl acetate (120 mL) and wash with water (50 ml). Extract with ethyl acetate (30 mL) reversely and merge the ethyl acetate layers, followed by wash with saturated NaCl solution (50 mL) dry ing with anhydrous sodium sulfate, and filtering. The solvent is evaporated to obtain reddish black viscous material and then continue the next step reaction immediately.

The obtained viscous material is dissolved with a mixed solvent of acetone and water (2/1) (150 mL) and cooled by ice-salt bath to below 0° C. Add NaHCO$_3$ (5.49 g, 65.3 mmol) and stir. Add carbobenzoxy chloride CbzCl (6.9 mL, 48.8 mmol) slowly. After addition, warm up to room temperature slowly and stir overnight. TLC (petroleum ether/ethyl acetate=1:1) is used to monitor the reaction. Once the reaction is completed, evaporate acetone and extract with ethyl acetate (50 mL×3), then wash with saturated NaCl solution (300 ml), dry with anhydrous sodium sulfate, go through filtration, spin-dry, and perform column chromatography (petroleum ether/ethyl acetate=5:1), to obtain 7.5 g of white solid (Compound III-3). The yield is 56%.

$^1$HNMR (300 MHz, CDCl$_3$): δ 8.08 (d, J=10.41 Hz, 1 H), 7.32-7.45 (m, 5 H), 6.95 (d, J=6.16 Hz, 1 H), 5.90 (m, 1 H)

5.78 (m, 1 H), 5.20 (s, 2 H), 4.62 (d, J=6.16 Hz, 1 H), 4.30 (d, J=6.16 Hz, 1 H). MS (EI) m/z (%): 91 (100), 409 (M⁺, 3).

Example 76

(−)-(2S,3R)-4-(2-(carbobenzoxyamino)-4-bromo-5z-fluorophenoxy)-2,3-epoxy-1-butanol (III-4)

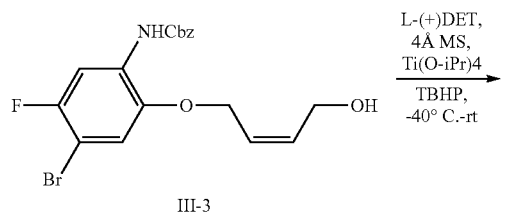

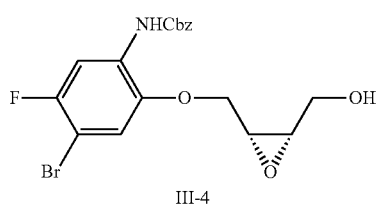

A small amount of activated 4 Å molecular sieves are suspended in dry CH₂Cl₂ (200 mL), and cooled to −40° C. L-(+)-DET (5.02 mL, 29.3 mmol), Ti(Oi-Pr)₄ (8.96 mL, 32.9 mmol) and TBHP (14.8 mL, 48.8 mmol, 3.3 M toluene solution) are added. After 1 hour, add Compound III-3 (10 g, 24.4 mmol to be dissolved in a small amount of dichloromethane), and maintain the reaction at −40° C. for 8 hours. After that, slowly warm up to room temperature and stir overnight. TLC (petroleum ether/ethyl acetate=1:1) is used to monitor the reaction. Once the reaction is completed, 10% L-(+)-tartaric acid aqueous solution (150 mL) is added to the reaction solution. Stir for 2 hours, filter and collect the filtrate. Then wash with water (50 mL), and saturated NaCl solution (50 mL) successively. Organic phases are dried with anhydrous sodium sulfate, and go through filtration. Evaporate the solvent and perform column chromatography (petroleum ether/acetone=3:1), to obtain 8.76 g of white solid (Compound III-4). The yield is 84%.

¹HNMR (300 MHz, CDCl₃): δ 8.10 (d, J=10.01 Hz, 1 H), 7.32-7.45 (m, 5 H), 7.00 (d, J=5.86 Hz, 1 H), 5.20 (s, 2 H), 4.25-4.35 (dd, J₁=3.42 Hz, J₂=11.23 Hz, 1 H). 4.10-4.20 (dd, J₁=6.84 Hz, J₂=11.23 Hz 1 H), 3.82-3.98 (m, 2 H), 3.40-3.50 (m, 1 H), 3.30-3.38 (m, 1 H). MS (EI) m/z (%): 91 (100), 427 (M⁺, 5).

Example 77

(−)-(2S,3R)-1-(tert-butyldimethylsiloxyl)-4-(2-(carbobenzoxy amino)-4-bromo-5-fluorophenoxy)-2,3-epoxybutane (III-5)

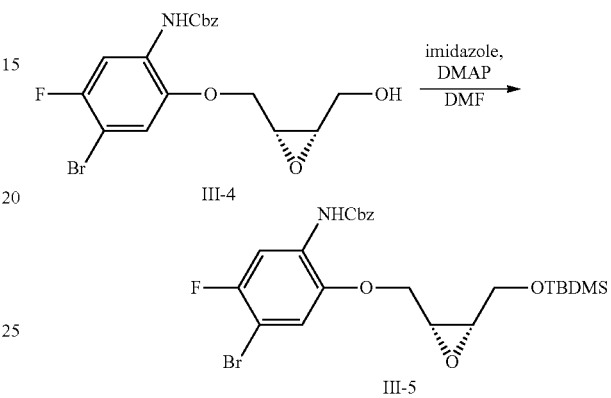

Compound III-4 (8.15 g, 19.1 mmol) is dissolved in DMF (50 mL), and imidazole (2.6 g, 38.3 mmol), 4-dimethylaminopyridine (DMAP) (0.18 g, 1.5 mmol) are added. Cool ice-salt bath to 0° C. Tert-butyldimethylsilyl chloride (TBDMSCl) (3.46 g, 22.9 mmol) is added in batches, then warm up to room temperature and stir for 3 hours. TLC (petroleum ether/ethyl acetate=5:1) is used to monitor the reaction. Once the reaction is completed, water (150 mL) is added to dilute the reaction solution. Extract with CH₂Cl₂ (100 mL×3) and merge the organic phases. Then wash with saturated NaCl solution (50 mL), dry with anhydrous sodium sulfate, go through filtration, spin-dry and perform column chromatography (petroleum ether/ethyl acetate=8:1), to obtain 9.16 g of light yellow viscous liquid (Compound III-5). The yield is 88.6%.

¹HNMR (300 MHz, CDCl₃): δ 8.10 (d, J=10.26 Hz, 1 H), 7.32-7.45 (m, 5 H), 7.00 (d, J=6.15 Hz, 1 H), 5.20 (s, 2 H), 4.25-4.35 (dd, J₁=2.93 Hz, J₂=11.14 Hz, 1H), 4.10 (m, 1 H), 3.80 (m, 2 H), 3.38 (m, 1 H), 3.28 (m, 1 H). MS (EI) m/z (%): 91 (100), 541 (M⁺, 1).

Example 78

(−)-(3R,3aS)-7-bromo-3-((tert-butyldimethylsiloxyl) methyl)-8-fluoro-3a,4-dihydro benzo[b]oxazole-[3,4-d][1,4]oxazin-1 (3H)-one (III-6)

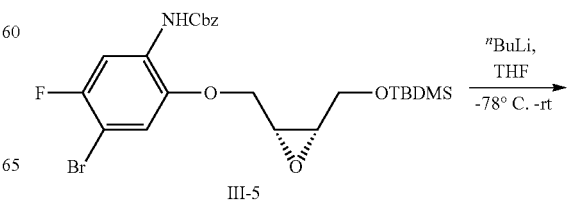

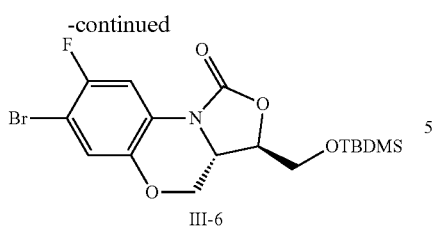

Compound III-5 (9.3 g, 17.2 mmol) is dissolved in dry THF (200 mL) and cooled to −78° C. Add dropwise n-butyl lithium ("BuLi) and after addition is completed, stir for 2 hours, then slowly warm up to room temperature, and stir overnight. TLC (petroleum ether/ethyl acetate=5:1) is used to monitor the reaction. Once the reaction is completed, add saturated NH$_4$Cl solution (50 mL), stir and evaporate THF. Add water (50 mL) for dilution, extract with CH$_2$Cl$_2$C (80 mL×3) and merge the organic phases, then wash with water (50 mL) and saturated NaCl solution (50 mL), successively. Afterwards, dry with anhydrous sodium sulfate and go through filtration. Evaporate the solvent, and perform column chromatography (petroleum ether/ethyl acetate=10:1), to obtain 5.6 g of white solid (Compound III-6). The yield is 75.0%.

$^1$HNMR (300 MHz, CDCl$_3$): δ 7.80 (d, J=10.01 Hz, 1 H), 6.90 (m, 1 H), 4.45 (dd, J$_1$=2.93 Hz, J$_2$=10.50 Hz, 1 H), 4.25-4.33 (m, 1 H), 4.08-4.15 (m, 1 H), 3.80-3.95 (m, 3 H), 0.90 (s, 15 H). MS (EI) m/z (%): 296 (100), 431 (M$^+$, 1).

Example 79

(3R,3aS)-7-bromo-3-(hydroxymethyl)-8-fluoro-3a,4-dihydrobenzo[b]oxazole-[3,4-d][1,4]oxazin-1(3H)-one (III-7)

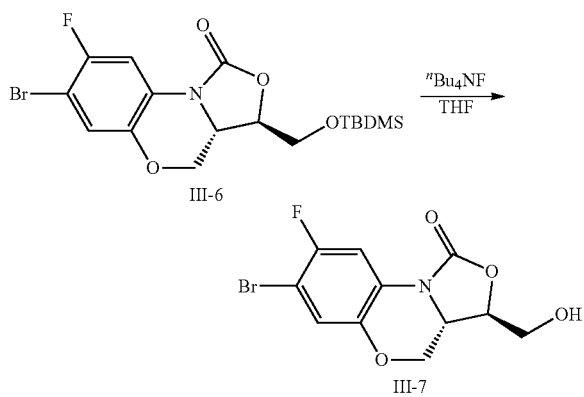

Compound III-6 (4.9 g, 11.3 mmol) is dissolved in THF (50 mL) and cooled to 0° C. Add tetra-n-butylammonium fluoride "Bu$_4$NF.3H$_2$O (3.57 g, 11.3 mmol) slowly, warm up to room temperature, and stir for 4 hours. TLC (petroleum ether/ethyl acetate=1:1) is used to monitor the reaction. Once the reaction is completed, evaporate THF and add water (20 mL) for dilution, extract with CH$_2$Cl$_2$ (30 mL×3) and merge the organic phases, then wash with saturated NaCl solution (30 mL), dry with anhydrous sodium sulfate, and go through filtration. Spin-dry and perform column chromatography (petroleum ether/ethyl acetate=5:1 to 3:1), to obtain 3.0 g of light yellow viscous solid (Compound III-7). The yield is 83.2%.

$^1$HNMR (300 MHz, CDCl$_3$): δ 7.80 (d, J=9.88 Hz, 1 H), 6.90 (m, 1 H), 4.45 (dd, J$_1$=2,29 Hz, J$_2$=6.77 Hz, 1 H), 4.30-4.40 (m, 1 H), 4.15-4.25 (m, 1 H), 4.00-4.10 (dd, J$_1$=3.66 Hz, J$_2$=12.62 Hz 2 H), 3.80-3.95 (m, 2 H), 2.03 (s, 1 H). MS (EI) m/z (%): 239 (100), 317 (M$^+$, 3).

Example 80

((3R,3aS)-7-bromo-8-fluoro-1-oxo-1,3,3a,4-tetrahydrobenzo[b]oxazole-[3,4-d][1,4]oxazin-3-yl)-3-nitrobenzenesulfonate (III-8)

Compound III-7 (2.75 g, 8.65 mmol) is dissolved in CH$_2$Cl$_2$ (50 mL). Cool ice-salt bath to 0° C., add triethylamine (5 mL), add dropwise m-nitrobenzenesulfonyl chloride (NOSCl) (2.3 g, 10.4 mmol) in CH$_2$Cl$_2$ (10 mL). After addition is completed, the ice-salt bath is removed, and stir at room temperature overnight. TLC (petroleum ether/ethyl acetate=1:1) is used to monitor the reaction. After the reaction is completed, the reaction solution is washed with water (30 mL) and saturated NaCl solution (30 mL) successively. Then dry with anhydrous sodium sulfate and go through filtration. Evaporate the solvent and perform column chromatography (CH$_2$Cl$_2$), to obtain 3.8 g of white powdery solid (Compound III-8). The yield is 87.3%.

$^1$HNMR (300 MHz, CDCl$_3$): δ 8.80 (s, 1 H), 8.59 (d, J=8.20 Hz, 1 H), 8.26 (d, J=7.32 Hz, 1 H), 7.89 (t, J=8.21 Hz, 1 H), 7.80 (d, J=9.38 Hz, 1 H), 7.19 (d, J=6.45 Hz, 1 H), 4.40-4.50 (m, 4 H), 4.10-4.17 (m, 1 H), 3.81-3.90 (t, J=10.26 Hz, 1 H). MS (EI): m/z (%): 424 (100), 502 (M$^+$, 44).

Example 81

(((3R,3aS)-7-bromo-8-fluoro-1-oxo-1,3,3a,4-tetrahydrobenzo[b]oxazole-[3,4-d][1,4]oxazin-3-yl)methyl) acetamide (II-2)

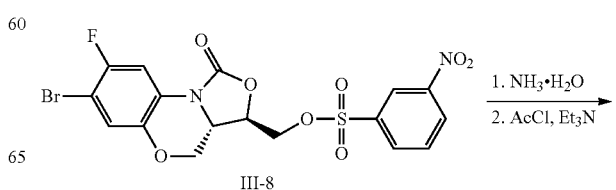

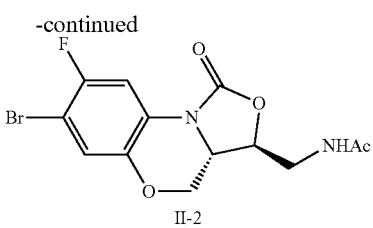

Compound III-8 (2.68 g, 5.3 mmol) is dissolved in a mixed solvent (150 mL) of acetonitrile and isopropanol (2:1) and heated to 50° C. Add stronger ammonia water $NH_3 \cdot H_2O$ (40 mL) and allow reaction for 24 hours. TLC (dichloromethane/methanol=20:1) is used to monitor the reaction. After the reaction is completed, evaporate ammonia gas and organic solvent, extract with $CH_2Cl_2$ (50 mL×2) and merge the organic phases, then wash with saturated NaCl solution (30 ml), dry with anhydrous sodium sulfate, and evaporate the solvent, to obtain orange-red oily substance. Then continue the next step reaction immediately.

The resulting product from the step above is dissolved in $CH_2Cl_2$ (80 mL). Cool ice-salt bath to 0° C., add triethylamine (5 mL), and add acetyl chloride AcCl (5 mL) in $CH_2Cl_2$ (20 mL) slowly. After addition is completed, warm up to room temperature, and stir for 0.5 hours. TLC (dichloromethane/methanol=20:1) is used to monitor the reaction. After the reaction is completed, the reaction solution is washed with water (30 mL) and saturated NaCl solution (30 mL) successively. Then dry with anhydrous sodium sulfate, go through filtration, spin-dry and perform column chromatography, to obtain 1.22 g of white solid (Compound II-2). The yield is 63.7%.

$^1$HNMR (300 MHz, $CDCl_3$): δ 7.80 (d, J=9.61 Hz. 1 H), 7.19 (d, J=6.32 Hz, 1 H), 6.18 (br s, 1 H), 4.50-4.60 (dd, $J_1$=3.02 Hz, $J_2$=7.14 Hz, 1 H), 4.40-4.50 (m, 1 H), 3.93 (t, J=9.88 Hz,1H), 3.70-3.89 (m, 3 H), 2.10 (s, 3 H). MS (EI): m/z (%): 221 (100),358 ($M^4$, 15).

Example 82

((3R,3aS)-7-bromo-1-oxo-1,3,3a,4-tetrahydrobenzo[b]oxazole-[3,4-d][1,4]oxazin-3-yl)-3-nitrobenzenesulfonate (IV-2)

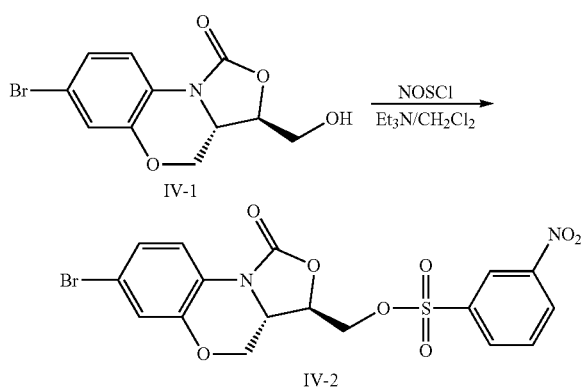

Compound IV-1 (5.96 g, 20 mmol) [J. Heterocyclic Chem., 43, 2006, 1071.] is dissolved in $CH_2Cl_2$ (100 mL). Cool ice-salt bath to 0° C., add triethylamine (5 mL), and add dropwise m-nitrobenzenesulfonyl chloride (4.6 g, 20.8 mmol) in $CH_2Cl_2$ (20 mL). After addition is completed, the ice-salt bath is removed, and stir at room temperature overnight. TLC (petroleum ether/ethyl acetate=1:1) is used to monitor the reaction. After the reaction is completed, the reaction solution is washed with water (100 mL) and saturated NaCl solution (100 mL) successively. Then dry with anhydrous sodium sulfate and go through filtration. Evaporate the solvent and perform column chromatography ($CH_2Cl_2$), to obtain 7.51 g of light yellow powdery solid (Compound IV-2). The yield is 77.2%.

$^1$HNMR (300 MHz, $CDCl_3$): δ 8.80 (s, 1 H), 8.59 (d, J=8.20 Hz, 1 H), 8.26 (d, J=7.32 Hz, 1 H), 7.89 (t, J=8.21 Hz, 1 H), 7.10-7.32 (m, 3 H), 4.40-4.55 (m, 4 H), 4.10-4.18 (m, 1 H), 3.85 (t, J=10.26 Hz, 1 H). MS (ESI): m/z: 486.2 $(M+1)^+$.

Example 83

(3R,3aS)-7-bromo-3-(azidomethyl)-3a,4-dihydrobenzo[b]oxazole-[3,4-d][1,4]oxazin-1(3H)-one (IV-3)

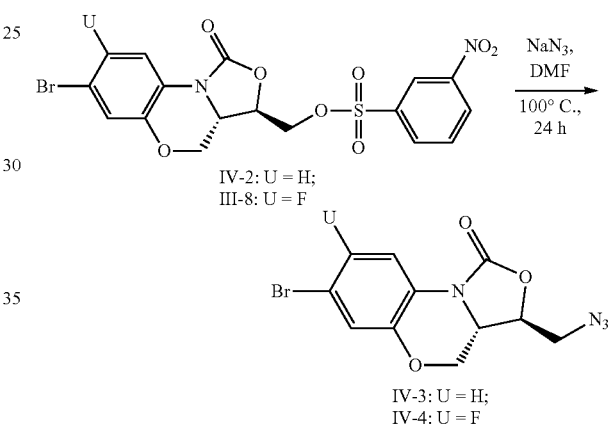

IV-2: U = H;
III-8: U = F

IV-3: U = H;
IV-4: U = F

Compound IV-2 (4.86 g, 10 mmol) is dissolved in dry DMF (5 mL), add sodium azide ($NaN_3$) (0.92 g, 20 mmol), and allow heated reaction at 100° C. under protection of nitrogen for 24 hours. TLC ($CH_2Cl_2$/MeOH=100:1) is used to monitor the reaction. Upon completion of the reaction, water (200 mL) is added for dilution, and extract with dichloromethane (100 mL×2). The merged dichloromethane layers are washed with water (200 mL) and saturated NaCl solution (200 mL) successively. Then dry with anhydrous sodium sulfate and go through filtration. Evaporate the solvent, and perform column chromatography ($CH_2Cl_2$/MeOH=100:1), to obtain 3.01 g of white powdery solid (Compound IV-3). The yield is 93.1%.

$^1$HNMR (300 MHz, $CDCl_3$): δ 7.80 (d, J=9.88 Hz, 1 H), 6.90-7.10 (m, 2 H), 4.45 (dd, $J_1$ 2.29 Hz, $J_2$=6.77 Hz, 1 H), 4.30-4.44 (m, 1 H), 4.15-4.25 (m, 1 H), 4.00-4.12 (dd, $J_1$=3.66 Hz, $J_2$=11.15 Hz 2 H), 3.80-3.95 (m, 2 H), 2.05 (s, 1 H). MS (ESI) m/z: 325.0 $(M+1)^+$.

(3R,3aS)-7-bromo-3-(azidomethyl)-8-fluoro-3a,4-dihydrobenzo[b]oxazole-[3,4-d][1,4]oxazin-1(3H)-one (IV-4)

Compound III-8 (5.03 g, 10 mmol) is dissolved in dry DMF (5 mL), add sodium azide (0.92 g, 20 mmol). Follow the method described above to obtain 3.12 g of white powdery solid (Compound IV-4). The yield is 91%.

¹HNMR (300 MHz, CDCl₃):δ 7.80 (d, J=9.78 Hz, 1 H), 6.90 (m, 1 H), 4.45 (dd, $J_1$=2.28 Hz, $J_2$=6.98 Hz, 1 H), 4.30-4.40 (m, 1 H), 4.15-4.25 (m, 1 H), 4.00-4.10 (dd, $J_1$=3.66 Hz, $J_2$=11.12 Hz 2 H), 3.80-3.95 (m, 2 H), 2.05 (s, 1 H). MS (ESI) m/z: 343.0 (M+1)⁺.

Example 84

(3R,3aS)-3-(1H-1,2,3-triazol-1-yl)methyl)-3a,4-dihydrobenzo oxazole-[3,4-d][1,4]oxazin-1(3H)-one (II-5)

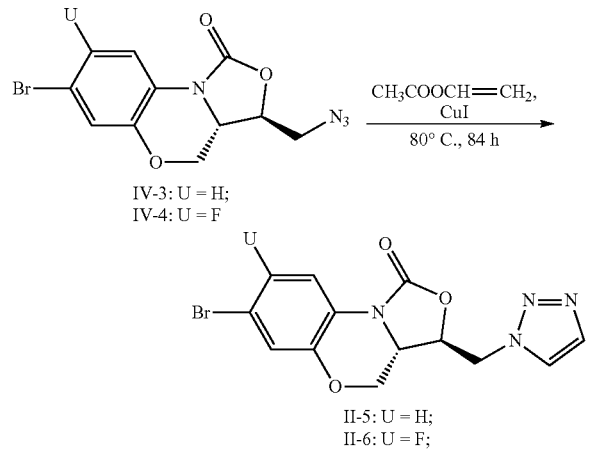

IV-3: U = H;
IV-4: U = F

II-5: U = H;
II-6: U = F;

Compound IV-3 (3.24 g, 10 mmol) is dissolved in vinyl acetate (CH₃COOCH=CH₂) (100 mL). Add cuprous iodide CuI (60 mg) and allow heated reflux reaction under the protection of nitrogen for 84 hours. TLC (CH₂Cl₂/MeOH=50:1) is used to monitor the reaction. Upon completion of the reaction, vinyl acetate is evaporated to dryness under decompression, and the residue is dissolved with dichloromethane (100 mL). The solution is washed with water (100 mL)/saturated NaCl solution (100 mL) successively. Then dry with anhydrous sodium sulfate and go through filtration. Evaporate the solvent and perform column chromatography (CH₂Cl₂/MeOH=50:1), to obtain 2.54 g of white powdery solid (Compound II-5). The yield is 71.7%.

¹H NMR (300 MHz, CDCl₃): δ 7.95 (dd, $J_1$=1.71 Hz, $J_2$=7.82 Hz, 1 H), 7.80 (s, 1 H), 7.72 (s, 1 H), 6.92-7.10 (m, 3 H), 4.73 (dd, $J_1$=1.44 Hz, $J_2$=4.96 Hz, 2 H), 4.68 (m, 1 H), 4.45 (dd, $J_1$=3.05 Hz, $J_2$=10.12 Hz, 1 H), 4.05 (m, 1 H), 3.94 (d, J=10.12 Hz, 1 H), MS (ESI) m/z (%): 351.0 (M+1)⁺.

(3R,3aS)-8-fluoro-3-((1H-1,2,3-triazol-1-yl)methyl)-3a,4-dihydrobenzo[b]oxazole-[3,4-d][1,4]oxazin-1(3H)-one (II-6)

Compound IV-4 (3.43 g, 10 mmol) is dissolved in vinyl acetate (100 mL) and add cuprous iodide (65 mg). Follow the method described above to obtain 2.58 g of white powder (Compound II-6). The yield is 70%.

¹H NMR (300 MHz, CDCl₃): δ 7.95 (dd, $J_1$=1.71 Hz, $J_2$=7.82 Hz, 1 H), 7.81 (s, 1 H), 7.72 (s, 1 H), 6.92-7.10 (m, 2 H), 4.74 (dd, $J_1$=1.47 Hz, $J_2$=4.96 Hz, 2 H), 4.68 (m, 1 H), 4.45 (dd, $J_1$=3.05 Hz, $J_2$=10.12 Hz, 1 H), 4.03 (m, 1 H), 3.92 (d, J=10.12 Hz, 1 H), MS (ESI) m/z (%): 369.0 (M+1)⁺.

II. Experimental Examples

1. In Vitro Antibacterial Activity Experiment of Preferred Compounds

Test method: minimal inhibitory concentration (MIC) of series of compounds of the present invention and the positive control drug linezo lid against the tested strains was determined using agar dilution method (Antimicrob. Agents and Chemother., 40, 1996. 720-726). The bacteria was inoculated on the surface of agar plates with different drug concentrations using a multi-point inoculation instrument (Denley A400). Inoculum of each point was about 10⁶ CFU/mL, and inoculation was performed at 35° C. for 16 hours to get observation. The minimal concentration of a drug contained in the plate medium without bacteria growth was considered as the minimal inhibitory concentration (MIC value) of the drug against bacteria.

Tested strains: the tested strains were clinically isolated pathogenic bacteria collected in the Nanjing area, and re-identified by conventional methods before use. 31 pathogenic bacteria are selected, and strain serial numbers were as following: six enterococci; five Staphylococcus aureus sensitive strains; five Staphylococcus epidermidis sensitive strains; six Staphylococcus aureus drug-resistant strains; five Staphylococcus epidermidis drug-resistant strains; four pneumococcus drug-resistant strains.

At first, tested compounds were added into 2 mL of DMSO, which could facilitate full dissolution, and then sterile double distilled water was added to a desired concentration; 20 mL MH medium in heat-melted to liquid was added to each of plates with drug solution, so that the final drug concentrations in the plates were 64, 32, 16, 8, 4, 2, 1, 0.5, 0.25, 0.125, 0.0625 and 0.031 µg/mL.

The positive control group was LZ (linezolid, trade name Zyvox, which was approved by the FDA in 2000 to be first launched in the United States and is the first and only oxazolidinone antibacterial drug permitted to be used in clinical practice at present).

The activity data of some compounds against the tested strains are shown in Table 3.

TABLE 3

| | | | | | | |
|---|---|---|---|---|---|---|
| | | | | Staphylococcus aureus drug-resistant strain (6 strains) | Staphylococcus epidermidis drug-resistant strain (5 strains) | Pneumococcus drug-resistant strain (4 strains) |
| Compound | Enterococcus (6 strains) | Staphylococcs aureus sensitive strain (5 strains) | Staphylococcus epidremidis sensitive strain (5 strains) | | | |
| 1 | 2 | 0.5 | 0.5 | 0.5 | 1 | 0.5 |
| 3 | 1 | 0.25 | 0.5 | 0.5 | 0.5 | 1 |
| 4 | 1 | 0.25 | 0.5 | 0.5 | 0.5 | 1 |
| 5 | 1 | 0.25 | 0.5 | 0.5 | 0.5 | 0.5 |
| 7 | 0.5 | 0.125 | 0.25 | 0.25 | 0.25 | 0.25 |
| 8 | 1 | 0.25 | 0.5 | 0.5 | 0.5 | 0.5 |

MIC values of some compounds against the tested strains (µmol/mL)

TABLE 3-continued

MIC values of some compounds against the tested strains (μmol/mL)

| Compound | Enterococcus (6 strains) | Staphylococcs aureus sensitive strain (5 strains) | Staphylococcus epidremidis sensitive strain (5 strains) | Staphylococcus aureus drug-resistant strain (6 strains) | Staphylococcus epidermidis drug-resistant strain (5 strains) | Pneumococcus drug-resistant strain (4 strains) |
|---|---|---|---|---|---|---|
| 9  | 0.5  | 0.25  | 0.25  | 0.25  | 0.5   | 0.25 |
| 14 | 0.5  | 0.125 | 0.25  | 0.25  | 0.25  | 0.5  |
| 16 | 2    | 0.5   | 0.5   | 0.5   | 0.5   | 1    |
| 18 | 2    | 0.5   | 0.5   | 0.5   | 0.5   | 1    |
| 23 | 0.5  | 0.25  | 0.25  | 0.5   | 0.5   | 0.5  |
| 24 | 0.5  | 0.5   | 0.5   | 0.5   | 0.5   | 0.5  |
| 31 | 0.5  | 0.5   | 0.25  | 0.5   | 0.25  | 0.5  |
| 33 | 0.5  | 0.25  | 0.25  | 0.25  | 0.25  | 0.5  |
| 35 | 0.5  | 0.5   | 0.25  | 0.25  | 0.25  | 0.5  |
| 36 | 0.5  | 0.5   | 0.25  | 0.25  | 0.25  | 0.5  |
| 41 | 0.25 | 0.25  | 0.125 | 0.125 | 0.125 | 0.25 |
| 44 | 1    | 0.5   | 0.5   | 0.5   | 0.5   | 0.5  |
| 45 | 1    | 0.5   | 0.25  | 0.5   | 0.25  | 1    |
| 46 | 0.5  | 0.5   | 0.25  | 0.25  | 0.25  | 0.5  |
| 47 | 0.5  | 0.5   | 0.25  | 0.25  | 0.25  | 0.5  |
| 49 | 0.5  | 0.5   | 0.25  | 0.25  | 0.25  | 0.5  |
| 51 | 0.5  | 0.25  | 0.5   | 0.5   | 0.5   | 0.5  |
| 58 | 0.5  | 0.25  | 0.25  | 0.25  | 0.25  | 0.5  |
| 60 | 1    | 0.5   | 0.5   | 0.5   | 0.5   | 0.5  |
| 61 | 0.5  | 0.25  | 0.25  | 0.25  | 0.25  | 0.5  |
| 62 | 0.5  | 0.5   | 0.5   | 0.5   | 0.5   | 0.5  |
| LZ | 1    | 1     | 1     | 1     | 1     | 2    |

As seen in the data from Table 3, the compounds of the present invention have strong in vitro antibacterial activity, which is significantly superior to the positive control drug LZ. Particularly, the antibacterial activity of compounds 7, 14, 41, 47, 49, 58, and 61 against all the tested bacteria is 4-8 times stronger than that of the control drug LZ, and there are excellent biological activity and drugability.

2. In Vivo Pharmacokinetic Trial of the Preferred Compounds in Rat

The tested compound was Compound 7, using two administration routes (gavage and intravenous injection).

Gavage: four healthy SD male rats weighing 200-250 g were given a dose of 15 mg/kg, with an administered volume of 10 mL/kg. And the compound was prepared as 0.5% CMC—Na. The animals were fasted for 12 hours and had free access to water before administration, 0.3 mL of venous blood was sampled through retrobulbar venous plexus at 0.25, 0.5, 1, 0, 2.0, 3.0, 4.0, 5.0, 7.0, 9.0, 24, and 48 hours after administration and collected in heparinized test tubes, which is subjected to centrifugation at 3500 rpm for 10 min to separate the plasma, and stored at −20° C. for testing.

Intravenous injection: two healthy SD male rats weighing 200-250 g were given a dose of 15 mg/kg, with an administered volume of 10 mL/kg. And the compound was prepared using DMSO, Tween 80 and deionized water. The animals were fasted for 12 hours and had free access to water before administration, 0.3 mL of venous blood was sampled through retrobulbar venous plexus at 5 min, 15 min, 0.5, 1.0, 2.0, 3.0, 4.0, 5.0, 7.0, 9.0, 24, and 48 hours after administration and collected in heparinized test tubes, which is subjected to centrifugation at 3500 rpm for 10 min to separate the plasma, and stored at −20° C. for testing.

Concentration of Compound 7 in plasma was determined using liquid chromatography-tandem mass spectrometry. Experimental test instruments are shown in Table 4.

TABLE 4

| | Experimental instruments |
|---|---|
| Liquid chromatography system: | Agilent 1200 liquid chromatography system (including G1322A-type binary infusion pump, G1316B-type column oven and G1312B-type vacuum degasser), Agilent, USA |
| automatic sampler: | Model G1367D-type sampler, Agilent, USA |
| MS/MS system: | Agilent 6460-type triple quadrupole tandem mass spectrometer, equipped with an electrospray ionization source (ESI source), Agilent, USA |
| Data acquisition: | Mass Hunter Data Acquistion software, version B.01.04, Agilent, USA |

After Compound 7 was given among rats by gavage and intravenous injection, the pharmacokinetic parameters were shown in Table 5.

TABLE 5

The pharmacokinetic parameters after 15 mg/kg of Compound 7 was given among rats by gavage and intravenous injection

| Routes | Animal No. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | CLz (L/h/kg) | Vz (L/kg) | F (%) |
|---|---|---|---|---|---|---|---|---|---|---|
| Gavage | 1 | 4.0 | 3958 | 57191 | 57255 | 8.65 | 4.74 | 0.262 | 1.79 | |
|  | 2 | 5.0 | 4772 | 61593 | 61983 | 8.79 | 6.36 | 0.242 | 2.22 | |
|  | 3 | 5.0 | 6269 | 79448 | 79622 | 9.09 | 5.31 | 0.188 | 1.44 | |

TABLE 5-continued

The pharmacokinetic parameters after 15 mg/kg of Compound 7 was given among rats by gavage and intravenous injection

| Routes | Animal No. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | CLz (L/h/kg) | Vz (L/kg) | F (%) |
|---|---|---|---|---|---|---|---|---|---|---|
| | 4 | 2.0 | 5454 | 66900 | 67083 | 7.96 | 5.60 | 0.224 | 1.81 | |
| | Mean | 4.0 | 5113 | 66283 | 66486 | 8.62 | 5.50 | 0.229 | 1.82 | 81.2% |
| | SD | 1.4 | 984 | 9633 | 9633 | 0.48 | 0.68 | 0.031 | 0.32 | |
| Intravenous | 5 | 2.0 | 7513 | 76057 | 76212 | 7.98 | 5.44 | 0.197 | 1.55 | |
| injection | 6 | 2.0 | 7513 | 87218 | 87475 | 8.77 | 5.72 | 0.171 | 1.42 | |
| | Mean | 2.0 | 7513 | 81637 | 81844 | 8.37 | 5.58 | 0.184 | 1.48 | |
| | SD | 0.0 | 0 | 7892 | 7964 | 0.56 | 0.20 | 0.018 | 0.09 | |

As seen from Table 5, Compound 7 of the present invention has good metabolic properties, and various metabolic parameters are very satisfactory. When calculated as $AUC_{0-t}$, the absolute bioavailability of gavage administration of 15 mg/kg Compound 7 is 81.2%.

3. Determination of In Vivo Antibacterial Activity of Preferred Compounds

Experimental strains: the bacteria used for infecting animals was methicillin-resistant *Staphylococcus aureus* (MRSA), which was clinically isolated pathogenic bacteria collected in Nanjing area in 2009, and re-identified by the API method.

Experimental animals: Healthy Kunming mice of SPF grade and weighing 18-22 g were chosen, and male and female were 50% each, and they were supplied by animal breeding office of Pharmacology Laboratory, China Pharmaceutical University.

Test method of infection and treatment: The experimental animals were evenly grouped by sex and weight, each group had 10 mice, including 50% of male and female, respectively. Intraperitoneal injection of bacteria solution was performed among animals at 0.5 mL/animal. One hour after infection, the tested drug solution (Compound 7 of the present invention and the positive control drug LZ) of different concentrations were given to each animal by oral gavage or intravenous injection at 0.5 mL/20 g, respectively. For mice receiving oral gavage, another gavage was given 4 hours after the first dose, observation was performed after administration, and death was recorded. An infected control group was set up for the same group, and the number of the deaths within seven days after infection was recorded.

Experimental data processing: median effective dose $ED_{50}$ and 95% confidence limits were calculated by Bliss for in vivo protective effect of each tested drug among mice infected with tested strain. The experimental results are shown in Table 6.

TABLE 6

Results of in vivo antibacterial experiment on Compound 7

| Bacteria | Compound | Route of administration | $ED_{50}$ (mg/kg) | 95% confidence limit: |
|---|---|---|---|---|
| MRSA | 7 | p.o | 5.92 | 5.21-15.41 |
| | | iv | 5.53 | 4.48-19.90 |
| MRSA | LZ | p.o | 8.50 | 5.64-14.26 |
| | | iv | 8.51 | 5.64-14.26 |

As seen from table 6, in mouse model infected with drug-resistant bacteria MRSA, median effective dose $ED_{50}$ of tested Compound 7 is significantly lower than that of control drug LZ, which clearly demonstrates that Compound 7 has a outstanding therapeutic effect on mouse infected by drug-resistant bacteria MRSA, and its in vivo activity is significantly better than that of the control drug LZ, as well as is more effective.

The compounds of the present invention have novel chemical structure, significantly better in vitro and in vivo antibacterial activity than drug LZ, as well as ideal pharmacokinetic properties and druggability. Thus compounds of the present invention can be used as medication for treatment of infectious diseases, particularly for treatment of infectious diseases caused by drug-resistant bacteria.

The invention claimed is:

1. Benzoxazine oxazolidinone compounds represented by the formula (I), optical isomers or pharmaceutically acceptable salts thereof,

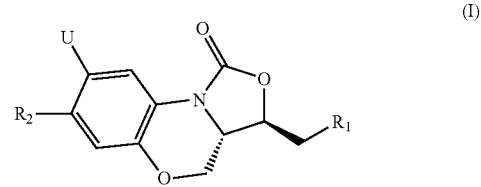

(I)

Wherein:
U is H or F;
$R_1$ is

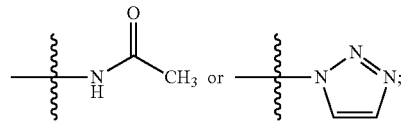

$R_2$ is a phenyl group, or a five membered or six membered aromatic or non-aromatic heterocyclic group;
said phenyl group is optionally substituted by F, —CN, —NH$_2$, or C$_1$-C$_3$ alkylcarbonyl group;
said five membered or six membered aromatic or non-aromatic heterocyclic group comprises at least one heteroatom selected from N, O or S;
Said five membered or six membered aromatic or non-aromatic heterocyclic group may optionally be substituted by the following functional groups: F, Cl, Br, —OH, —NO$_2$, —CHO, —CN, —NH$_2$, —CF$_3$, —C≡CH, —C≡CCH$_2$OH, —COOH, —OR$_3$, —NHCOR$_3$, —COR$_3$; —CONR$_3$R$_4$, and —COOR$_3$, wherein each of R$_3$ and R$_4$ can independently be a C$_1$-C$_3$ alkyl;
or said five membered or six membered aromatic or non-aromatic heterocyclic group may optionally be substituted by $C_1$-$C_6$ straight chain or branched chain alkyl group, or $C_3$-$C_6$ cycloalkyl group, and said $C_1$-$C_6$ straight chain or branched chain alkyl group or $C_3$-$C_6$ cycloalkyl group may optionally be substituted by —OH, —CN, or —NH$_2$;

or said five membered or six membered aromatic or non-aromatic heterocyclic group may optionally be substituted by five membered or six membered aromatic or non-aromatic heterocyclic group, which comprises at least one heteroatom selected from N and O and is either unsubstituted or substituted by $C_1$-$C_3$ alkyl or oxygen.

2. Benzoxazine oxazolidinone compounds represented by the formula (I), optical isomers or pharmaceutically acceptable salts thereof according to claim 1, wherein said five membered or six membered aromatic or non-aromatic heterocyclic group comprises 1 to 2 N atoms;

Said five membered or six membered aromatic or non-aromatic heterocyclic group may optionally be substituted by the following functional groups: F, Cl, Br, —OH, —NO$_2$, —CHO, —CN, —NH$_2$, —CF$_3$, —C≡CH, —C≡CCH$_2$OH, —COOH, —OR$_3$, —NHCOR$_3$, —COR$_3$; —CONR$_3$R$_4$, and —COOR$_3$, wherein each of R$_3$ and R$_4$ can independently be $C_1$-$C_3$ alkyl;

or said five membered or six membered aromatic or non-aromatic heterocyclic group may optionally be substituted by $C_1$-$C_6$ straight chain or branched chain alkyl group, or $C_3$-$C_6$ cycloalkyl group, and said $C_1$-$C_6$ straight chain or branched chain alkyl group or $C_3$-$C_6$ cycloalkyl group may optionally be substituted by —OH, —CN, or —NH$_2$;

or said five membered or six membered aromatic or non-aromatic heterocyclic group may optionally be substituted by five membered or six membered aromatic or non-aromatic heterocyclic group, which contains at least one heteroatom selected from N and O and is either unsubstituted or substituted by $C_1$-$C_3$ alkyl or oxygen.

3. Benzoxazine oxazolidinone compounds represented by the formula (I), optical isomers or pharmaceutically acceptable salts thereof according to claim 1, wherein said five membered or six membered aromatic or non-aromatic heterocyclic group is furyl, thienyl, pyrrolyl, imidazolyl, thiazolyl, pyrazolyl, isothiazolyl, isoxazolyl, pyridyl, pyrimidinyl, pyridazinyl, pyrazinyl, triazolyl or tetrazolyl group.

4. Benzoxazine oxazolidinone compounds represented by the formula (I), optical isomers or pharmaceutically acceptable salts thereof according to claim 1, wherein, U represents H, R$_1$ is NHAc, R$_2$ is

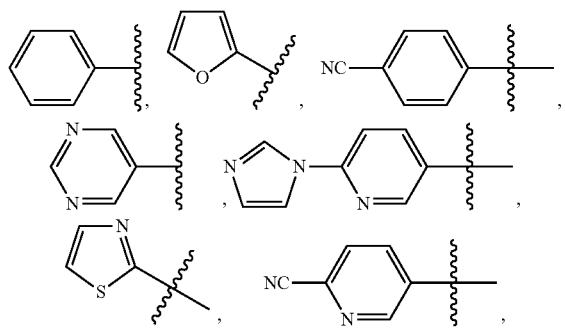

-continued

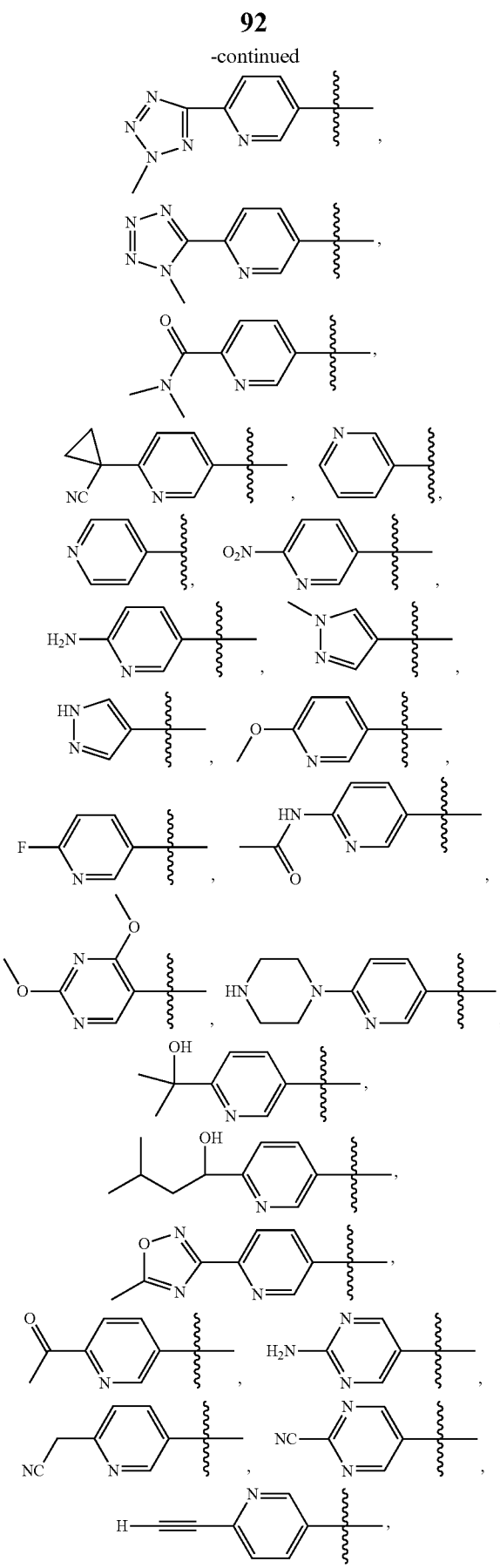

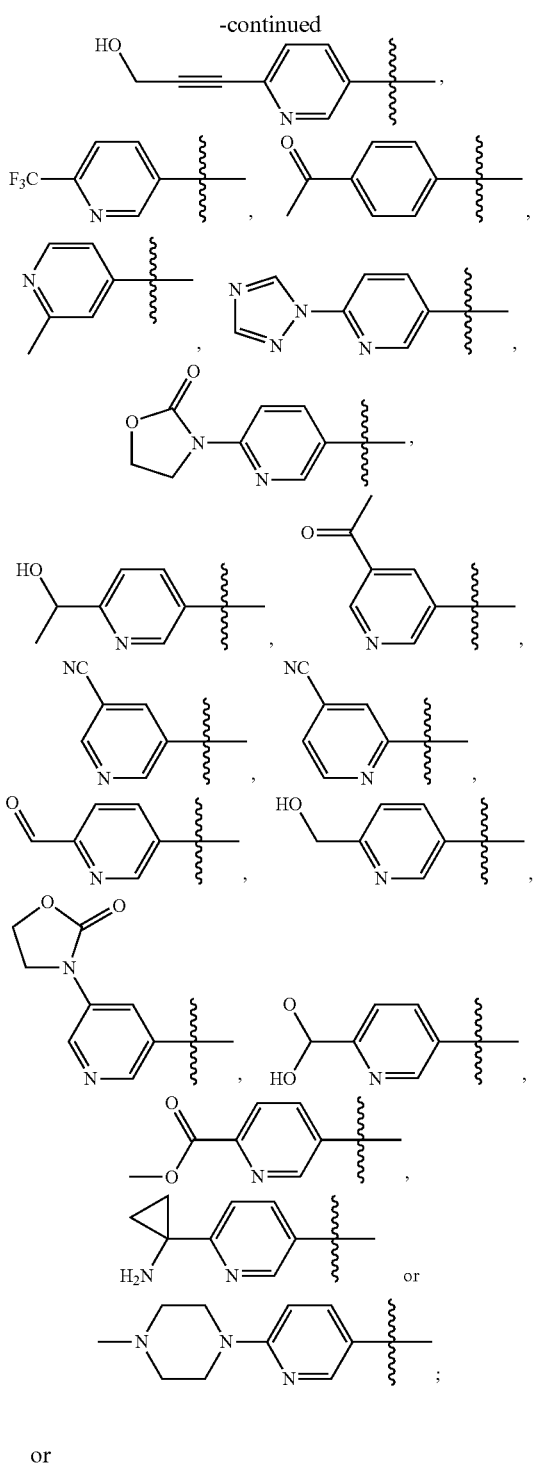
or
U is F, $R_1$ is NHAc, $R_2$ is
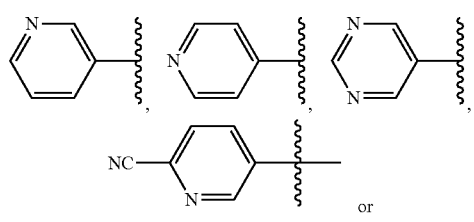
or
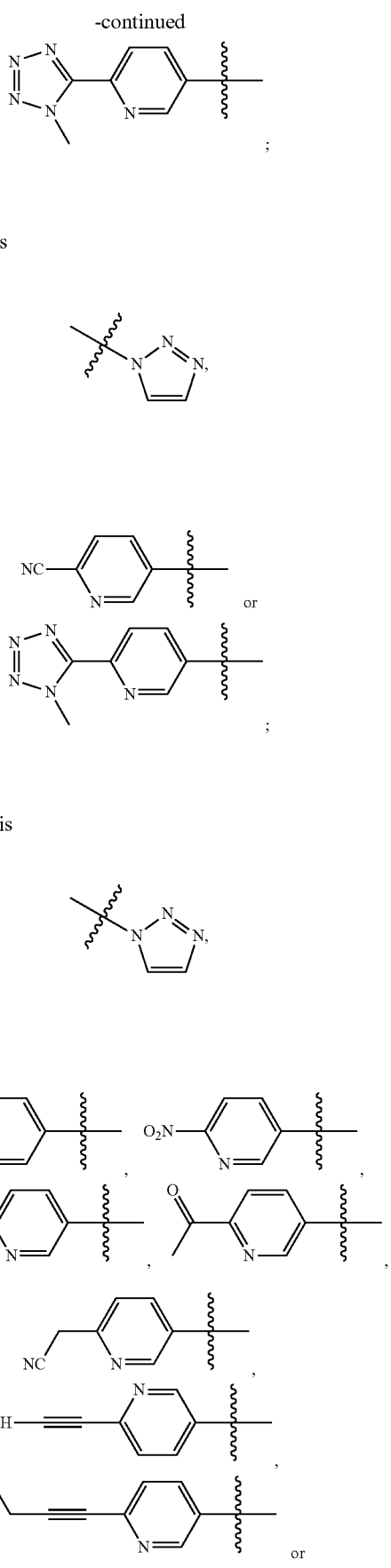

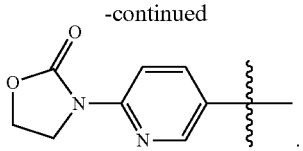

5. Benzoxazine oxazolidinone compounds represented by the formula (I), optical isomers or pharmaceutically acceptable salts thereof according to claim 1, wherein pharmaceutically acceptable salt of benzoxazine oxazolidinone compounds represented by the formula (I) is addition salt with hydrochloric acid, hydrobromic acid, hydrofluoric acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, benzenesulfonic acid, aspartic acid or glutamic acid.

6. Benzoxazine oxazolidinone compounds represented by the formula (I), optical isomers or pharmaceutically acceptable salts thereof according to claim 5, wherein said pharmaceutically acceptable salt of compounds is:

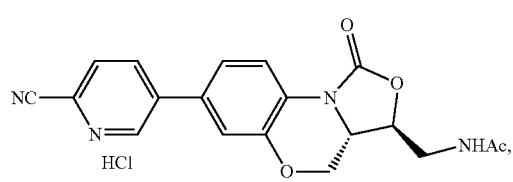

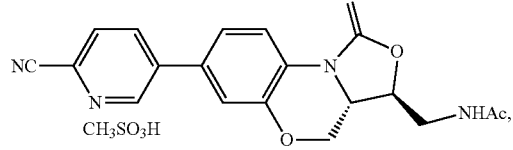

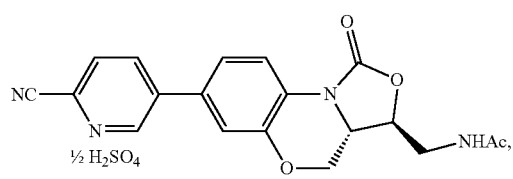

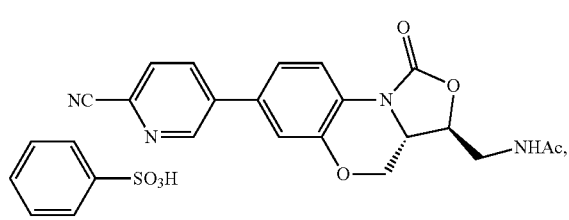

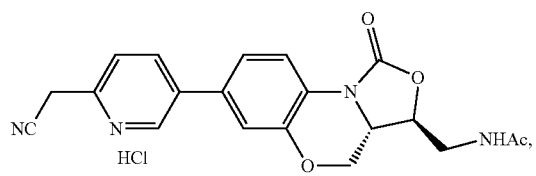

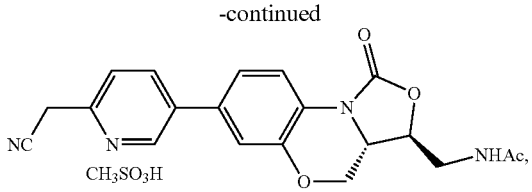

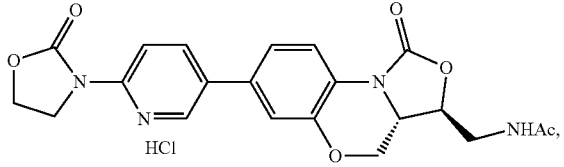

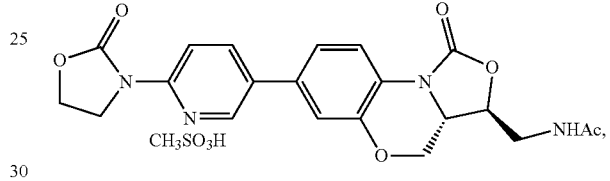

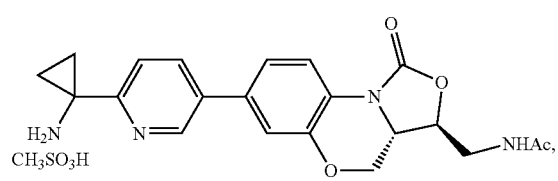

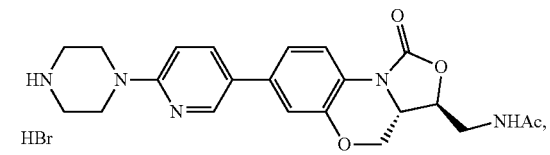

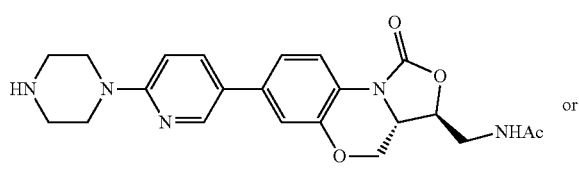

or

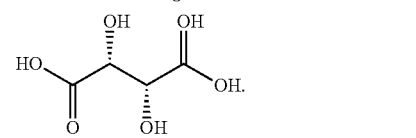

7. Preparation method of benzoxazine oxazolidinone compounds represented by the formula (I), optical isomers or pharmaceutically acceptable salts thereof according to claim 1, comprising:

Scheme I

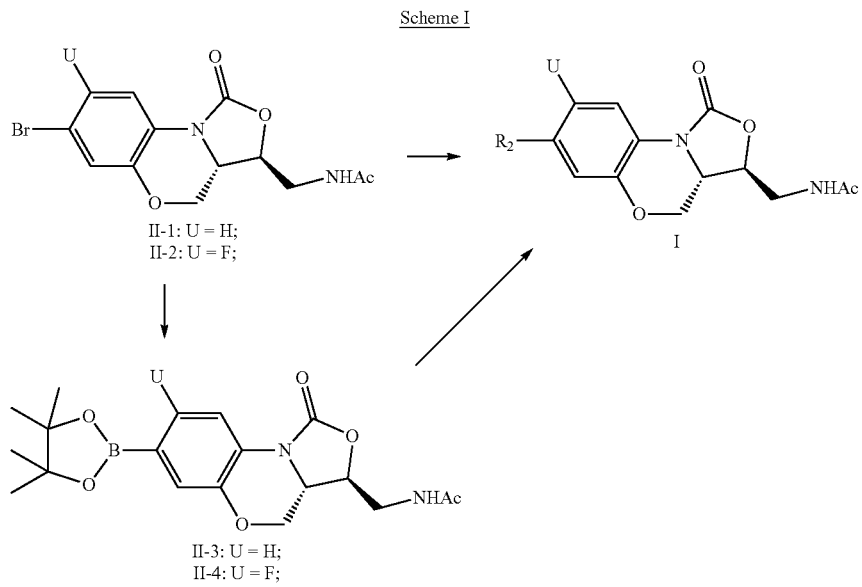

Definition of $R_2$ is the same as in claim 1;

(1) Compound II-1 or II-2 reacts with $R_2B(OH)_2$, or $R_2$-substituted boronic acid pinacol ester under the condition of a catalyst containing metal palladium, alkaline pH, a polar solvent, as well as the protection of inert gas at a temperature range of room temperature to 120° C. for 2-48 hours, to obtain the corresponding Compound I; said catalyst containing metal palladium is $Pd(PPh_3)_4$, $Pd(dppf)Cl_2$, $Pd(dppf)Cl_2.CH_2Cl_2$, $Pd_2(dba)_3$, or $Pd(dba)_2$; for said alkaline condition, the used alkali is: cesium carbonate, potassium carbonate or potassium fluoride; said polar solvent is: 1,4-dioxane, tetrahydrofuran, dimethoxyethane, ethanol or water or mixtures thereof; said inert gas is nitrogen or argon; or (2) Compound II-1 or II-2 reacts with bis(pinacolato)diboron under the condition of a catalyst containing metal palladium, a phosphine-containing ligand, alkaline pH, a polar solvent, as well as the protection of inert gas at a temperature range of room temperature to 100° C. for 0.5 to 48 hours, to obtain Compound II-3 or II-4 respectively; said catalyst containing metal palladium is $Pd(PPh_3)_4$, $Pd(dppf)Cl_2$, $Pd(dppf)Cl_2.CH_2Cl_2$ or $Pd(dba)_2$; said phosphine-containing ligand is biphenyl-2-yl di-tert-butylphosphine; for said alkaline condition, the used alkali is: potassium acetate, sodium acetate, potassium tert-butoxide or sodium tert-butoxide; said polar solvent is: dimethyl sulfoxide, dimethyl formamide, 1,4-dioxane, tetrahydrofuran or toluene; said inert gas is nitrogen or argon;

Compound II-3 or II-4 reacts with bromides $R_2Br$ under the condition of a catalyst containing metal palladium, alkaline pH, a polar solvent, as well as the protection of inert gas at a temperature range of room temperature to 120° C. for 2-24 hours, to obtain corresponding Compound I; said catalyst containing metal palladium is $Pd(PPh_3)_4$, $Pd(dppf)Cl_2.CH_2Cl_2$ or $Pd(dppf)Cl_2$; for said alkaline condition, the used alkali is: cesium carbonate, potassium carbonate or potassium fluoride; said polar solvent is: 1,4-dioxane, tetrahydrofuran, water, dimethoxyethane, ethanol, dimethylformamide or toluene or mixtures thereof; said inert gas is nitrogen or argon; and optionally further including:

(3) Compound I with $R_2$ containing —$NO_2$ in a polar solvent undergoes catalytic hydrogenation under the condition of a metal catalyst to obtain Compound I with $R_2$ containing —$NH_2$; said polar solvent is dichloromethane, methanol, ethanol, tetrahydrofuran or mixtures thereof; said metal catalyst is palladium/carbon;

Scheme II

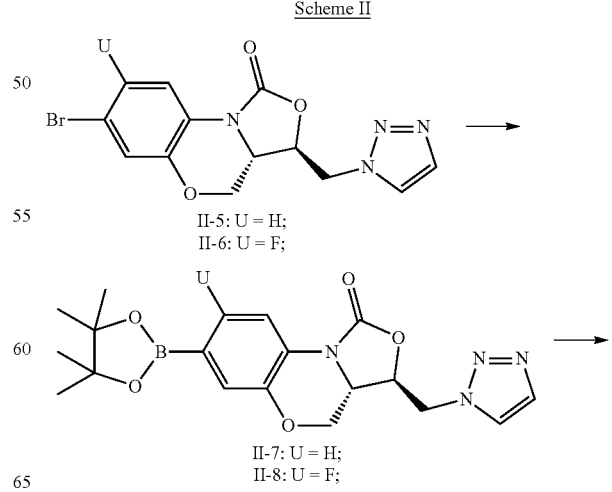

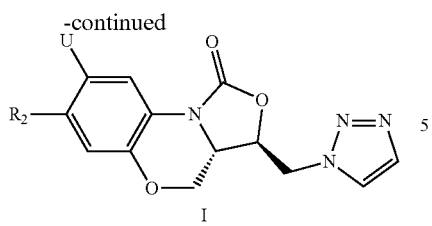

I

Definition of $R_2$ is the same as in claim 1;

Compound II-5 or II-6 reacts with bis(pinacolato)diboron under the condition of catalysis by a catalyst containing metal palladium, a phosphine-containing ligand, alkaline pH, a polar solvent, as well as the protection of inert gas at a temperature range of room temperature to 100° C. for 0.5 to 48 hours, to obtain Compound II-7 or II-8 respectively; said catalyst containing metal palladium is $Pd(dba)_2$, $Pd(dppf)Cl_2 \cdot CH_2Cl_2$ or $Pd(dppf)Cl_2$; said phosphine-containing ligand is biphenyl-2-yl di-tert-butylphosphine; for said alkaline condition, the used alkali is: potassium acetate, sodium acetate, potassium tert-butoxide or sodium tert-butoxide; said polar solvent is dimethyl sulfoxide, 1,4-dioxane or dimethoxyethane; said inert gas is nitrogen or argon;

Compound II-7 or II-8 reacts with bromide $R_2Br$ under the condition of a catalyst containing metal palladium, alkaline pH, a polar solvent, as well as the protection of inert gas at a temperature range of room temperature to 120° C. for 2-24 hours, to obtain corresponding Compound I; said catalyst containing metal palladium is $Pd(dba)_2$, $Pd(dppf)Cl_2 \cdot CH_2Cl_2$ or $Pd(dppf)Cl_2$; for said alkaline condition, the used alkali is: potassium acetate, potassium carbonate or sodium acetate; said polar solvent is dimethylformamide, 1,4-dioxane, ethanol, water or mixtures thereof; said inert gas is nitrogen or argon.

8. Preparation method of benzoxazine oxazolidinone compounds represented by the formula (I), optical isomers or pharmaceutically acceptable salts thereof according to claim 7, wherein, said Compound II-2 is prepared according to the following method:

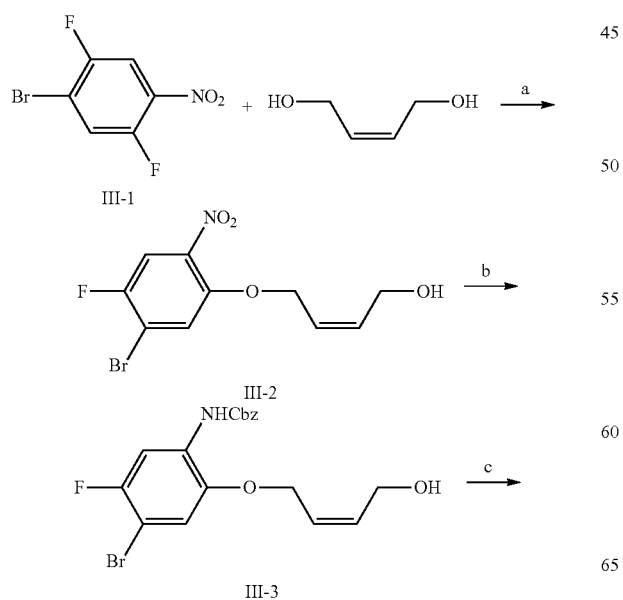

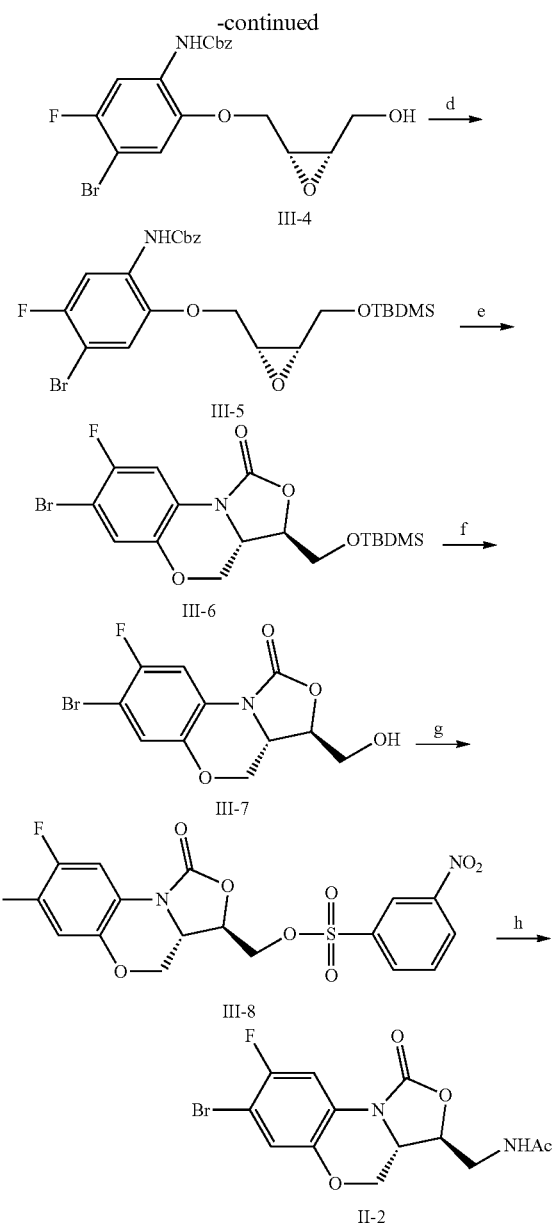

a. Compound III-1 reacts with (Z)-2-Butene-1,4-diol under the condition of alkaline pH, a molecular sieve, a polar solvent, as well as the protection of inert gas at −20° C. to 120° C. for 1 to 24 hours to produce Compound III-2; for said alkaline condition, the used alkali is: potassium carbonate, sodium hydride, sodium hydroxide or potassium hydroxide; said molecular sieve is 4 Å molecular sieve; said polar solvent is dimethylformamide, tetrahydrofuran or dimethoxyethane; said inert gas is nitrogen or argon;

b. Compound III-2 reacts under the condition of a reducing agent and a polar solvent at room temperature for 2-48 hours so that the nitro group is reduced to obtain corresponding amino compound; said reducing agent is zinc powder, iron powder, ammonium formate or ammonium chloride; said polar solvent is methanol or THF; said amino compound continues to react with benzyloxycarbonyl chloride under alkaline condition and in a polar solvent to obtain Compound III-3, in which the amino group is protected by the benzyloxycarbonyl group; for said alkaline condition, the used alkali is: sodium bicarbonate, potassium bicarbonate, sodium carbonate or potassium carbonate; said polar solvent is water, acetone, or tetrahydrofuran or mixtures thereof;

c. Compound III-3 and oxidant undergo sharpless epoxidation reaction under the condition of L-(+)-tartaric ester, a titanium reagent, and a molecular sieve, as well as in a polar solvent at a temperature range of room temperature to 40° C. to obtain the corresponding chiral epoxidation product III-4; said oxidant is toluene solution dissolved with tert-t-butyl hydroperoxide; said tartaric ester is L-(+)-diethyl tartrate or L-(+)-dimethyl tartrate; said molecular sieve is 4 Å molecular sieve; said titanium reagent is titanium tetraisopropoxide; said polar solvent is dichloromethane or chloroform;

d. Compound III-4 reacts with tert-butyldimethylsilyl chloride in the presence of an organic alkali and in a polar solvent at room temperature for 2-6 hours to obtain Compound III-5; said organic alkali is imidazole or 4-dimethylamino pyridine; said polar solvent is dimethylformamide, dimethyl sulfoxide, tetrahydrofuran or 1,4-dioxane;

e. Compound III-5 reacts under condition of a strong alkali and in a polar solvent at a temperature range of room temperature to 78° C. for 6-24 hours, to obtain Compound III-6; the strong alkali, used for said condition is n-butyllithium or lithium diisopropylamide; said polar solvent is tetrahydrofuran or dimethoxyethane;

f. Compound III-6 reacts in the presence of a fluorine-containing reagent, in a polar solvent and at room temperature for 1-6 hours, to produce Compound III-7 through removal of the tert-butyldimethylsilyl protecting group; said fluorine-containing reagent is tetra-n-butylammonium fluoride; said polar solvent is tetrahydrofuran or dimethoxyethane;

g. Compound III-7 reacts with 3-nitrobenzenesulfonyl chloride in the presence of an organic alkali, in a polar solvent, and at a temperature range of room temperature to 10° C. for 2-12 hours to obtain corresponding Compound III-8; said organic alkali, is triethylamine or pyridine; said polar solvent is dichloromethane or chloroform;

h. Compound III-8 reacts with stronger ammonia water in a polar solvent at a temperature range of room temperature to 80° C. for 24-72 hours to obtain corresponding amino compound; said polar solvent is acetonitrile, isopropanol, or ethanol or mixtures thereof; said amino compound reacts with acetylating agent in the presence of an organic alkali, in a polar solvent and at a temperature range of room temperature to 10° C. for 0.5-8 hours to obtain the corresponding Compound II-2; said organic alkali is triethylamine or pyridine; said polar solvent is dichloromethane or chloroform.

9. Preparation method of benzoxazine oxazolidinone compounds represented by the formula (I), optical isomers or pharmaceutically acceptable salts thereof according to claim 7, wherein, said Compound II-5 and II-6 is prepared according to the following method:

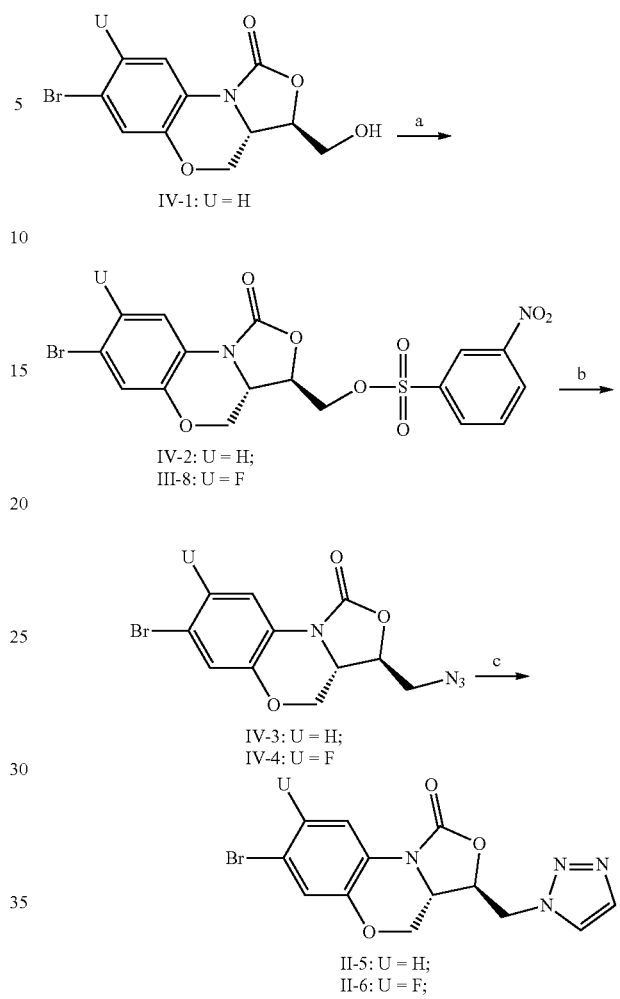

IV-1: U = H

IV-2: U = H;
III-8: U = F

IV-3: U = H;
IV-4: U = F

II-5: U = H;
II-6: U = F;

a. Compound IV-1 reacts with 3-nitrobenzenesulfonyl chloride in the presence of an organic alkali, in a polar solvent, and at a temperature range of room temperature to 10° C. for 2-12 hours to obtain corresponding Compound IV-2; said organic alkali is triethylamine or pyridine; said polar solvent is dichloromethane or chloroform;

b. Compound IV-2 or III-8 reacts with an azide in a polar solvent at a temperature range of room temperature to 120° C. for 1-48 hours, to obtain Compound IV-3 and IV-4 respectively; said polar solvent is dimethylformamide or dimethyl sulfoxide; said azide is sodium azide, potassium azide or trimethylsilyl azide;

c. Compound IV-3 and IV-4 reacts in vinyl acetate, in the presence of a copper-containing catalyst and being heated to 40-80° C. for 12-84 hours, to obtain Compound II-5 and II-6; said copper-containing catalyst is cuprous chloride or cuprous iodide.

10. A method for treating an infectious disease caused by multi-drug resistant bacteria selected from the group consisting of *Enterococcus, Staphylococcus aureus, Staphylococcus epidermidis*, and *pneumococcus*, which comprises administering a therapeutically effective benzoxazine oxazolidinone compound represented by the formula (I), or an optical isomers or pharmaceutically acceptable salt thereof

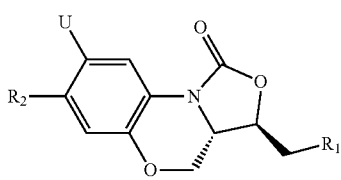

wherein:
U is H or F;
$R_1$ is

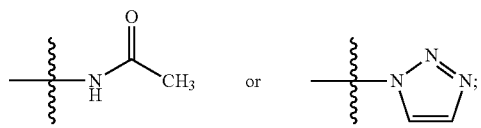

$R_2$ is a phenyl group, or a five membered or six membered aromatic or non-aromatic heterocyclic group;
said phenyl group is optionally substituted by F, —CN, —$NH_2$ or $C_1$-$C_3$ alkylcarbonyl group;
said five membered or six membered aromatic or non-aromatic heterocyclic group comprises at least one heteroatom selected from N, O or S;
Said five membered or six membered aromatic or non-aromatic heterocyclic group may optionally be substituted by the following functional groups: F, Cl, Br, —OH, —$NO_2$, —CHO, —CN, —$NH_2$, —$CF_3$, —C≡CH, —C≡$CCH_2OH$, —COOH, —$OR_3$, —NH$COR_3$, —$COR_3$, —$CONR_3R_4$, and —$COOR_3$, wherein each of $R_3$ and $R_4$ can independently be a $C_1$-$C_3$ alkyl;
or said five membered or six membered aromatic or non-aromatic heterocyclic group may optionally be substituted by $C_1$-$C_6$ straight chain or branched chain alkyl group, or $C_3$-$C_6$ cycloalkyl group, and said $C_1$-$C_6$ straight chain or branched chain alkyl group or $C_3$-$C_6$ cycloalkyl group may optionally be substituted by —OH, —CN, or —$NH_2$;
or said five membered or six membered aromatic or non-aromatic heterocyclic group may optionally be substituted by five membered or six membered aromatic or non-aromatic heterocyclic group, which comprises at least one heteroatom selected from N and O and is either unsubstituted or substituted by $C_1$-$C_3$ alkyl or oxygen, to a living organism in need of said treatment.

11. A pharmaceutical composition, comprising a therapeutically effective amount of one or more of the benzoxazine oxazolidinone compounds represented by formula (I), optical isomers or pharmaceutically acceptable salts thereof according to claim 1 as an active ingredient, as well as pharmaceutically acceptable excipients.

12. A pharmaceutical composition, comprising a therapeutically effective amount of one or more of the benzoxazine oxazolidinone compounds represented by formula (I), optical isomers or pharmaceutically acceptable salts thereof according to claim 2 as an active ingredient, as well as pharmaceutically acceptable excipients.

13. A pharmaceutical composition, comprising a therapeutically effective amount of one or more of the benzoxazine oxazolidinone compounds represented by formula (I), optical isomers or pharmaceutically acceptable salts thereof according to claim 3 as an active ingredient, as well as pharmaceutically acceptable excipients.

14. A pharmaceutical composition, comprising a therapeutically effective amount of one or more of the benzoxazine oxazolidinone compounds represented by formula (I), optical isomers or pharmaceutically acceptable salts thereof according to claim 4 as an active ingredient, as well as pharmaceutically acceptable excipients.

15. A pharmaceutical composition, comprising a therapeutically effective amount of one or more of the benzoxazine oxazolidinone compounds represented by formula (I), optical isomers or pharmaceutically acceptable salts thereof according to claim 5 as an active ingredient, as well as pharmaceutically acceptable excipients.

16. A pharmaceutical composition, comprising a therapeutically effective amount of one or more of the benzoxazine oxazolidinone compounds represented by formula (I), optical isomers or pharmaceutically acceptable salts thereof according to claim 6 as an active ingredient, as well as pharmaceutically acceptable excipients.

\* \* \* \* \*